(12) United States Patent
Agah et al.

(10) Patent No.: US 10,099,040 B2
(45) Date of Patent: Oct. 16, 2018

(54) OCCLUSION CATHETER SYSTEM AND METHODS OF USE

(71) Applicant: RenovoRx, Inc., Los Altos, CA (US)

(72) Inventors: Ramtin Agah, Menlo Park, CA (US); Kamran Najmabadi, Palo Alto, CA (US); Shaun R. Bagai, Mountain View, CA (US); Reza Malek, Atherton, CA (US)

(73) Assignee: RenovoRx, Inc., Los Altos, CA (US)

( * ) Notice: Subject to any disclaimer, the term of this patent is extended or adjusted under 35 U.S.C. 154(b) by 0 days.

(21) Appl. No.: 14/958,428

(22) Filed: Dec. 3, 2015

(65) Prior Publication Data
US 2017/0157370 A1   Jun. 8, 2017

(51) Int. Cl.
*A61M 25/10* (2013.01)
*A61M 39/24* (2006.01)
*A61B 17/12* (2006.01)

(52) U.S. Cl.
CPC ........ *A61M 25/1011* (2013.01); *A61M 39/24* (2013.01); *A61B 17/1214* (2013.01); *A61M 2025/105* (2013.01); *A61M 2025/1015* (2013.01); *A61M 2025/1045* (2013.01);
(Continued)

(58) Field of Classification Search
CPC ............ A61M 25/1011; A61M 25/007; A61M 25/1025; A61M 25/0136; A61M 2025/1052; A61M 2025/0076; A61M 2025/0006; A61M 2025/0004; A61M 2025/1045; A61M 2025/1015
See application file for complete search history.

(56) References Cited

U.S. PATENT DOCUMENTS

| 4,445,892 A | 5/1984 | Hussein et al. |
| 4,655,746 A | 4/1987 | Daniels et al. |
| 4,696,304 A | 9/1987 | Chin |

(Continued)

FOREIGN PATENT DOCUMENTS

| EP | 0 402 467 A1 | 12/1990 |
| EP | 1 303 228 B1 | 9/2012 |

(Continued)

OTHER PUBLICATIONS

US 7,316,661, 01/2008, Zadno-Azizi (withdrawn)
(Continued)

*Primary Examiner* — Andrew Gilbert

(57) ABSTRACT

In some embodiments, an apparatus includes a first catheter movably disposed within a first lumen of a second catheter. The first catheter has a first occlusion member disposed at a distal end portion and the second catheter has a second occlusion member disposed at a distal end portion. A third catheter has a third occlusion member disposed at a distal end portion and is moveably disposable within a second lumen of the second catheter. The second catheter has a side port in fluid communication with the second lumen and the third catheter can be extended out of the second lumen through the side port. The first occlusion member, second occlusion member and third occlusion member can collectively isolate a target region including a portion of a first body lumen (e.g., a main vessel) and a portion of a second body lumen (e.g., a branch of the main vessel).

20 Claims, 30 Drawing Sheets

(52) U.S. Cl.
CPC .............. *A61M 2025/1052* (2013.01); *A61M 2210/1042* (2013.01); *A61M 2210/12* (2013.01)

(56) References Cited

U.S. PATENT DOCUMENTS

| | | | |
|---|---|---|---|
| 4,714,460 A | 12/1987 | Calderon | |
| 4,830,003 A | 5/1989 | Wolff et al. | |
| 4,883,459 A | 11/1989 | Calderon | |
| 5,281,200 A | 1/1994 | Corso, Jr. et al. | |
| 5,318,535 A | 6/1994 | Miraki | |
| 5,338,301 A | 8/1994 | Diaz | |
| 5,397,307 A | 3/1995 | Goodin | |
| 5,415,636 A | 5/1995 | Forman | |
| 5,419,763 A | 5/1995 | Hildebrand | |
| 5,462,529 A | 10/1995 | Simpson et al. | |
| 5,478,309 A | 12/1995 | Sweezer et al. | |
| 5,484,412 A | 1/1996 | Pierpont | |
| 5,514,092 A | 5/1996 | Forman et al. | |
| 5,575,815 A | 11/1996 | Slepian et al. | |
| 5,772,632 A | 6/1998 | Forman | |
| 5,810,757 A | 9/1998 | Sweezer, Jr. et al. | |
| 5,833,644 A | 11/1998 | Zadno-Azizi et al. | |
| 5,833,650 A | 11/1998 | Imran | |
| 5,833,672 A | 11/1998 | Kawata et al. | |
| 5,836,905 A | 11/1998 | Lemelson et al. | |
| 5,836,967 A | 11/1998 | Schneider | |
| 5,840,066 A | 11/1998 | Matsuda et al. | |
| 5,843,050 A * | 12/1998 | Jones ............... | A61M 25/0012 604/525 |
| 5,916,193 A * | 6/1999 | Stevens .............. | A61M 1/3659 604/28 |
| 5,919,163 A | 7/1999 | Glickman | |
| 5,925,016 A | 7/1999 | Chornenky et al. | |
| 5,961,536 A | 10/1999 | Mickley et al. | |
| 5,968,012 A | 10/1999 | Ren et al. | |
| 6,030,362 A | 2/2000 | Boussignac et al. | |
| 6,051,014 A | 4/2000 | Jang | |
| 6,083,198 A * | 7/2000 | Afzal ................. | A61M 25/007 604/101.01 |
| 6,126,635 A | 10/2000 | Simpson et al. | |
| 6,156,053 A | 12/2000 | Gandhi et al. | |
| 6,165,152 A | 12/2000 | Becker et al. | |
| 6,176,844 B1 | 1/2001 | Lee | |
| 6,287,290 B1 | 9/2001 | Perkins et al. | |
| 6,299,598 B1 | 10/2001 | Bander | |
| 6,346,098 B1 | 2/2002 | Yock et al. | |
| 6,351,663 B1 | 2/2002 | Flower et al. | |
| 6,436,090 B1 | 8/2002 | Sanchez et al. | |
| 6,440,097 B1 * | 8/2002 | Kupiecki ......... | A61B 17/12022 604/509 |
| 6,461,327 B1 | 10/2002 | Addis et al. | |
| 6,482,172 B1 | 11/2002 | Thramann | |
| 6,485,500 B1 | 11/2002 | Kokish et al. | |
| 6,488,672 B1 | 12/2002 | Dance et al. | |
| 6,508,777 B1 | 1/2003 | Macoviak et al. | |
| 6,520,183 B2 | 2/2003 | Amar | |
| 6,569,146 B1 | 5/2003 | Werner et al. | |
| 6,569,148 B2 | 5/2003 | Bagaoisan et al. | |
| 6,575,932 B1 | 6/2003 | O'Brien et al. | |
| 6,589,264 B1 | 7/2003 | Barbut et al. | |
| 6,592,546 B1 | 7/2003 | Barbut et al. | |
| 6,682,499 B2 | 1/2004 | Lenker | |
| 6,685,672 B1 | 2/2004 | Forman | |
| 6,692,458 B2 | 2/2004 | Forman et al. | |
| 6,699,231 B1 | 3/2004 | Sterman et al. | |
| 6,702,781 B1 | 3/2004 | Reifart et al. | |
| 6,706,013 B1 | 3/2004 | Bhat et al. | |
| 6,706,062 B2 * | 3/2004 | Vardi ................ | A61F 2/82 623/1.15 |
| 6,712,806 B2 | 3/2004 | St. Germain et al. | |
| 6,723,070 B1 | 4/2004 | Arai et al. | |
| 6,743,196 B2 | 6/2004 | Barbut et al. | |
| 6,749,581 B2 | 6/2004 | Thompson et al. | |
| 6,884,233 B2 | 4/2005 | Dance et al. | |
| 6,929,633 B2 | 8/2005 | Evans et al. | |
| 6,939,320 B2 | 9/2005 | Lennox | |
| 6,986,788 B2 | 1/2006 | Paul et al. | |
| 6,997,898 B2 | 2/2006 | Forman | |
| 7,150,736 B2 | 12/2006 | Barbut et al. | |
| 7,179,251 B2 | 2/2007 | Palasis | |
| 7,297,475 B2 | 11/2007 | Koiwai et al. | |
| 7,452,532 B2 | 11/2008 | Alt | |
| 7,503,904 B2 | 3/2009 | Choi | |
| 7,537,562 B2 | 5/2009 | Takano | |
| 7,645,259 B2 | 1/2010 | Goldman | |
| 7,708,715 B2 | 5/2010 | Gellman | |
| 7,780,628 B1 | 8/2010 | Keren et al. | |
| 7,815,624 B2 | 10/2010 | Larson | |
| 7,887,661 B2 | 2/2011 | Chiu et al. | |
| 8,043,257 B2 | 10/2011 | Nguyen et al. | |
| 8,088,103 B2 | 1/2012 | Teeslink et al. | |
| 8,162,879 B2 | 4/2012 | Hattangadi et al. | |
| 8,172,792 B2 | 5/2012 | Wang et al. | |
| 8,177,829 B2 | 5/2012 | Benson et al. | |
| 8,182,446 B2 | 5/2012 | Schaeffer et al. | |
| 8,182,463 B2 | 5/2012 | Chiu et al. | |
| 8,187,229 B2 | 5/2012 | Weitzner et al. | |
| 8,251,948 B2 | 8/2012 | Goldman | |
| 8,262,611 B2 | 9/2012 | Teeslink et al. | |
| 8,262,613 B2 | 9/2012 | Lennox | |
| 8,414,473 B2 | 4/2013 | Jenkins et al. | |
| 8,702,678 B2 | 4/2014 | Comerota et al. | |
| 8,784,602 B2 * | 7/2014 | Schaeffer .......... | A61M 25/10 156/293 |
| 8,821,476 B2 * | 9/2014 | Agah ................. | A61M 25/007 600/433 |
| 8,870,849 B2 | 10/2014 | Steinmetz et al. | |
| 9,180,281 B2 | 11/2015 | Gerrans et al. | |
| 9,254,210 B2 * | 2/2016 | Bourang ............ | A61F 2/954 |
| 9,457,171 B2 | 10/2016 | Agah et al. | |
| 9,463,304 B2 | 10/2016 | Agah et al. | |
| 2001/0041862 A1 | 11/2001 | Glickman | |
| 2002/0082548 A1 | 6/2002 | Sanchez et al. | |
| 2002/0107471 A1 | 8/2002 | Thompson et al. | |
| 2002/0115982 A1 | 8/2002 | Barbut et al. | |
| 2005/0059930 A1 | 3/2005 | Garrison et al. | |
| 2005/0059931 A1 | 3/2005 | Garrison et al. | |
| 2005/0149112 A1 | 7/2005 | Barbut | |
| 2006/0009798 A1 | 1/2006 | Callister et al. | |
| 2006/0149393 A1 | 7/2006 | Calderon | |
| 2006/0200075 A1 * | 9/2006 | Zadno-Azizi ..... | A61B 17/12045 604/101.05 |
| 2007/0055132 A1 * | 3/2007 | Camus .............. | A61M 25/1011 600/407 |
| 2008/0058759 A1 * | 3/2008 | Makower .......... | A61M 25/0084 604/509 |
| 2008/0269718 A1 | 10/2008 | Wiener et al. | |
| 2009/0018526 A1 | 1/2009 | Power et al. | |
| 2009/0043194 A1 * | 2/2009 | Barbut .............. | A61B 17/12036 600/435 |
| 2009/0048577 A1 | 2/2009 | Gillies et al. | |
| 2009/0088676 A1 | 4/2009 | Murata | |
| 2009/0131866 A1 | 5/2009 | Zhang et al. | |
| 2009/0264819 A1 | 10/2009 | Diethrich et al. | |
| 2009/0275918 A1 | 11/2009 | Crocker | |
| 2010/0016836 A1 | 1/2010 | Makower et al. | |
| 2010/0106181 A1 | 4/2010 | Gross et al. | |
| 2011/0093000 A1 | 4/2011 | Ogle et al. | |
| 2011/0152683 A1 | 6/2011 | Gerrans et al. | |
| 2011/0218494 A1 * | 9/2011 | Gerrans .......... | A61B 17/320725 604/101.05 |
| 2011/0257577 A1 | 10/2011 | Lane et al. | |
| 2011/0295114 A1 * | 12/2011 | Agah ................ | A61M 25/007 600/435 |
| 2012/0259215 A1 * | 10/2012 | Gerrans ........... | A61M 25/1011 600/435 |
| 2013/0268047 A1 * | 10/2013 | Bourang ........... | A61F 2/852 623/1.11 |
| 2014/0214002 A1 * | 7/2014 | Lieber .............. | A61M 25/104 604/509 |
| 2014/0276135 A1 | 9/2014 | Agah et al. | |

(56) References Cited

U.S. PATENT DOCUMENTS

2016/0015948 A1 1/2016 Agah et al.
2016/0082178 A1 3/2016 Agah et al.
2017/0056629 A1 3/2017 Agah et al.

FOREIGN PATENT DOCUMENTS

| WO | WO 89/07413 | 8/1989 |
| WO | WO 01/070325 A2 | 9/2001 |
| WO | WO 02/074178 A2 | 9/2002 |
| WO | WO 2011/068946 | 6/2011 |
| WO | WO 2014/197362 A1 | 12/2014 |
| WO | WO 2016/011328 | 1/2016 |

OTHER PUBLICATIONS

International Search Report and Written Opinion for PCT/US10/58684, dated Feb. 17, 2011.
International Search Report and Written Opinion for PCT/US14/40485, dated Nov. 3, 2014.
European Search Report for European Patent Application No. 10835110.7, dated Mar. 21, 2013.
Office Action for European Patent Application No. 10835110.7, dated Jun. 1, 2015.
Office Action for U.S. Appl. No. 12/958,711, dated Aug. 20, 2013.
Office Action for U.S. Appl. No. 12/958,711, dated Mar. 7, 2014.
Office Action for U.S. Appl. No. 14/293,603, dated Dec. 15, 2015.
Office Action for U.S. Appl. No. 14/870,833, dated Dec. 14, 2015.
Office Action for U.S. Appl. No. 14/293,603, dated May 10, 2016, 17 pages.
Office Action for U.S. Appl. No. 14/870,833, dated May 9, 2016, 11 pages.
Office Action for U.S. Appl. No. 14/958,415, dated Mar. 2, 2016 13 pages.
Office Action for European Application No. 10835110.7, dated Jan. 25, 2017, 5 pages.

\* cited by examiner

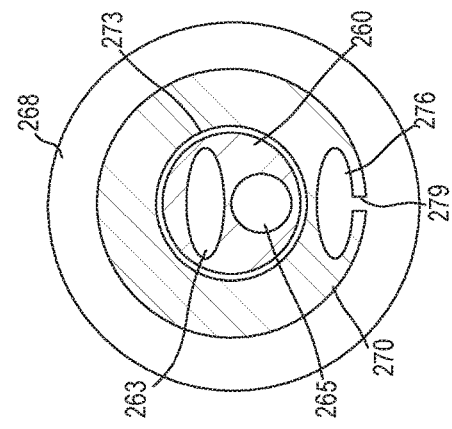
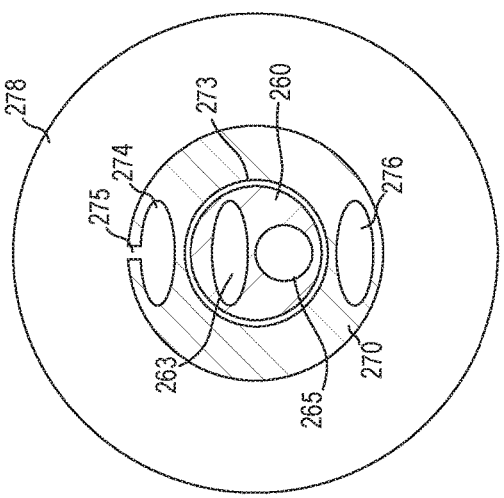
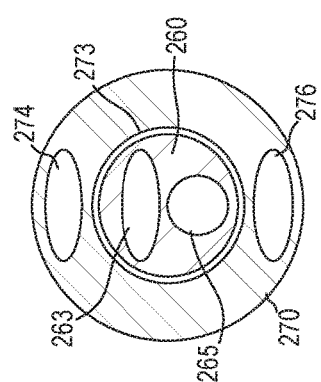
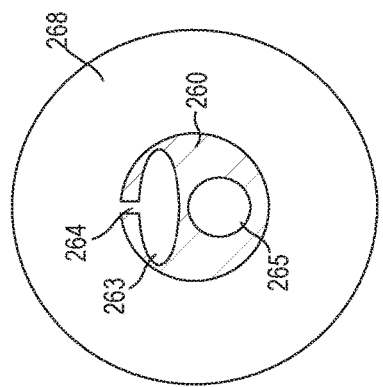
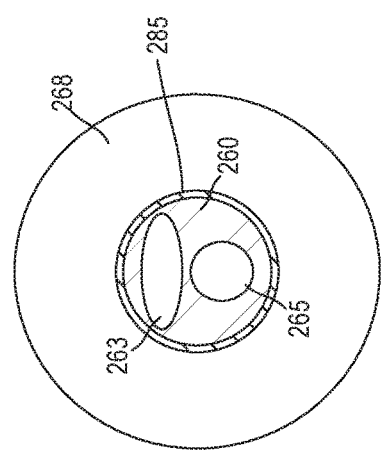

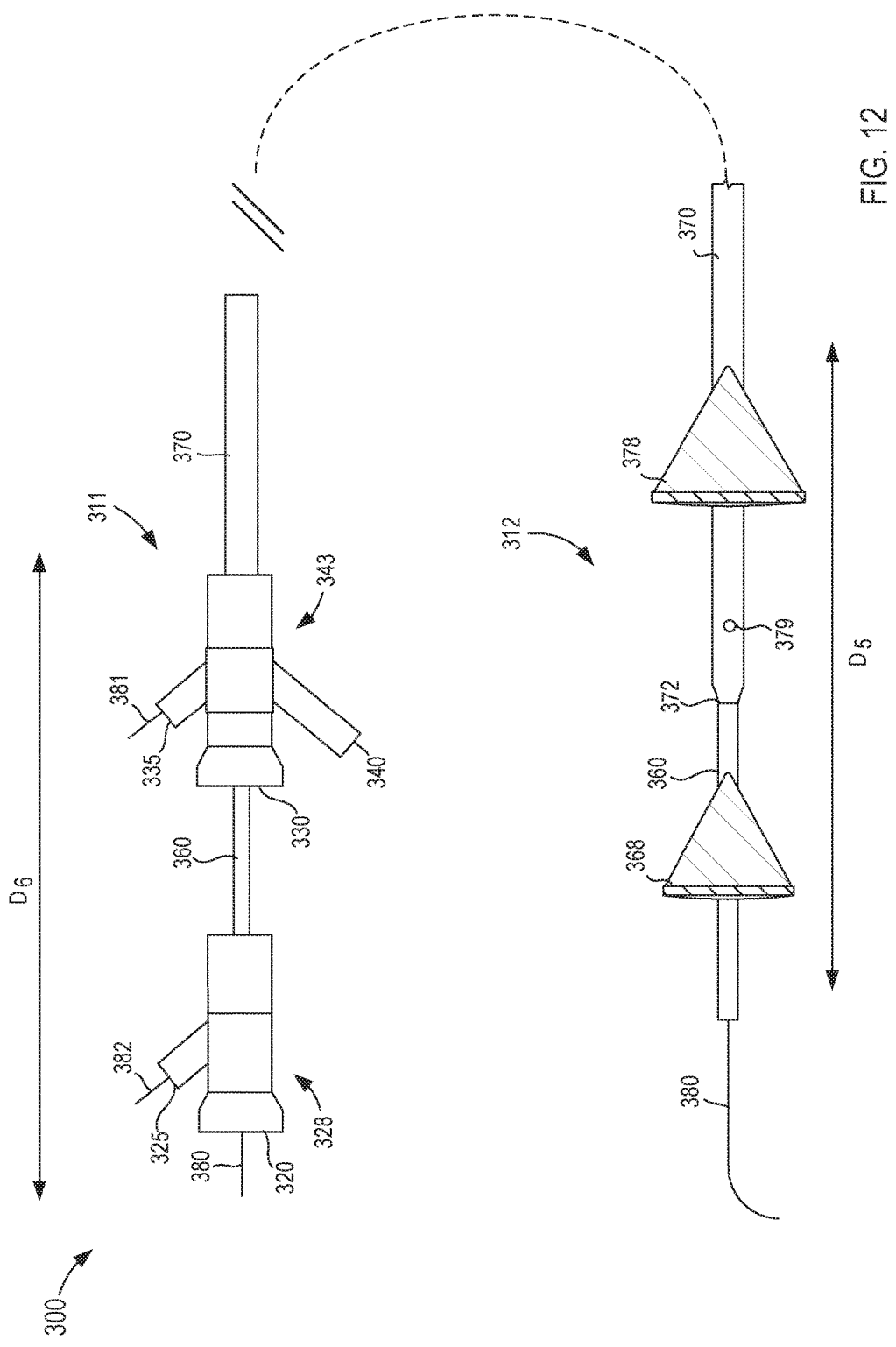

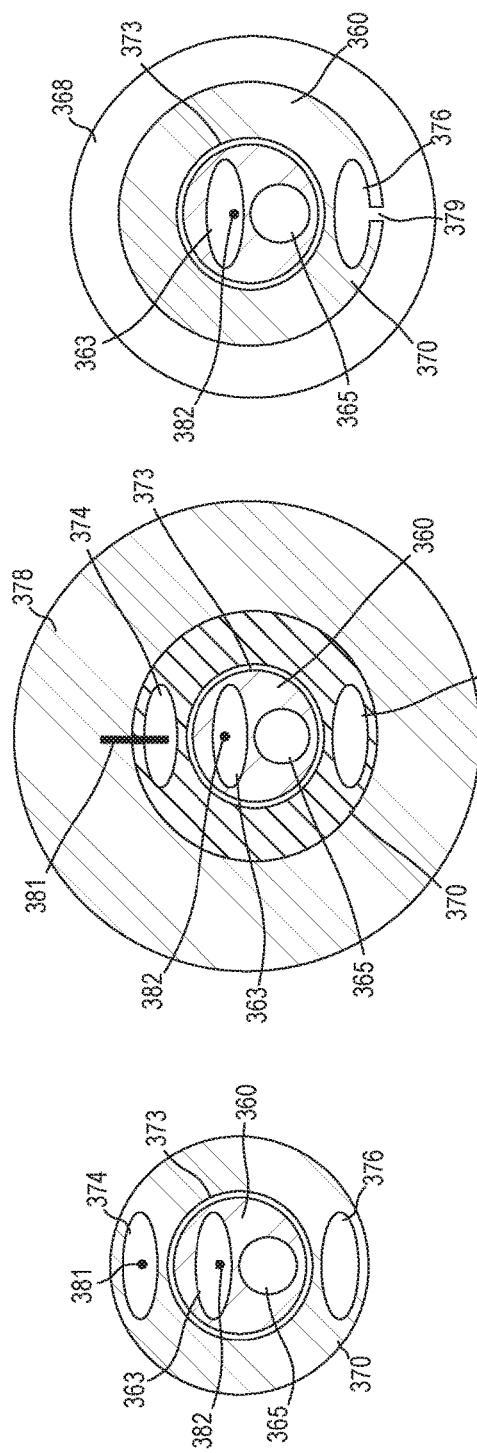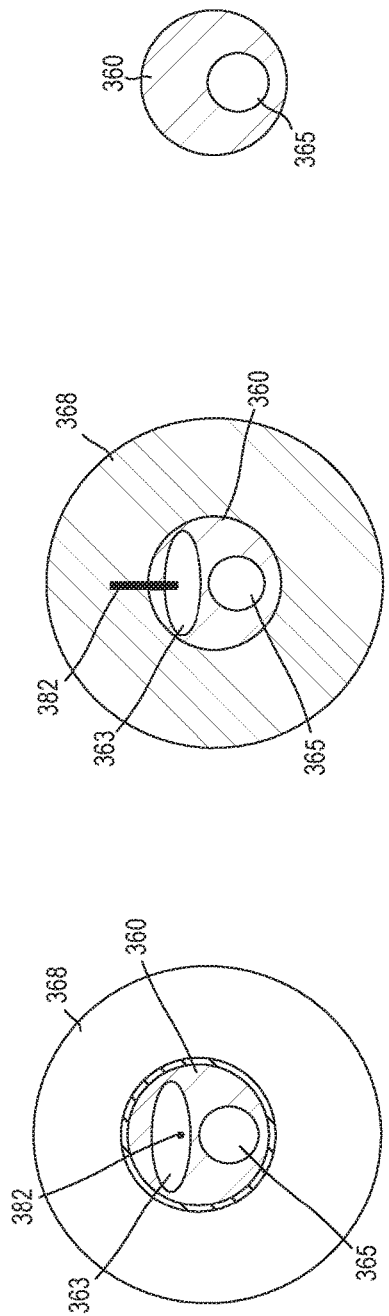

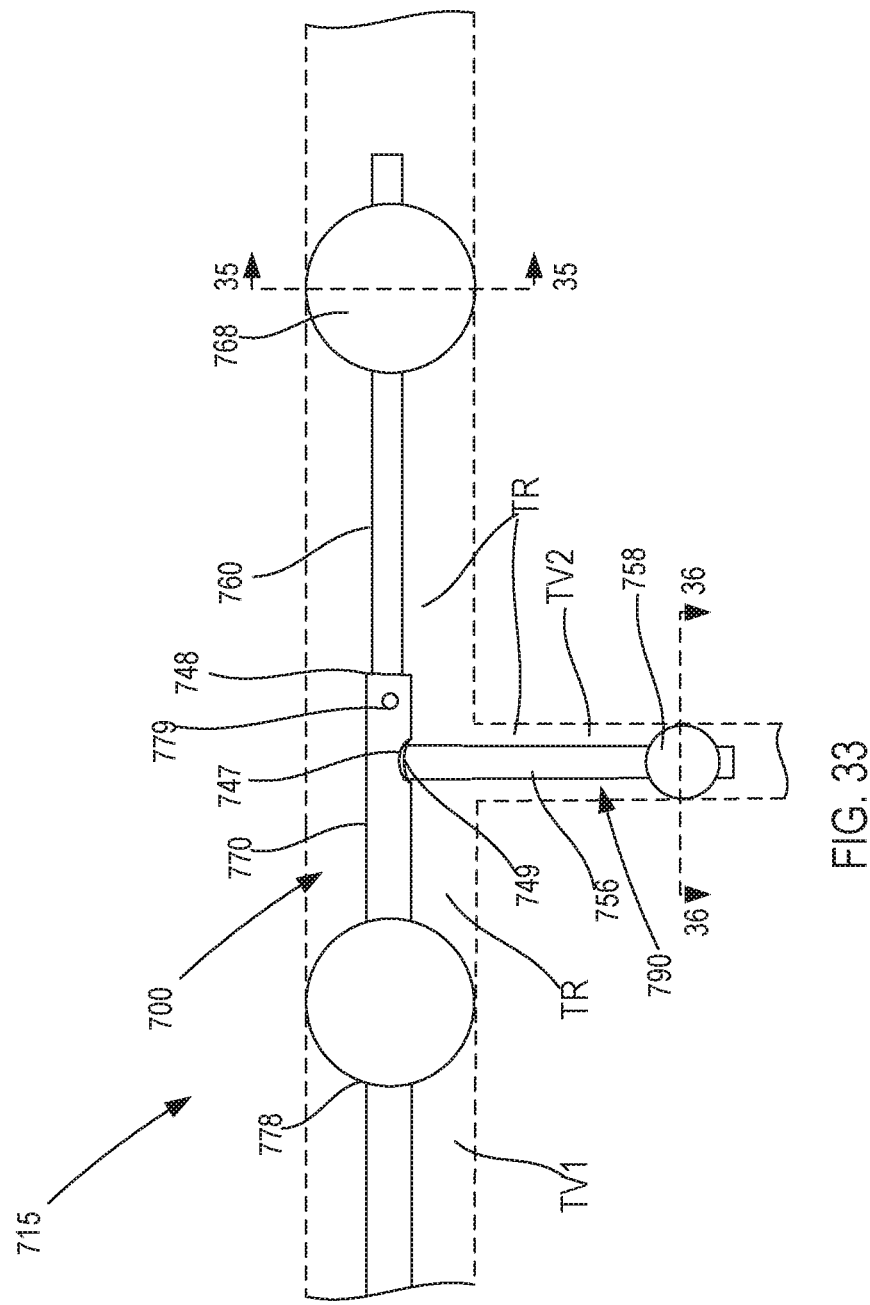

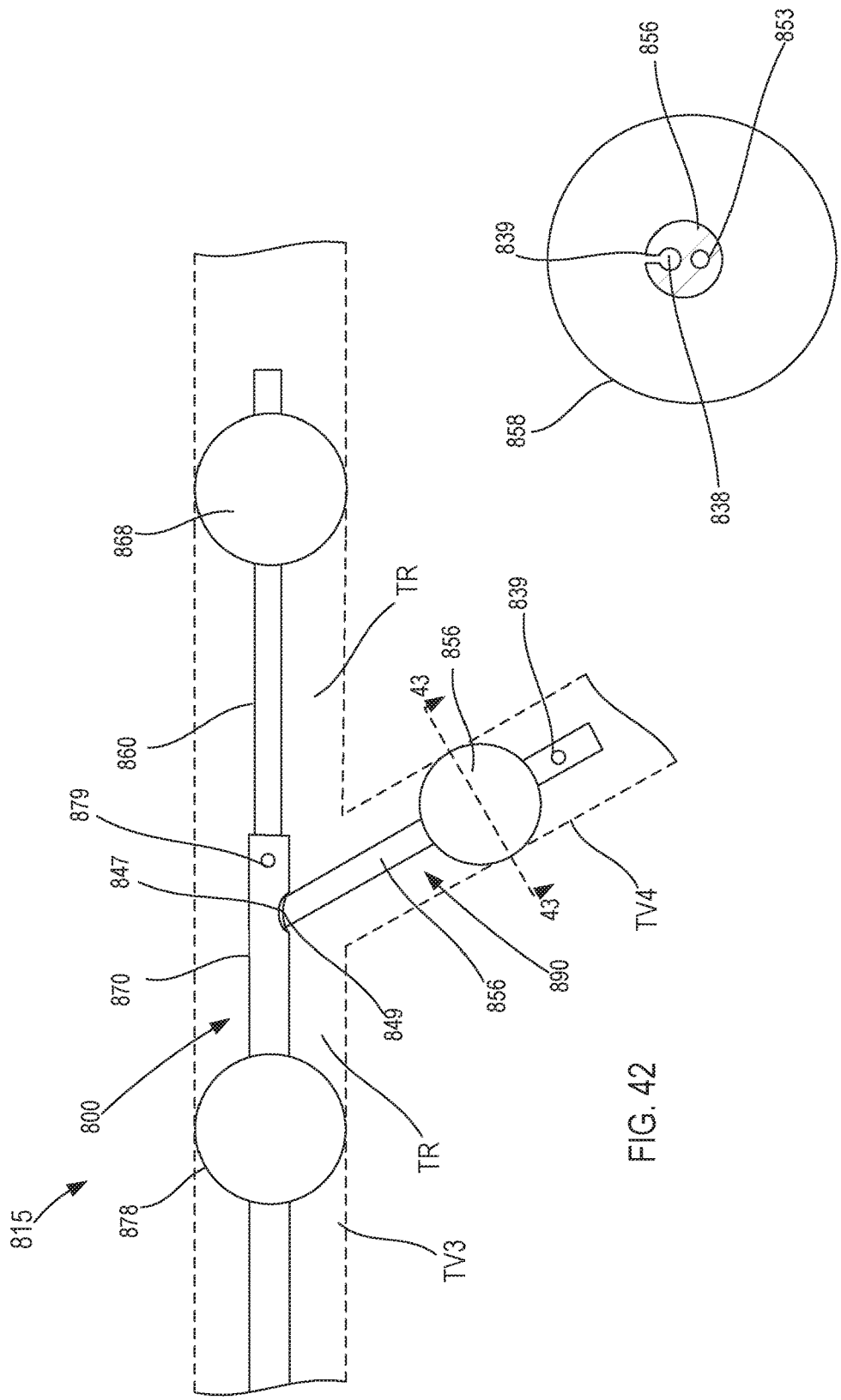

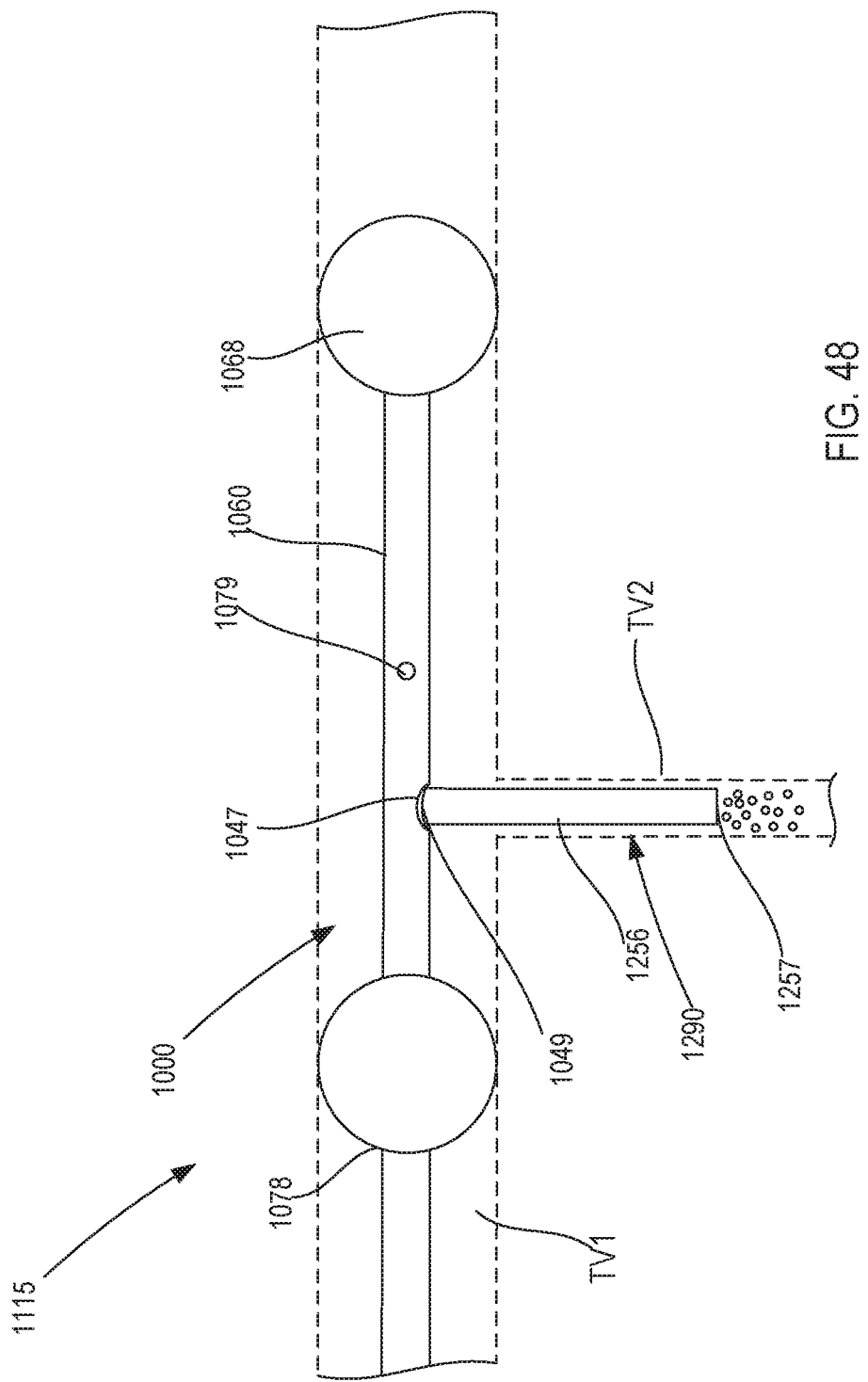

OCCLUSION CATHETER SYSTEM AND METHODS OF USE

CROSS-REFERENCE TO RELATED APPLICATIONS

This application is related to U.S. patent application Ser. No. 14/293,603, entitled "Devices, Methods and Kits for the Delivery of Therapeutic Materials to a Pancreas," filed Jun. 2, 2014, now U.S. Pat. No. 9,457,171, which claims priority to and the benefit U.S. Provisional Patent Application No. 61/830,218, filed Jun. 3, 2013, entitled "Apparatus and Methods for Insertion and Manipulation of Multi-Occlusion Catheter Device," each of the disclosures of which is incorporated herein by reference in its entirety.

This application is also related to U.S. patent application Ser. No. 12/958,711, entitled "Devices, Methods and Kits for the Delivery of Therapeutic Materials to a Pancreas," filed Dec. 2, 2010, now U.S. Pat. No. 8,821,476, which claims priority to and the benefit of U.S. Provisional Patent Application No. 61/265,845 entitled "A Catheter System Adapted for Endovascular Delivery of Therapeutic Materials to a Mammalian Pancreas, Method of Treatment of Diabetes, and Kits Therefore," filed Dec. 2, 2009, each of the disclosures of which is incorporated herein by reference in its entirety.

BACKGROUND

The embodiments described herein relate generally to medical devices and more particularly, to apparatus, kits, and methods for insertion and manipulation of a multi-occlusion catheter system to, for example, deliver a therapeutic material to an artery, organ and/or other bodily tissue.

In some instances, systemic treatments are used to treat disease within a patient. The effectiveness of some such systemic treatments can vary due at least in part to the treatment (e.g., a biologic agent and/or drug formulation) not reaching target tissue. For example, in the treatment of some diseases, such as cancer, it may be desirable to deliver biological cells or other treatment therapies to a cancerous organ (such as, for example, the pancreas) where efficient and safe engraftment can be achieved.

In some cases, it may be desirable to deliver a drug or other treatment therapy to a segment of an artery where there is a side branch which may act as an escape route for localized treatment agents (e.g., chemotherapy). In such situations, the area of interest to be treated can be occluded with an occlusion catheter to isolate the area of interest; however, because of the side branch full occlusion of the area of interest may be impeded.

Thus, a need exists for improved apparatus, kits, and methods for delivering a treatment such as a biologic agent and/or drug formulation to a target tissue with minimal dosing to the surrounding organ(s). There is also a need for a catheter device or system that can be used to occlude an artery or vessel to be treated, occlude any side branch vessel, and to introduce a treatment agent (e.g., chemotherapy, cell therapy, etc.) using the same catheter device/system.

SUMMARY

Devices, kits, and methods are described herein that can be used, for example, for the insertion and manipulation of a multi-occlusion catheter system to deliver a treatment to, for example, an artery, an organ and/or a malformation such as a tumor. In some embodiments, an apparatus includes a first catheter movably disposed within a first lumen of a second catheter. The first catheter has a first occlusion member disposed at a distal end portion and the second catheter has a second occlusion member disposed at a distal end portion. A third catheter having a third occlusion member disposed at a distal end thereof is moveably disposable within a second lumen of the second catheter. The second catheter has a side port in fluid communication with the second lumen such that the third catheter can be extended out of the second lumen through the side port. The first occlusion member, the second occlusion member and the third occlusion member can collectively be used to isolate a target region within a patient including a portion of a first body lumen and a portion of a second body lumen. One of the first catheter and the second catheter defines an infusion lumen in fluid communication with an infusion port that can be used to communicate a therapeutic material to the isolated target region.

BRIEF DESCRIPTION OF THE DRAWINGS

FIGS. 6-11 are each a cross-sectional view of a different portion of the multi-occlusion catheter insertion device of FIG. 4, taken along lines 6-6, 7-7, 8-8, 9-9, 10-10, and 11-11, respectively, in FIG. 5.

FIG. 12 is a side view of a multi-occlusion catheter insertion device according to an embodiment.

FIGS. 14-19 are each a cross-sectional view of a different portion of the multi-occlusion catheter insertion device taken along lines 14-14, 15-15, 16-16, 17-17, 18-18, and 19-19, respectively, in FIG. 13.

FIG. 33 is a side view of a catheter system, according to an embodiment, shown deployed within a main vessel and a side branch of the main vessel.

FIG. 42 is a side view of a catheter system, according to another embodiment, shown deployed within a bifurcated vessel.

FIG. 43 is a cross-sectional view taken along line 43-43 in FIG. 42.

FIGS. 46, 47 and 48 are each a side view of a portion of a catheter system, according to a different embodiment, shown deployed within a main vessel and a side branch of the main vessel.

DETAILED DESCRIPTION

Figure 1:
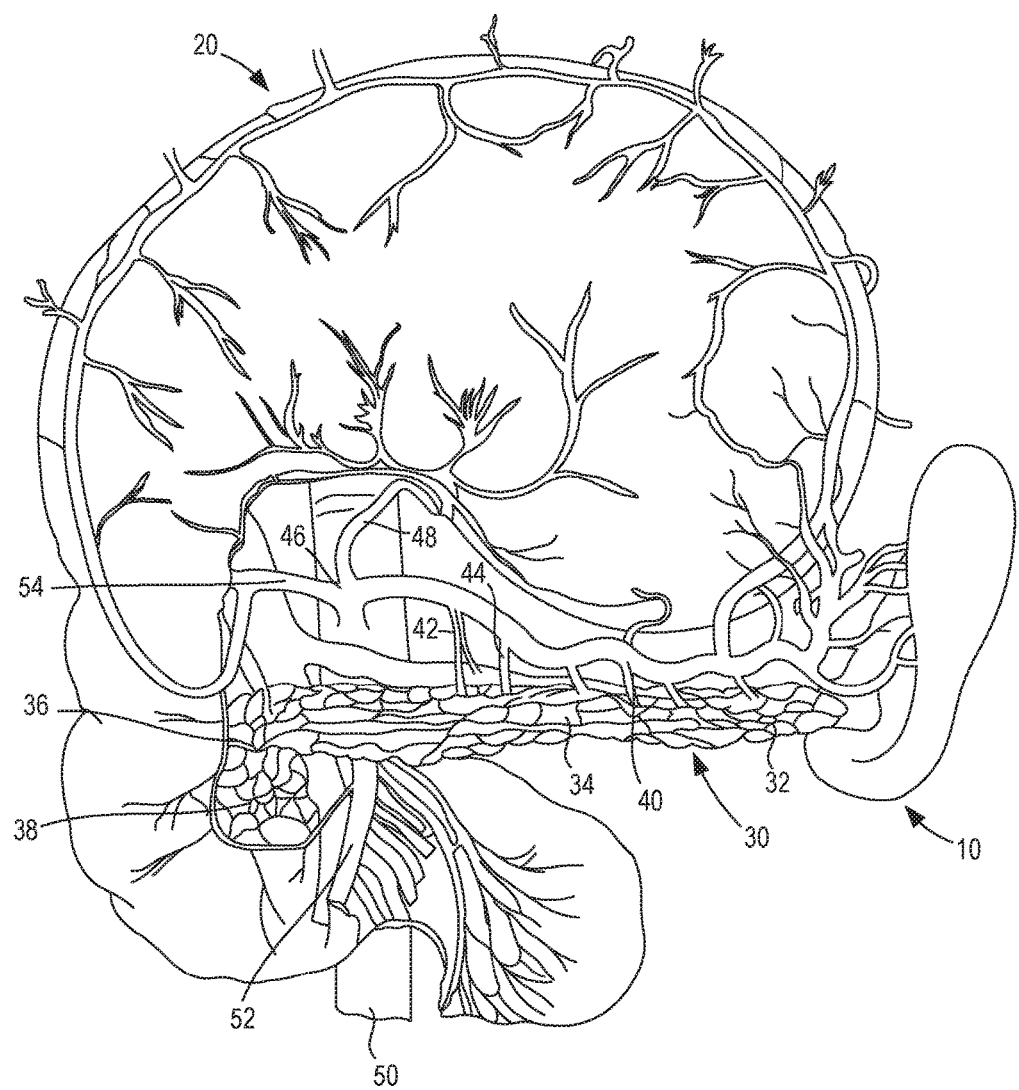
FIG. 1 is an illustration of a pancreas and related structure in a human.

Devices and methods are described herein that can be used to deliver a drug or other treatment therapy to a segment of an artery where there is a side branch which may act as an escape route for localized treatment agents (e.g., chemotherapy). A catheter device is described herein that can be used to occlude a main artery or vessel and a secondary treatment catheter can be inserted through the catheter device and used to occlude such a side branch extending from the main artery or vessel. With the main artery and side branch occluded, a therapeutic agent can then be injected into the main artery using the catheter device, and the therapeutic agent can be diffused through the walls of the artery and to, for example, a target tumor to be treated.

In some embodiments, the secondary treatment device includes an occlusion member, such as an expandable balloon occlusion member, that can be deployed temporarily to occlude the side branch. In other embodiments, the secondary treatment device can include a catheter configured to deliver or deploy a permanent occlusion member such as a coil or plug to the side branch. A catheter as described herein can be inserted into an artery and directed to an area of interest where it can be used to occlude the area of interest. In other embodiments, a secondary treatment catheter can be inserted into the side branch and used to infuse a treatment agent into the side branch.

Devices and methods are described herein that can be used to isolate a portion of a first body lumen and a portion of a second body lumen. For example, the first body lumen can be a main vessel and the second body lumen can be a side branch of the main vessel. A first catheter having two occlusion members can be disposed in the first body lumen and a second catheter having a third occlusion member can be inserted through a lumen of the first catheter, out a side port of the first catheter and disposed within the second body lumen. The third occlusion member can be deployed to occlude a portion of the second body lumen. Thus, the two occlusion members of the first catheter and the third occlusion member can collectively define a target isolated region to be treated that spans between the first body lumen and the second body lumen. In some embodiments, the first catheter can include an infusion port that can be used to communicate a therapeutic material (e.g., biologic, cell, agent, drug formulation, etc.) into the isolated region. The infusion port can be disposed on the first catheter between the two occlusion members and the side port through which the second catheter can be extended from can be disposed between the infusion port and the proximal most occlusion member on the first catheter.

In some embodiments, a catheter assembly includes a first catheter movably disposed within a first lumen of a second catheter. The first catheter has a first occlusion member disposed at a distal end portion and the second catheter has a second occlusion member disposed at a distal end portion. A third catheter having a third occlusion member disposed at a distal end thereof is moveably disposable within a second lumen of the second catheter. The second catheter has a side port in fluid communication with the second lumen such that the third catheter can be extended out of the second lumen through the side port. The first occlusion member, the second occlusion member and the third occlusion member can collectively be used to isolate a target region within a patient including a portion of a first body lumen and a portion of a second lumen. One of the first catheter and the second catheter defines an infusion lumen in fluid communication with an infusion port that can be used to communicate a therapeutic material to the isolated target region.

In some embodiments, an apparatus includes a catheter assembly having a first occlusion member and a second occlusion member disposed thereon at a non-zero distance from each other. The catheter assembly defines a first lumen in fluid communication with a side port disposed between the first occlusion member and the second occlusion member. A secondary catheter having a third occlusion member disposed at a distal end portion thereof, is movably disposable within the first lumen of the first catheter and configured to exit the side port. The secondary catheter defines an infusion lumen in fluid communication with an infusion port. The first occlusion member, the second occlusion member and the third occlusion member collectively configured to define an isolated target region within a patient including a portion of a first body lumen and a portion of a second body lumen. The infusion lumen and the infusion port configured to communicate a therapeutic material into the isolated target region.

In some embodiments, an apparatus includes a catheter device that includes a first occlusion member disposed at a distal end portion thereof and a second occlusion member disposed proximally of the first occlusion member and at a spaced distance from the first occlusion member. The catheter device defines a first lumen in fluid communication with a first side port, and a second lumen in fluid communication with a second side port. The catheter device configured to be inserted into an artery with the first occlusion member and the second occlusion member each in a collapsed configuration. The first occlusion member and the second occlusion member are each movable to an expanded configuration within the artery to define an isolated segment of the artery. The first lumen and the first side port configured to communicate a treatment material to the isolated segment of the artery. The second lumen and the second side port configured to receive a treatment device that can be disposed out through the second side port and into a side branch in fluid communication with the artery.

In some embodiments, a method includes inserting into an artery, a catheter device having a first occlusion member disposed at a distal end portion thereof and a second occlusion member disposed proximally of the first occlusion member and at a spaced distance from the first occlusion member, the catheter device defining a first lumen in fluid communication with a first side port, and a second lumen in fluid communication with a second side port. The first occlusion member and the second occlusion member each being in a collapsed configuration when the catheter device is inserted into the artery. The first occlusion member and the second occlusion member are each moved to an expanded configuration within the artery to define an isolated segment of the artery. A treatment device is inserted through the second lumen and out the second side port and into a side branch in fluid communication with the artery. In some embodiments, the treatment device includes a third occlusion member and the method further includes the side branch with the third occlusion member such that a treatment region is collectively defined by the isolated segment of the artery and a portion of the side branch between the artery and the third occlusion member. In some embodiments, the method includes introducing a coil device into the side branch using the treatment catheter to permanently occlude the side branch.

In some embodiments, a system and/or device(s) is provided for endovascular introduction of therapeutic biologics, cells, or other treatment materials/agents selectively to one or more target vessels for treatment of a variety of different afflictions and malformations (e.g., cancer). In some embodiments, a device and/or system can include, for example, an inner catheter having a distal retractable occlusion element and an inner catheter lumen adapted and configured to introduce a guidewire, and an outer catheter having a distal retractable occlusion element, an infusion lumen adapted and configured to introduce a therapeutic agent into one or more target vessels, and a lumen for slidably receiving the inner catheter. In such an embodiment, the distal retractable occlusion element of the outer catheter can be positioned proximal to the distal retractable occlusion element of the inner catheter; and a sealing element can be included that is configured to selectively isolate or seal an end of the outer catheter to prevent therapeutic agent from entering into the lumen of the outer catheter in which the inner catheter is slidably disposed.

In some embodiments, occlusion elements described herein can be used to isolate a targeted region of the tail or body of the pancreas. In some embodiments, the infusion lumen of the outer catheter can further be configured to allow atraumatic introduction of biologics or cells, such as stem cells, into the isolated region. The infusion lumen can also be configured to allow rapid infusion of biologics or cells without causing damage to the cells during the infusion process. In some embodiments, the devices and methods described herein can be used for isolating the perfusion area of the pancreas or other organs for introduction of chemotherapy treatment of, for example, cancer or other therapeutic agents targeted to the organ.

In some embodiments, a selective sealing element can include, for example, a ring, a membrane, or any other suitable element configured to prevent loss of cells into the lumen of the outer catheter in which the inner catheter is disposed to maximize engraftment efficiency. The lumen provided in the inner catheter can be configured to perfuse a distal organ beyond the targeted isolation region of the artery.

In some embodiments, a distance between the proximal retractable occlusion element and the selective sealing element can be configured for external adjustment, thus allowing a user to customize the isolated area (between the two occlusion elements) to better target the tail or body of the pancreas during delivery of biologics. The proximal retractable occlusion element and the selective sealing element can have a cross-sectional diameter, for example, between 2-12 mm.

In some embodiments, devices and methods described herein can be used for occlusion of a vessel segment. For example, a catheter device as described herein can be percutaneously introduced via a femoral artery and fluoroscopically guided to a splenic artery. An area or region of the pancreatic branches of the splenic artery can be isolated and a dye marker can be introduced that can demarcate where perfusion in the pancreatic tissue has occurred. The devices and methods described herein can perfuse the pancreatic tissue without perfusion of the surrounding organs such as the spleen and stomach. Further, the perfusion can occur with no back flush inside the lumen of the outer catheter in which the inner catheter is slidably disposed.

As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used herein, the term "set" can refer to multiple features or a singular feature with multiple parts. For example, when referring to a set of ports, the set of ports can refer to a single port or to multiple ports.

As used herein, the words "proximal" and "distal" refer to a direction closer to and away from, respectively, an operator of, for example, a medical device. Thus, for example, the end of the medical device closest to the patient's body (e.g., contacting the patient's body or disposed within the patient's body) would be the distal end of the medical device, while the end opposite the distal end and closest to, for example, the user of the medical device, would be the proximal end of the medical device. Said another way, the distal end portion is the end that is located furthest from a point of reference, such as an origin or a point of attachment. For example, the distal end portion would be the end farthest away from a user's hand. The proximal end portion, thus, would be the position nearer to a point of reference such as an origin, i.e., the user's hand.

Components of the embodiments described herein can be formed or constructed of one or more biocompatible materials. Examples of suitable biocompatible materials include metals, glasses, ceramics, or polymers. Examples of suitable metals include pharmaceutical grade stainless steel, gold, titanium, nickel, iron, platinum, tin, chromium, copper, and/or alloys thereof. A polymer material may be biodegradable or non-biodegradable. Examples of suitable biodegradable polymers include polylactides, polyglycolides, polylactide-co-glycolides (PLGA), polyanhydrides, polyorthoesters, polyetheresters, polycaprolactones, polyesteramides, poly(butyric acid), poly(valeric acid), polyurethanes, and/or blends and copolymers thereof. Examples of non-biodegradable polymers include nylons, polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, and/or blends and copolymers thereof.

Although some of the example embodiments described herein are directed for use in the treatment of a pancreas, it should be understood that the catheter systems and devices described herein can be used in other areas and organs within the body. For example, the catheter systems and devices can be used in cardiac arteries and vessels.

FIG. 1 illustrates the spleen 10, the stomach 20, and the pancreas 30 situated within an abdominal cavity (not shown) of a mammal (e.g., a human). The pancreas 30 is a gland organ which is part of the digestive and endocrine system of vertebrates. The pancreas 30 is both an endocrine gland producing hormones, including insulin, glucagon, and somatostatin, as well as an exocrine gland, secreting pancreatic juice containing digestive enzymes that pass to the small intestine. These enzymes help in the further breakdown of the carbohydrates, protein, and fat in the chyme.

As shown, the pancreas 30 has a tail 32, a body 34, a neck 36, and a head 38. Arterially, the pancreas 30 is accessed by the splenic artery 40, which originates from the abdominal aorta 50. The splenic artery 40 includes four segments, namely, a peripancreatic segment, a pancreatic segment, a perihilar segment, and a hilar segment. Generally, there is wide variability to the length of the total artery and each respective segment. There is also variation in the actual location and presence of major branches of the splenic artery 40 supplying the pancreatic parenchyma (e.g., the function parts of the pancreas 30). For example, the dorsal pancreatic artery 42 is the major branch supplying the pancreatic body 34 that arises from the pancreatic and peripancreatic portion of the splenic artery 40. The pancreatic magnum artery 44 (also referred to as the great pancreatic artery or greater pancreatic artery) is the largest blood vessel that arises from the peripancreatic segment of the splenic artery 40 to supply oxygenated blood to an anterior portion of the pancreatic tail 32. These two arteries form an arch anastomosis in the pancreas. However, there is variability in the origination of both arteries. For example, the dorsal pancreatic artery 42 generally arises from the celiac trunk (artery) 46 and or splenic artery 40 but can also arise from the superior mesenteric artery 52. The pancreatic magnum artery 44 commonly branches from the splenic artery 40 but can branch from a variety of locations along approximately a 15 centimeter (cm) length of the splenic artery 40 spanning from a proximal end to a distal end. Furthermore, each of these arteries can, in turn, have multiple branches/takeoffs that arise therefrom.

In the course of the pancreatic portion of the splenic artery 40, other arteries arise therefrom that supply other organs including, for example, the accessory left gastric artery 48, which supplies blood to the stomach and subsequently, the arteries supplying the spleen. Due to the anatomical variability in the individual arteries as described above, systems used to intra-arterially access, for example, the pancreas can be configured to provide visualization of the common branches in this area and flexibility in the isolated distance to allow for the individual variation in the origin and/or the multiple possible takeoffs of the dorsal pancreatic artery 42 and/or the pancreatic magnum artery 44. Additionally, devices can be adapted to enable delivery of a target biologic, such as insulin producing beta cells, and autologous stem cells (mesenchymal, bone marrow, and others). Beta cells are a type of cell in the pancreas in areas called the islets of Langerhans. Beta cells make and release insulin.

Figure 2:
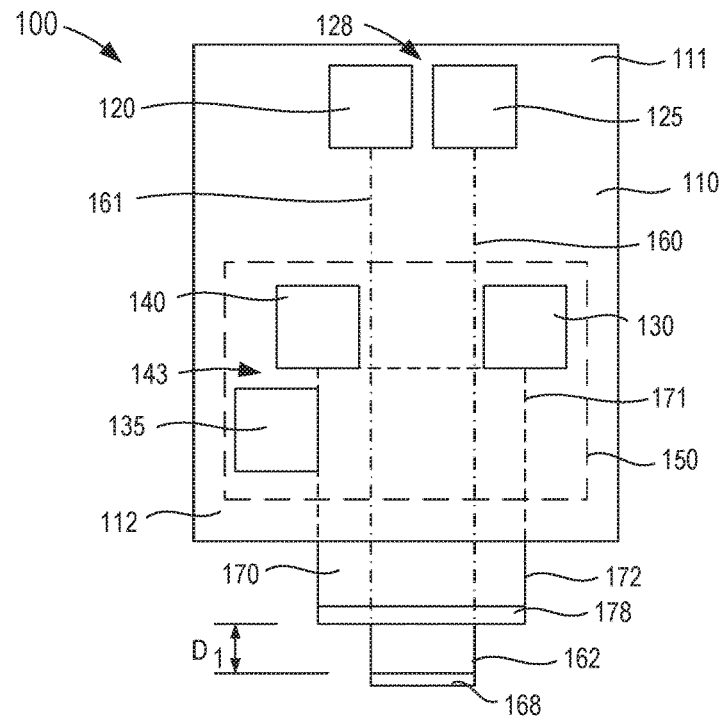
FIGS. 2 and 3 are schematic illustrations of a multi-occlusion catheter insertion device according to an embodiment, in a first configuration and a second configuration, respectively.
Figure 3:
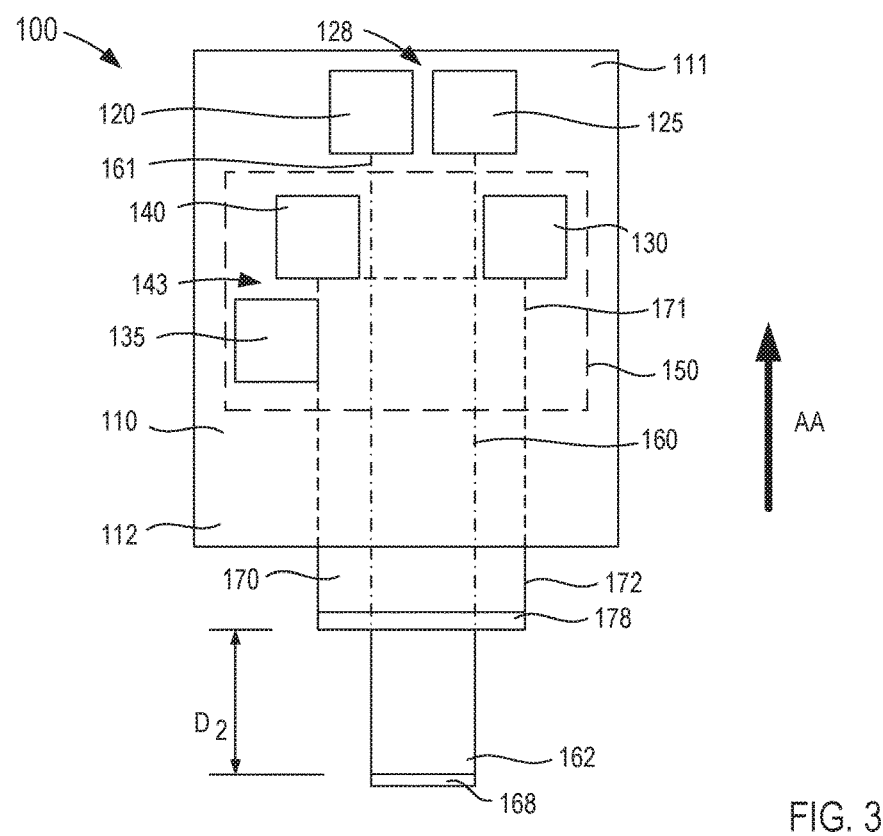

FIGS. 2 and 3 are schematic illustrations of a multi-occlusion catheter insertion device 100 according to an embodiment, in a first configuration and a second configuration, respectively. The multi-occlusion catheter insertion device 100 (also referred to herein as "device") can be arranged to allow for substantially single handed use to, for example, isolate a segment of a bodily lumen such as an artery of the pancreas, thereby allowing a procedure to be performed within the isolated segment and/or allowing a targeted delivery of a biological or therapeutic agent. The device 100 includes a handle 110, an actuator 150, a first catheter 160, and a second catheter 170. The handle 110 can be any suitable shape, size, or configuration. For example, in some embodiments, the handle 110 can have a shape and size that are configured to enhance the ergonomics of the device 100. As described in further detail herein, the handle 110 can be grasped by a user (e.g., a doctor, physician, surgeon, technician, etc.) to insert a portion of the first catheter 160 and a portion of the second catheter 170 into a bodily lumen of a patient and can be manipulated to move, inflate, deflate, adjust, and/or otherwise reconfigure the portion of the first catheter 160 and the portion of the second catheter 170 within the bodily lumen. For example, the second catheter 170 can be moved relative to the first catheter 160, or vice-versa, to adjust a distance between a first occlusion element 168 coupled to a distal end portion of the first catheter 160 and a second occlusion element 178 coupled to a distal end portion of the second catheter 170. The device 100 can be used to isolate a segment of a bodily lumen within the space defined between the first occlusion element 168 and the second occlusion element 178. Thus, a procedure can then be performed within the isolated segment such as for example, delivering a therapeutic agent to the isolated segment.

The handle 110 has a proximal end portion 111 and a distal end portion 112. As described in further detail herein, the handle 110 can be arranged to enclose, house, and/or be disposed about a portion of the first catheter 160 and the second catheter 170. For example, the first catheter 160 and the second catheter 170 can each be coupled to the handle 110. A first port 120 and a second port 125 (collectively referred to herein as a first set of ports 128) are each disposed at the proximal end portion 111 of the handle 110. The first port 120 and the second port 125 can each define a lumen (not shown in FIGS. 2 and 3). In some embodiments, the first port 120 and the second port 125 can be formed monolithically or integrally with the first catheter 160. The first port 120 and the second port 125 can be any suitable size, shape, or configuration. For example, in some embodiments, the first port 120 and the second port 125 can extend from the proximal end portion 111 of the housing 110 such that at least a portion of the first port 120 and the second port 125 is accessible outside of the handle 110. Although not shown in FIGS. 2 and 3, the first port 120 and the second port 125 can each be physically and fluidically coupled to a device, mechanism, and/or the like, such as, for example, a source of an inflation medium as described in more detail below. For example, in some embodiments, the first port 120 and the second port 125 can each include a Luer-Lok® or the like that can physically and fluidically couple the first port 120 and/or the second port 125 to such a device. As described in further detail herein, the first set of ports 128 can be in fluid communication with at least a portion of the first catheter 160 to place at least the portion of the first catheter 160 in fluid communication with a device (e.g., a source of an inflation medium) coupled to the handle 110 via the first port 120 and/or the second port 125. For example, the lumen of the first port 120 can be in fluid communication with a first lumen defined by the first catheter 160 and the lumen of the second port 125 can be in fluid communication with a second lumen defined by the first catheter 160.

The distal end portion 112 of the handle 110 includes a third port 130, a fourth port 135, and a fifth port 140 (collectively referred to herein as a second set of ports 143). The second set of ports 143 can be any suitable arrangement such as, for example, described above with reference to the first set of ports 128. For example, the third port 130, the fourth port 135, and the fifth port 140 can each define a lumen (not shown in FIGS. 2 and 3) and can each include a Luer-Lok® or the like that can physically and fluidically couple the third port 130, the fourth port 135, and/or the fifth port 140 to any suitable attachment, device, mechanism, and/or the like. For example, the third port 130, the fourth port 135, and/or the fifth port 140 can each be coupled to an external device such as a device supplying a therapeutic agent, a device supplying an inflation medium or a device supplying an irrigation solution as described in more detail below with reference to, for example, device 400. In some embodiments, the second set of ports 143 includes the fifth port 140 and only one of the third port 130 and the second port 135.

As described in further detail herein, the second set of ports 143 can be in fluid communication with at least a portion of the second catheter 170 to place at least the portion of the second catheter 170 in fluid communication with such external devices coupled to the handle 110 via the third port 130, the fourth port 135, and/or the fifth port 140. For example, the third port 130 and/or the fourth port 135 can be coupled to and in fluid communication with a first lumen defined by the second catheter 170, and the fifth port 140 can be coupled to and in fluid communication with a second lumen defined by the second catheter 170. In some embodiments, the third port 130, the fourth port 135, and/or the fifth port 140 can be monolithically or integrally formed with the second catheter 170. Moreover, the second set of ports 143 can be coupled to or operably coupled to the actuator 150 as described in more detail herein.

The first catheter 160 (also referred to herein as "inner catheter") and the second catheter 170 (also referred to herein as "outer catheter") can be any suitable catheter device. For example, in some embodiments, the first catheter 160 and the second catheter 170 are multi-lumen catheters. As shown in FIG. 2, the first catheter 160 has a proximal end portion 161 and a distal end portion 162. The proximal end portion 161 of the first catheter 160 is disposed within a portion of the handle 110. More specifically, the proximal end portion 161 of the first catheter 160 can be fixedly disposed within the portion of the handle 110 to place the first catheter 160 in fluid communication with one or more of the ports 120 and 125 of the first set of ports 128. In some embodiments, the first catheter 160 can define a first lumen that can be physically and fluidically coupled to the first port 120 and a second lumen that can be physically and fluidically coupled to the second port 125. In other embodiments, a first catheter can be coupled to the handle and can be operably coupled to a first port and a second port (e.g., ports 120, 125) via an intervening structure such as, for example, flexible tubing or the like. In this manner, the first port 120 can be placed in fluid communication with a first lumen (not shown in FIGS. 2 and 3) defined by the first catheter 160, as described in further detail herein. Similarly, the second port 125 can be placed in fluid communication with a second lumen (not shown in FIGS. 2 and 3) defined by the first catheter 160. In some embodiments, the second port 125 and the second lumen of the first catheter 160 can receive a guidewire or the like, as described in further detail herein.

The distal end portion 162 of the first catheter 160 extends beyond a distal end portion of the handle 110 and includes the occlusion member 168. The occlusion member 168 can be any suitable device or mechanism that is configured to selectively limit, block, obstruct, or otherwise occlude a bodily lumen (e.g., artery) in which the occlusion member 168 is disposed. For example, in some embodiments, the occlusion member 168 can be an inflatable balloon or the like that can be transitioned between a collapsed (e.g., deflated) configuration and an expanded (e.g., inflated) configuration. In some embodiments, the arrangement of the first catheter 160 and the handle 110 can be such that the first port 120 is in fluid communication with the occlusion member 168. Thus, in use, the first port 120 can be fluidically coupled to a device that can supply a pressurized fluid (e.g., air, inert gas, or liquid) to the occlusion member 168 to transition the occlusion member 168 between a collapsed configuration and an expanded configuration, as described in further detail herein.

The second catheter 170 of the device 100 has a proximal end portion 171 and a distal end portion 172. As shown in FIGS. 2 and 3, the second catheter 170 is movably disposed about a portion of the first catheter 160. More specifically, the second catheter 170 can be, for example, a multi-lumen catheter and can be arranged such that the first catheter 160 is movably disposed within a first lumen (not shown in FIGS. 2 and 3) defined by the second catheter 170. The proximal end portion 171 can be movably disposed within the handle 110 such that a portion of the second catheter 170 is in fluid communication with the second set of ports 143. In some embodiments, the second catheter 170 can be physically and fluidically coupled to the third port 130 and the fourth port 135, and/or the fifth port 140. In other embodiments, the second catheter can be disposed within a handle and can be operably coupled to one or more ports via an intervening structure such as, for example, flexible tubing or the like. In this manner, the third port 130 and/or the fourth port 135 can be placed in fluid communication with the second lumen (not shown in FIGS. 2 and 3) defined by the second catheter 170, as described in further detail herein; the fifth port 140 can be placed in fluid communication with a third lumen (not shown in FIGS. 2 and 3) defined by the second catheter 170, as described in further detail herein.

The distal end portion 172 of the first catheter 170 extends beyond a distal end portion of the handle 110 and includes an occlusion member 178. The occlusion member 178 can be any suitable device or mechanism that is configured to selectively limit, block, obstruct, or otherwise occlude a lumen (e.g., artery) in which the occlusion member 178 is disposed. For example, in some embodiments, the occlusion member 178 can be substantially similar to the occlusion member 168 of the first catheter 160. In some embodiments, the arrangement of the second catheter 170 and the handle 110 can be such that the third port 130 and/or the fourth port 135 is in fluid communication with the occlusion member 178. Thus, in use, the third port 130 and/or the fourth port 135 can be fluidically coupled to a device that can supply a pressurized fluid (e.g., air, inert gas, or liquid) to the occlusion member 178 to transition the occlusion member 178 between a collapsed configuration and an expanded configuration, as described in further detail herein. In some embodiments, at least a portion of the occlusion member 178 can be selectively permeable to allow a biological agent to pass therethrough. Although not shown in FIGS. 2 and 3, in some embodiments, the distal end portion 172 of the second catheter 170 can define one or more openings. In such embodiments, the fifth port 140 can be fluidically coupled to a device that can supply irrigation, therapeutic material or agents, biological agents, and/or the like to a volume or region disposed between the occlusion member 168 of the first catheter 160 and the occlusion member 178 of the second catheter 170.

As described above, the actuator 150 of the device 100 can be operably coupled to the second set of ports 143. For example, in some embodiments, the actuator 150 is included in and/or coupled to the handle 110 and arranged relative to the second set of ports 143 to be operably coupled thereto. The actuator 150 can be any suitable device, mechanism, assembly, etc. that is movable between a first position relative to the handle 110, associated with the device 100 in the first configuration (FIG. 2), and a second position relative to the handle 110, associated with the device 100 in the second configuration (FIG. 3). Furthermore, with the actuator 150 operably coupled to the second set of ports 143, the actuator 150 can be operable in moving the second set of ports 143 between a first position relative to the handle 110 (e.g., the distal position) and a second position relative to the handle 110 (e.g., the proximal position), as indicated by the arrow AA in FIG. 3. Thus, when the second catheter 170 is coupled to the second set of ports 143, the actuator 150 can also move the second catheter 170 relative to the handle 110 and/or relative to the first catheter 160 as described in more detail below.

In some embodiments, the actuator 150 can be a push or pull slide that can move within a track (not shown in FIGS. 2 and 3) defined by the handle 110. In other embodiments, the actuator 150 can be coupled to an energy storage device (e.g., a spring, compressed gas, etc.) that is configured to move the actuator 150. For example, the actuator 150 can include a push button that allows a spring to transition from a compressed configuration towards an uncompressed configuration to move the actuator 150 relative to the handle 110. In other embodiments, a portion of the actuator 150 can be rotated to move the actuator 150 between its first position and its second position relative to the handle 110. With the second catheter 170 physically and fluidically coupled to the second set of ports 143 (as described above), the movement of the actuator 150 can move the second catheter 170 relative to the handle 110. More specifically, the proximal end portion 171 of the second catheter 170 can be movably disposed within the handle 110 (as described above) such that when the actuator 150 is moved from its first position to its second position, the proximal end portion 171 of the second catheter 170 is moved from a first position relative to the handle 110 (e.g., FIG. 2) to a second position relative to the handle 110 (e.g., FIG. 3).

With the second catheter 170 movably disposed about the first catheter 160, the movement of the actuator 150 moves the second catheter 170 relative to the first catheter 160. For example, when the device 100 is in the first configuration, a first distance $D_1$ is defined between the occlusion member 168 of the first catheter 160 and the occlusion member 178 of the second catheter 170. Therefore, with the first catheter 160 fixedly disposed within the handle 110, the movement of the second catheter 170 in the proximal direction (e.g., the AA direction) increases the distance between the occlusion member 168 of the first catheter 160 and the occlusion member 178 of the second catheter 170 to a second distance $D_2$, as shown in FIG. 3.

In use, a guidewire (not shown) can be inserted into the second port 125 and through a lumen defined by the first catheter 160. In this manner, the guidewire can be advanced through a bodily lumen and the device 100 can be manipulated to advance the first catheter 160 along the guidewire to place the distal end portion 162 of the first catheter 160 and the distal end portion 172 of the second catheter 170 at a target location within the bodily lumen. Once at the target location, the actuator 150 can be moved in the AA direction (e.g., the proximal direction) to define a desired distance between the occlusion member 168 of the first catheter 160 and the occlusion member 178 of the second catheter 170, thereby placing the device 100 in the second configuration (FIG. 3). As described above, an inflation source can be coupled to the second port 125 of the first catheter 160 and the same inflation source or a second inflation source can be coupled to the third port 130 and/or the fourth port 135 of the second catheter 170. With the desired distance defined between the occlusion members 168 and 178, the inflation source(s) can be used to inflate the occlusion members 168 and 178. Thus, the occlusion members 168 and 178 can be transitioned from the collapsed (e.g., deflated) configuration to the expanded (e.g., inflated) configuration to substantially isolate a segment of the bodily lumen disposed therebetween. With the occlusion members 168 and 178 substantially occluding the bodily lumen, a biological or therapeutic agent can be delivered to the substantially isolated segment via the fourth port 135. For example, the biological or therapeutic agent can be delivered through the fourth port 135 into a lumen of the second catheter that is in fluid communication with the opening (see, e.g., opening 479 in FIG. 20) defined by the distal end portion 172 of the second catheter 170. In some instances, the substantially isolated segment can be irrigated by coupling an irrigation source to the fifth port 140. Thus, the irrigation is delivered to the substantially isolated segment via the opening (described above) defined by the distal end portion 172 of the second catheter 170.

Figure 4:
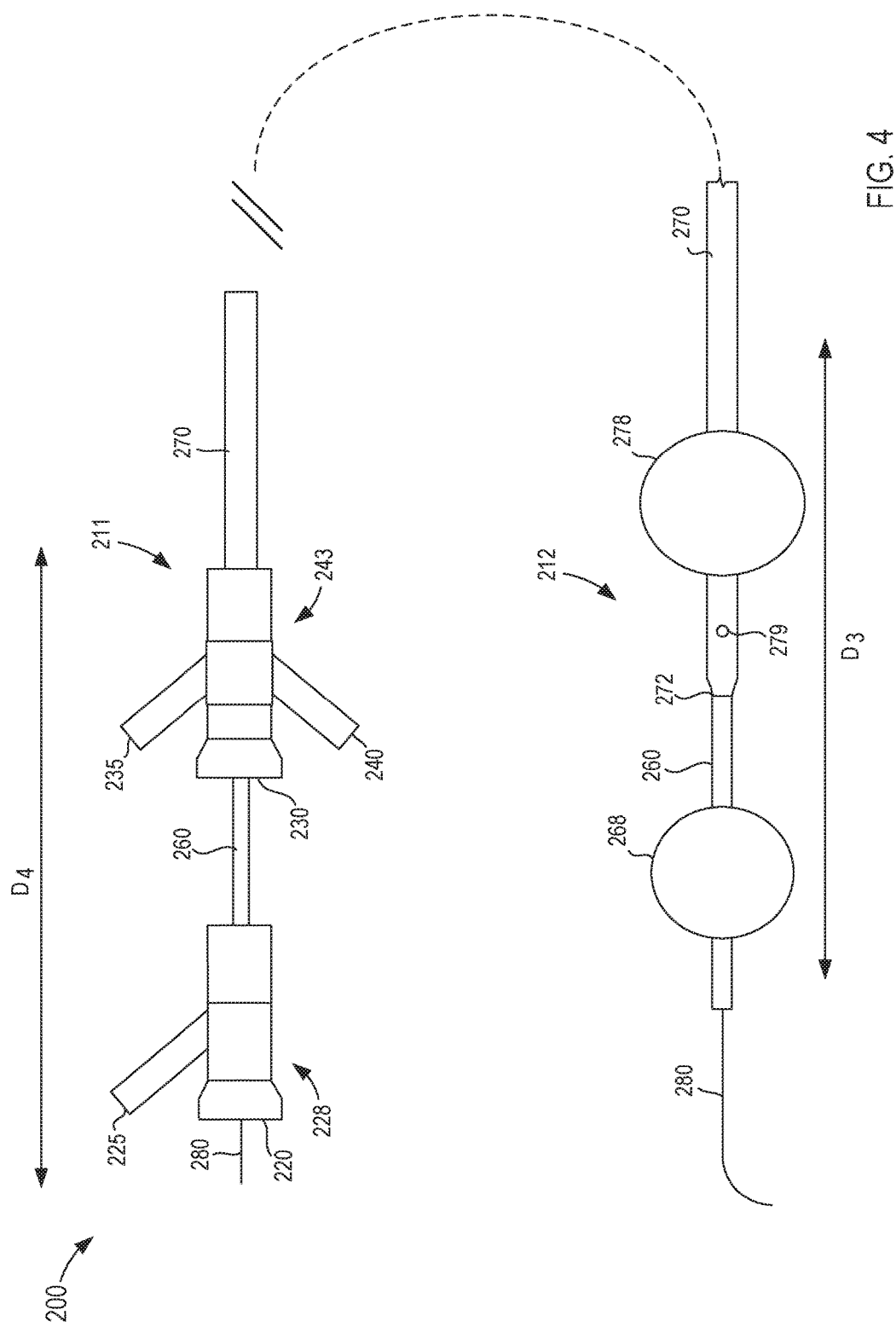
FIG. 4 is a side view of a multi-occlusion catheter insertion device according to an embodiment, shown in a dilated configuration.

FIGS. 4-11 illustrate a dilation catheter 200 according to an embodiment. FIG. 4 is a side view of the dilation catheter device 200 (also referred to herein as "catheter device"). In this embodiment, dilatation of two balloons is used to occlude a desired length of an artery such as, for example, the splenic artery 40 (see, e.g., FIG. 2). Specifically, the catheter device 200 includes a first catheter 260 (also referred to herein as "inner catheter") and a second catheter 270 (also referred to herein as "outer catheter"), a first Y-adaptor 228 (also referred to herein as "first set of ports") and a second Y-adaptor 243 (also referred to herein as "second set of ports"), a first occlusion element 268 (also referred to herein as "dilation element", "occluder," or "distal occlusion element"), and a second occlusion element 278 (also referred to herein as "dilation element", "occluder," or "proximal occlusion element") each configured to occlude a portion of an artery. The first occlusion element 268 is coupled to the first catheter 260 and the second occlusion element 278 is coupled to the second catheter 270.

The occlusion elements 268 and 278 can each be moved between a collapsed configuration (also referred to as "retracted configuration") for insertion of the catheter device 200 into a body of a patient (e.g., into an artery) and an expanded configuration (also referred to as "dilated configuration" or "inflated configuration") for occluding a portion of an artery. The occlusion elements 268 and 278 when in the collapsed configuration have a smaller outer perimeter (or diameter) than when in the expanded configuration.

The catheter device 200 includes a distal end portion 212 and a proximal end portion 211. In this embodiment, the occlusion elements 268 and 278 are expandable balloons coupled to an outer surface of the first catheter 260 and an outer surface of the second catheter 270, respectively, and are disposed at the distal end portion 212 of the catheter device 200. The catheter device 200 is shown in a dilated configuration in FIG. 4 with the occlusion elements 268 and 278 (i.e., balloons) in their expanded configuration (i.e., inflated, dilated).

Figure 5:
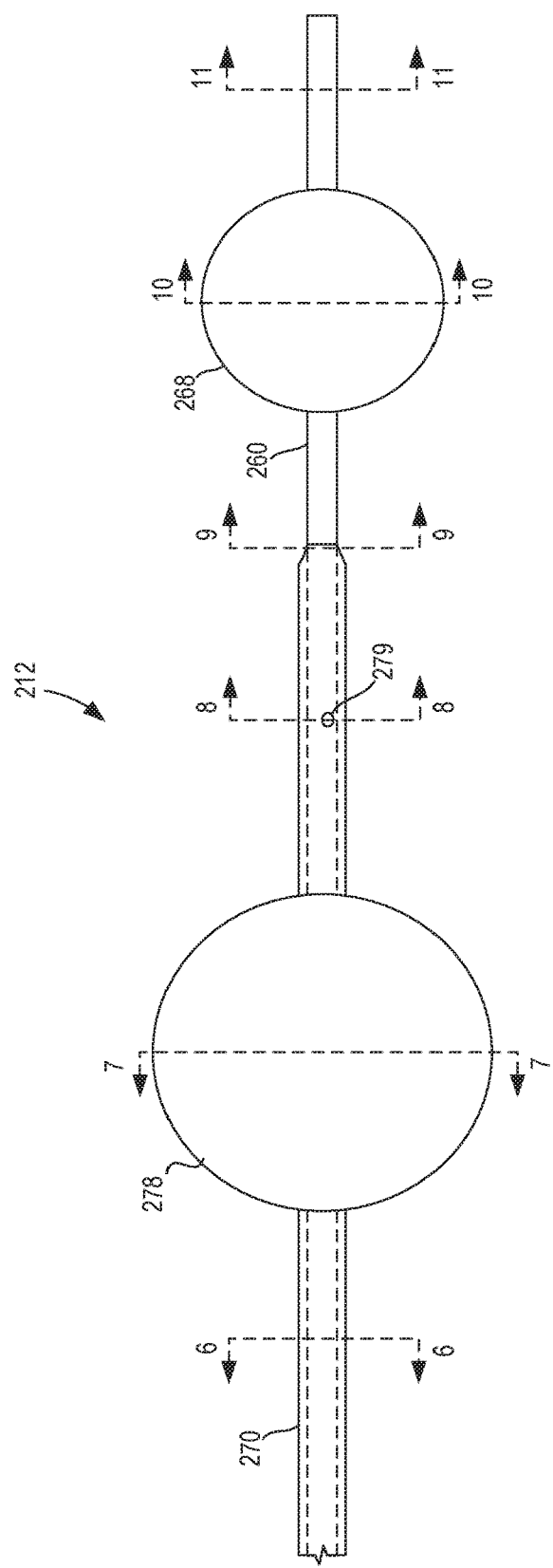
FIG. 5 is a side view of a portion of the multi-occlusion catheter insertion device of FIG. 4.

FIG. 5 is a side view of the distal end portion 212 of the catheter device 200 (e.g., a distal end portion of the first catheter 260 and the second catheter 270) and FIGS. 6-11 illustrate cross-sections at various locations along the distal end portion 212 of the catheter device 200 to illustrate the various lumens of the catheter device 200. As shown in FIGS. 6-11, the first catheter 260 defines a first lumen 265 and a second lumen 263 that each can extend a length of the first catheter 260. The first lumen 265 can be configured to receive a guidewire 280 (shown, for example, in FIG. 4). The second lumen 263 can be used to communicate an inflation medium to and from the first occlusion element 268 via an aperture 264 in fluid communication with the first occlusion element 268 (see, e.g., FIG. 10).

As shown, for example, in FIGS. 6 and 7, the second catheter 270 defines a first lumen 273, a second lumen 274, and a third lumen 276. The first lumen 273 can be used to communicate an inflation medium to and from the second occlusion element 278 via an aperture 275 in fluid communication with the second occlusion element 278 (see, e.g., FIG. 7). The second lumen 274 is configured to slidably receive at least a portion of the first catheter 260 therethrough, as shown in FIGS. 6-9. The third lumen 276 can terminate and be in fluid communication with an infusion aperture 279 near a distal end 272 of the second catheter 270 (see, e.g., FIG. 8). The infusion aperture 279 can be used to communicate a cell/biological/therapeutic material to a desired location within a body/artery of a patient.

The first Y-adaptor 228 is coupled to the first catheter 260 and includes two ports 220 and 225, as shown in FIG. 4. The port 220 defines a lumen (not shown) that is in fluid communication with the first lumen 263 of the catheter 260 and can be used to communicate an inflation medium to the first occlusion element 268 through the second lumen 263. For example, a source of an inflation medium (not shown) can be coupled to the catheter device 200 via the port 220 of the first Y-adaptor 228. The port 225 defines a lumen (not shown) that is in fluid communication with the second lumen 265 of the first catheter 260 (see, e.g., FIGS. 6-11) and can be used for introduction of the guidewire 280 into the second lumen 265.

The second Y-adapter 243 is coupled to the second catheter 270 and includes three ports 230, 235 and 240, as shown in FIG. 4. The port 230 defines a lumen (not shown) that is in fluid communication with the first lumen 273 of the second catheter 270 (see, e.g., FIGS. 6-11) and can receive the first catheter 260 therethrough. The port 235 defines a lumen (not shown) that is in fluid communication with the second lumen 274 of the second catheter 270 and can be used to communicate an inflation medium to and from the second occlusion element 278 in a similar manner as described above for port 225 and lumen 263. The port 240 defines a lumen (not shown) that is in fluid communication with the third lumen 276 of the second catheter 270 (see e.g., FIG. 6-11) and can be used to introduce cells/biological/therapeutic materials into and through the third lumen 276 and out through the infusion aperture 279.

The catheter device 200 can also include a seal element 285 (see, e.g., FIG. 9) (also referred to a as a "seal", "sealing element", "selective sealing element", or "filter-ring") disposed at or near a distal end 272 of the second catheter 270. The seal element 285 can prevent the entry of cells and or biologics that have been injected into an artery from flowing back into the lumen 273. By doing so, a maximum number of cells can be delivered to the treatment area, and improve engraftment efficiency. The seal element 285 can be for example, a ring, a membrane or other known sealing elements used in medical devices.

The slidable coupling of the first catheter 260 within the first lumen 273 of the second catheter 270 allows a collective length of the first catheter 260 and the second catheter 270 to be adjusted by slidably moving the first catheter 260 and the second catheter 270 relative to each other. Because the first occlusion element 268 is coupled to the first catheter 260 and the second occlusion element 278 is coupled to the second catheter 270, the slidable adjustment of the first catheter 260 and the second catheter 270 can thus allow adjustment of a distance between the second occlusion element 278 and the first occlusion element 268. The first lumen 273 of the second catheter 270 can be sized to receive the first catheter 260 with sufficient clearance to allow for ease of sliding/adjustment.

In use, the catheter device 200 can be placed at a desired location within an artery, such as for example, within a splenic artery 40 (see e.g., FIG. 1) and used to infuse a cell/biological material to a pancreas 30. A length of the first catheter 260 and the second catheter 270 can be adjusted such that a selected portion (e.g., a pancreatic portion) of the splenic artery 40 is isolated between the first occlusion element 268 and the second occlusion element 278. A cell/biologic material can be injected through the catheter device 200 and into the isolated region of the splenic artery 40.

The infusion of a cell/biological agent can occur in the localized region surrounding the isolated region or segment of vessel 40. In some instances, however, the presence of one or more additional, side-branching vessels forming a flow-restricting configuration in the isolated region of vessel 40 can allow infusion to occur in a larger semi-localized region. To allow the operator to accommodate the location of these side branches to fall within the isolated region, the first catheter 260 can be configured such that it is slidably associated with the second catheter 270 and the space between (e.g., distance between) occlusion elements 268 and 278 can be varied according to the circumstances of the desired treatment. The positioning of the distal occlusion element 268 within an artery can be individualized based on the specific anatomy to allow an enclosed or isolated area between the two occlusion elements 268 and 278 with a linear length ranging, for example, from 3 cm to 22 cm.

The cells targeted to the pancreas 30 (see e.g., FIG. 1) can be infused through infusion port 240, traverse through the third lumen 276, and exit through the infusion aperture 279 into the area isolated between the two occlusion elements 268 and 278. The catheter device 200 can be configured to enable delivery of target cells, such as insulin producing beta cells, and autologous stem cells (mesenchymal, bone marrow, and others) to blood vessels in communication with the pancreas in situ. The infusion pressure in the isolated blood vessel region can be measured with pressure monitoring through the infusion lumen of the catheter (with a monometer (not shown) in line with infusion port 279). The pressure in the third lumen 276 can be based on the size of the cells being delivered, on the flow rate, the viscosity of the solution, and/or flow resistance of the third lumen 276 of second catheter 270. The flow resistance of the catheter device 200 can in turn be determined based on, for example, the inner coating material, the size and the length of the third lumen 276, the size of the third port 240, and/or the size of the distal infusion aperture 279. The catheter device 200 can allow for rapid infusion of cells (e.g., up to 2 milliliter per second (ml/sec)). In some applications, the rapid infusion of cells can enhance uptake and eventual engraftment. Smaller aperture size (e.g., the infusion aperture 279), lumen size (e.g., the third lumen 276), and increased flow resistance may cause "sludging" of cells, leading to poor intra-arterial flow and diminished uptake. Lastly, the infusion aperture 279 and luminal design of the catheter device 200 can be configured to minimize risk of mechanical cell damage during the infusion process.

FIG. 12 illustrates an embodiment of a catheter device 300 that uses two filter elements, instead of expandable balloons to occlude and isolate the area of interest for infusion of cells or chemotherapeutic agents, without inhibiting the flow of plasma through the isolated area. The filter elements can be formed with, for example, a medical mesh material. The size of the pores of the filter elements can be, for example, about 2 microns (µm) or less in length, which can inhibit cells from passing through the filter element, but not impede serum/plasma and other components from passing through the filter element. The catheter device 300 can be used for the same or similar functions as described above for catheter device 200. For example, the catheter device 300 can be used for introduction of cells or other biologic or therapeutic material into a desired location within a patient's body, such as within a splenic artery.

The catheter device 300 includes a first catheter 360 and a second catheter 370 that can be slidably coupled together as described above for catheter device 200, a first Y-adaptor 328 (also referred to herein as "first set of ports") coupled to the first catheter 360, a second Y-adaptor 343 (also referred to herein as "second set of ports") coupled to the second catheter 370, a first occlusion element 368 (also referred to herein as "dilation element", "occluder", "distal occlusion element") and a second occlusion element 378 (also referred to herein as "dilation element", "occluder", "proximal occlusion element") to occlude a portion of an artery. The first occlusion element 368 is coupled to the first catheter 360 and the second occlusion element 378 is coupled to the second catheter 370.

In this embodiment, the occlusion elements 368 and 378 are filter elements that can be moved between a collapsed configuration (also referred to as "retracted configuration" or "closed configuration") for insertion of the catheter device 300 into a body of a patient (e.g., into an artery) and an expanded configuration (also referred to as "dilated configuration" or "open configuration"), as shown in FIG. 12, for occluding a portion of an artery. The occlusion elements 368 and 378 when in the collapsed configuration have a smaller outer perimeter (or diameter) than when in the expanded configuration.

Figure 13:
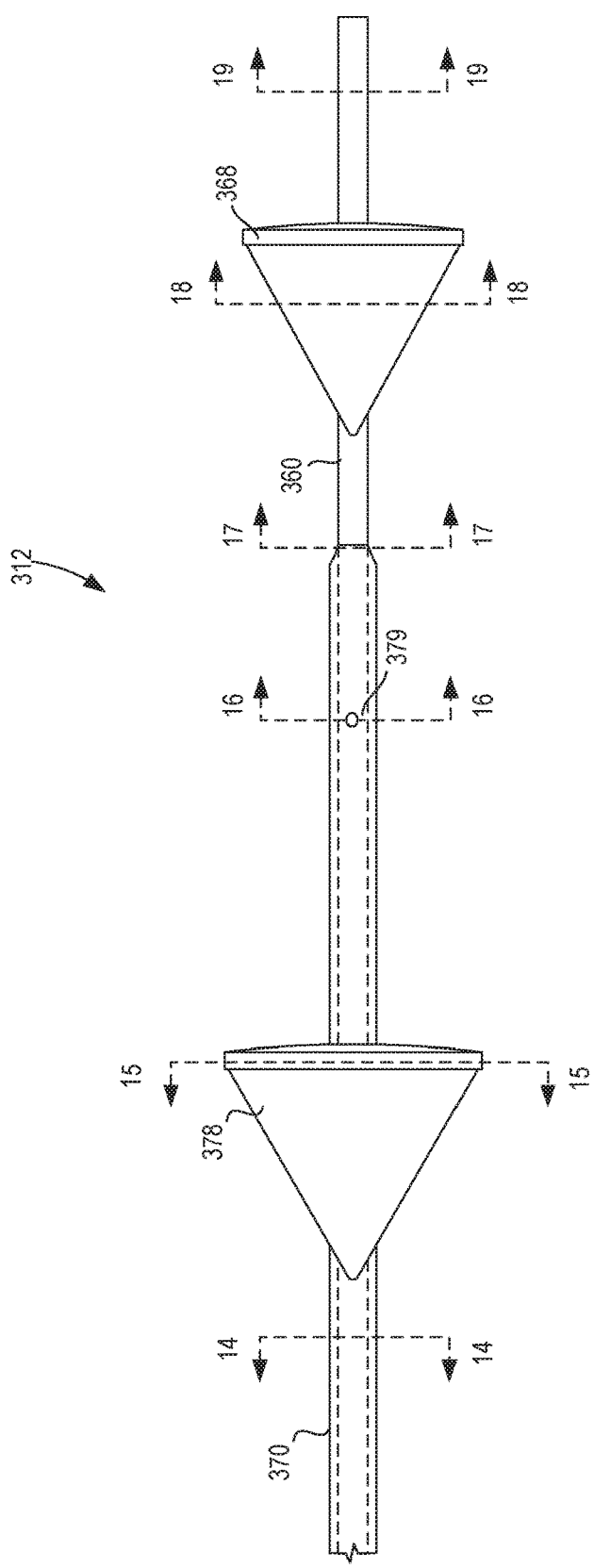
FIG. 13 is a side view of a portion of the multi-occlusion catheter insertion device of FIG. 12.

The catheter device 300 includes a distal end portion 312 and a proximal end portion 311. FIG. 13 is a side view of the distal end portion 312 of the catheter device 300 and FIGS. 14-19 illustrate cross-sections at various locations along the distal end portion 312 of the catheter device 300. As shown in FIGS. 14-19, the first catheter 360 defines a first lumen 363 and a second lumen 365 that each can extend a length of the first catheter 360. The first lumen 363 can be configured to receive a wire deployment device 382 that can be coupled to the filter element 368 and configured to move the filter element 368 from its expanded or open configuration and its collapsed or closed configuration. The second lumen 365 can be configured to receive a guidewire 380 (shown in FIG. 12).

The second catheter 370 defines a first lumen 373, a second lumen 374, and a third lumen 376. The first lumen 373 is configured to slidably receive at least a portion of the first catheter 360 therethrough. The second lumen 374 can be configured to receive a wire deployment device 381. The wire deployment device 381 can be coupled to the filter element 378 and used to move the filter element 378 between its expanded or open configuration and its collapsed or closed configuration. The third lumen 376 can terminate and be in fluid communication with an infusion aperture 379 (see, e.g., FIG. 16) near a distal end 372 of the second catheter 370. The infusion aperture 379 can be used to communicate, for example, a cell or cells (or other therapeutic or biologic material) to a desired location within a body of a patient.

The first Y-adaptor 328 includes a port 320 and a port 325 as shown in FIG. 12. The port 320 defines a lumen (not shown) that is in fluid communication with the first lumen 363 of the catheter 360. The port 325 defines a lumen (not shown) that is in fluid communication with the second lumen 365 of the catheter 360, and can be used for introduction of the guidewire 380 into the second lumen 365. The second Y-adapter 343 includes three ports 330, 335 and 340, as shown in FIG. 12. The port 330 defines a lumen (not shown) that is in fluid communication with the first lumen 373 of the second catheter 370 and can receive the first catheter 360 therethrough. The port 335 defines a lumen (not shown) that is in fluid communication with the second lumen 374 of the second catheter 370, and the port 335 defines a lumen (not shown) that is in fluid communication with the third lumen 376 of the second catheter 370.

The filter elements 368 and 378 can each be shaped as a cone when in their expanded or open configurations as shown in FIGS. 12 and 13. The filter elements 368 and 378 can each be sized when in their expanded or open configurations to meet the size of a particular vessel diameter in which the catheter device 300 is to be deployed. After infusion of cells or a therapeutic/biologic material through the catheter device 300, the filter elements 368 and 378 can be collapsed to a smaller size for removal of the catheter device 300 from the patient.

In some embodiments, a diameter of the occlusion elements (e.g., 268, 278, 368, and 378) when expanded within an artery, such as, for example, the splenic artery 40, can be adjustable to meet anatomical variations including a) individual variability in the size of the splenic artery 40 and b) end to end variation as the artery size can taper down between the two ends of the artery. As such, in some embodiments, to allow successful isolation of the area for treatment, the proximal occlusion element (e.g., the balloon 278 and/or the filter element 378) can be sized (e.g., have an outer diameter or outer perimeter) between, for example, 3-12 mm and the distal occlusion element (e.g., the balloon 268 and/or the filter element 368) between, for example, 3-12 mm. The proximal occlusion element can be larger than the distal occlusion element, smaller than the distal occlusion element, or the same size as the distal occlusion element.

Referring now to FIGS. 20-29, a multi-lumen catheter insertion device 400 is illustrated according to an embodiment. The multi-occlusion catheter insertion device 400 (also referred to herein as "catheter device" or "device") includes a handle 410, an actuator 450, a first catheter 460 (also referred to herein as "inner catheter"), and a second catheter 470 (also referred to herein as "outer catheter") and can be movable between a first configuration and a second configuration. As described in further detail herein, the device 400 can be grasped by a user (e.g., a doctor, physician, surgeon, technician, etc.) and manipulated substantially single handedly to insert a portion of the first catheter 460 and a portion of the second catheter 470 into a bodily lumen of a patient and to move, inflate, deflate, adjust, and/or otherwise reconfigure the portion of the first catheter 460 and the portion of the second catheter 470 within the bodily lumen. For example, the second catheter 470 can be moved relative to the first catheter 460, and vice-versa, to adjust a distance between a first occlusion element 468 coupled to a distal end portion of the first catheter 460 and a second occlusion element 478 coupled to a distal end portion of the second catheter 470. The device 400 can be used to isolate a segment of a bodily lumen within the space or region defined between the first occlusion element 468 and the second occlusion element 478. Thus, a procedure can then be performed within the isolated segment such as, for example, delivering a cell or a therapeutic/biological agent to the isolated segment.

The handle 410 of the device 400 can be any suitable shape, size, or configuration. For example, in some embodiments, the handle 410 can have a shape and size that can enhance the ergonomics of the device 400. More specifically, the handle 410 has a proximal end portion 411, a distal end portion 412, and a medial portion 413 that can be shaped in such a manner as to be easily gripped by a user (e.g., a doctor, physician, surgeon, technician, etc.). In some embodiments, the handle 410 can include a grip section 417 (see, e.g., FIG. 21) or the like that can have, for example, a rough surface finish, detents, protrusions, or the like that can enhance the ergonomics of the handle 410. In other embodiments, the grip section can be, for example, an insert, an over-mold, or the like that is formed from a relatively deformable material and that can have a relatively high coefficient of friction, thereby enhancing the ergonomics of the handle 410.

The proximal end portion 411 of the handle 410 includes a first port 420 and a second port 425 collectively referred to herein as a first set of ports 428). The first port 420 and the second port 425 can be any suitable size, shape, or configuration. In some embodiments, the first port 420 and the second port 425 can be coupled together via any suitable method (e.g., an adhesive, ultrasonic welding, mechanical fastener, and/or the like). In other embodiments, the first port 420 and the second port 425 can be monolithically formed.

Figure 20:
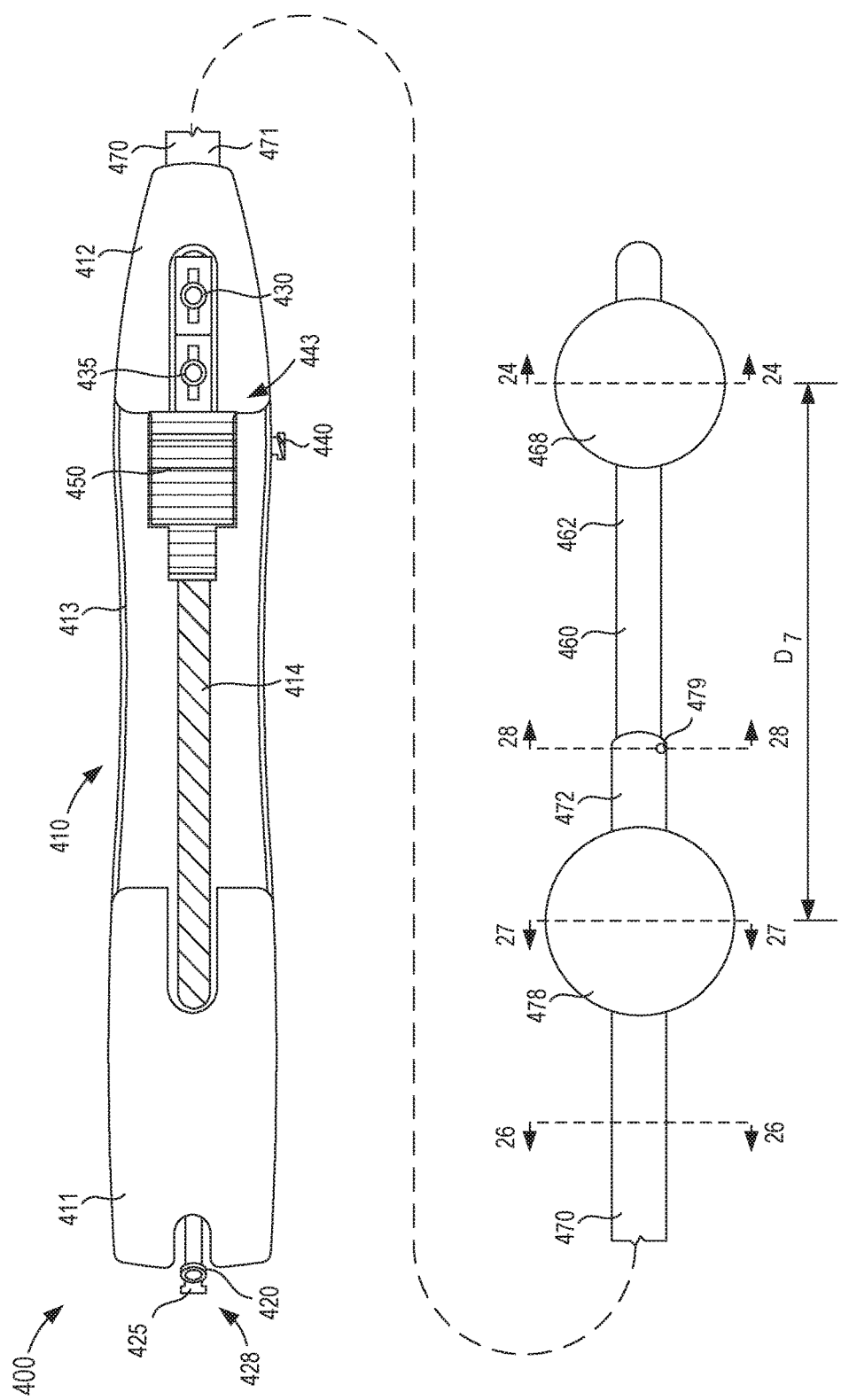
FIG. 20 is a top view of a multi-occlusion catheter insertion device according to an embodiment, in a first configuration.
Figure 21:
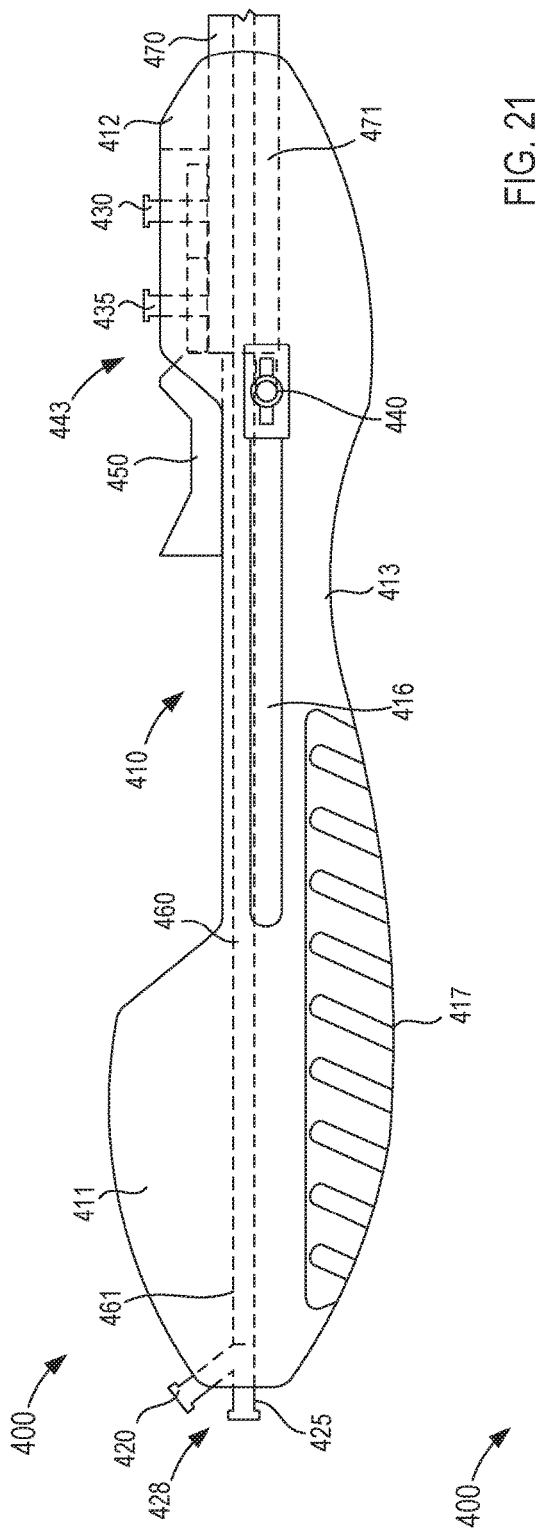
FIG. 21 is a side view of a handle included in the multi-occlusion catheter insertion device of FIG. 20.

The first port 420 and the second port 425 can extend from the proximal end portion 411 of the handle 410 such that at least a portion of the first port 420 and the second port 425 is accessible, as shown in FIGS. 20 and 21. In some embodiments, the first set of ports 428 can be, for example, a first Y-adapter, substantially similar to the Y-adapter 228 and/or 328. In other embodiments, a first port and a second port can be, for example, substantially parallel in a stacked configuration. In yet other embodiments, a handle can include a first port and a second port that are substantially coaxial and arranged in a substantially concentric configuration such that at least a portion of the first port is disposed within the second port, or vice versa.

Although not shown in FIGS. 14-29, the first port 420 and the second port 425 can be physically and fluidically coupled to an exterior device, mechanism, and/or the like as described above, for example, with reference to insertion device 100. For example, the first port 420 and the second port 425 can each define a lumen (described in more detail below) in fluid communication with such a device. The first port 420 and the second port 425 can each include a Luer-Lok® and/or any other attachment mechanism that can physically and fluidically couple the first port 420 and/or the second port 425 to any suitable device either directly or indirectly (e.g., by an intervening structure such as a flexible tubing to the like). The first set of ports 428 can be physically and fluidically coupled to the first catheter 460 such that when an external device is coupled to the handle 410 via the first port 420 and/or the second port 425, at least the portion of the first catheter 460 is placed in fluid communication with that external device via the first port 420 and/or the second port 425. For example, the first port 420 can be coupled to a device that can, for example, supply a pressurized fluid (e.g., an inert gas, air, saline, water, and/or any other suitable fluid in gaseous or liquid form) that can flow through the first port 420 to be delivered to a portion of the first catheter 460, as described in further detail herein. Furthermore, the second port 425 can be coupled to a device that can advance a guidewire or the like through the second port 425 and into a portion of the first catheter 460, as described in further detail herein. In some embodiments, a guidewire or the like can be manually inserted through the second port 425 without the use of an external device.

The distal end portion 412 of the handle 410 includes a third port 430, a fourth port 435, and a fifth port 440 (collectively referred to as a second set of ports 443). In some embodiments, the second set of ports 443 includes the fifth port 440 and only one of the third port 430 and the second port 435. The second set of ports 443 can be any suitable size, shape, or configuration as described above with reference to the first set of ports 428. For example, the second set of ports 443 can be, for example, monolithically and/or unitarily formed. In some embodiments, the second set of ports 443 can be monolithically formed with the catheter 470. In some embodiments, the second set of ports 443 can be formed with and/or coupled to any suitable structure or component of the handle 410 such that the second set of ports 443 can be moved relative to the handle 410 as described in more detail below.

The third port 430, the fourth port 435, and the fifth port 440 can each include a Luer-Lok® and/or any other attachment mechanism that can physically and fluidically couple the third port 430, the fourth port 435, and/or the fifth port 440 to any suitable attachment, device, mechanism, and/or the like. The second set of ports 443 can be physically and fluidically coupled to the second catheter 470 such that when an external device is coupled to the handle 410 via the third port 430, the fourth port 435, and/or the fifth port 440, at least a portion of the second catheter 470 is placed in fluid communication with that external device. For example, in some embodiments, the third port 430 and/or the fourth port 435 can be coupled to a device that can supply a pressurized fluid (as described above) that can flow through the third port 430 and/or the fourth port 435, respectively, to be delivered to a portion of the second catheter 470, as described in further detail herein. In some embodiments, the fifth port 440 is coupled to, for example, an infusion device that is configured to deliver a biological or therapeutic agent and/or other suitable drug formulation to a target tissue via the fifth port 440 and a portion of the second catheter 470. In some embodiments, the fifth port 440 can be coupled to, for example, an irrigation device that can deliver an irrigation fluid to, for example, an isolated segment of a bodily lumen via the fifth port 440 and a portion of the second catheter 470. In some embodiments, the fifth port 440 can be coupled to, for example, the infusion device configured to deliver the biological agent and/or other suitable drug formulation, as described in further detail herein.

Figure 22:
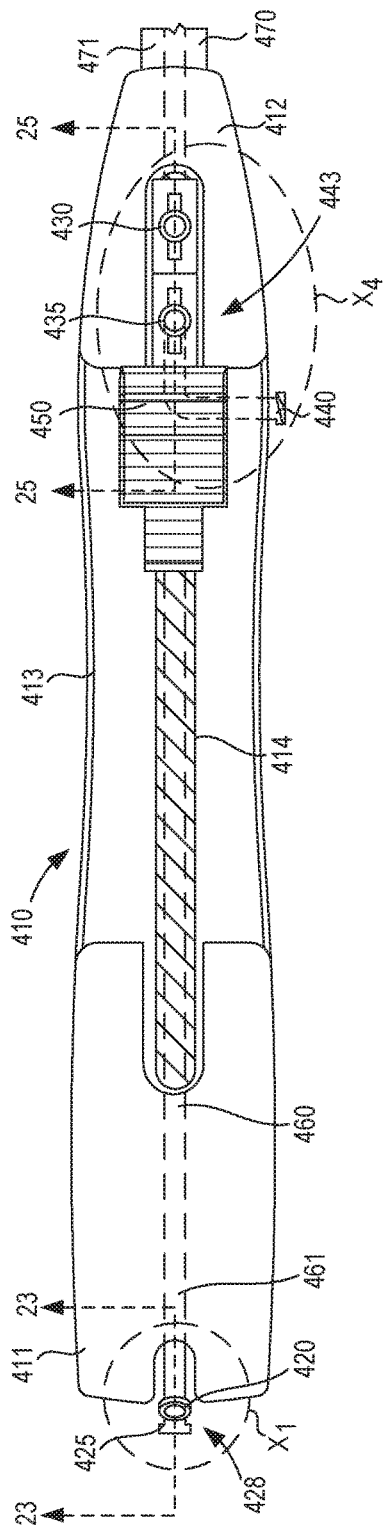
FIG. 22 is a top view of a handle included in the multi-occlusion catheter insertion device of FIG. 20.

As shown in FIGS. 20-22, the handle 410 defines a first track 414 and a second track 416. The first track 414 slidably receives a portion of the actuator 450. More specifically, at least a portion of the actuator 450 can extend through the track 414, thereby allowing a user to engage the actuator 450. As such, the track 414 can define a path along which the actuator 450 can be moved between a first position relative to the handle 410 and a second position relative to the handle 410, as described in further detail herein. In a similar manner, the second track 416 slidably receives a portion of the fifth port 440. In this manner, the fifth port 440 can extend through the second track 416 to be accessed by a user. Moreover, the second track 416 can define a path along which the fifth port 440 can be moved, as described in further detail herein.

Although the device 400 is particularly shown in FIGS. 20-29, the arrangement of the first set of ports 428, the second set of ports 443, the first track 414 and the second track 416 can be arranged along a surface of the handle 410 in various orientations. For example, although the first track 414 is shown as being defined by a top surface of the handle 410 (see, e.g., FIG. 20) and the second track 416 as being defined by a side surface of the handle 410 (see, e.g., FIG. 21), in other embodiments, a first track configured to receive an actuator can be defined by a side surface of a handle and a second track configured to receive a fifth port can be defined by a top surface of the handle. Similarly, while the first set of ports 428 and the second set of ports 443 are shown extending from the handle 410 in a specific orientation, the first set of ports 428 and/or the second set of ports 443 can be oriented in any suitable manner relative to a surface of the handle 410.

Figure 29:
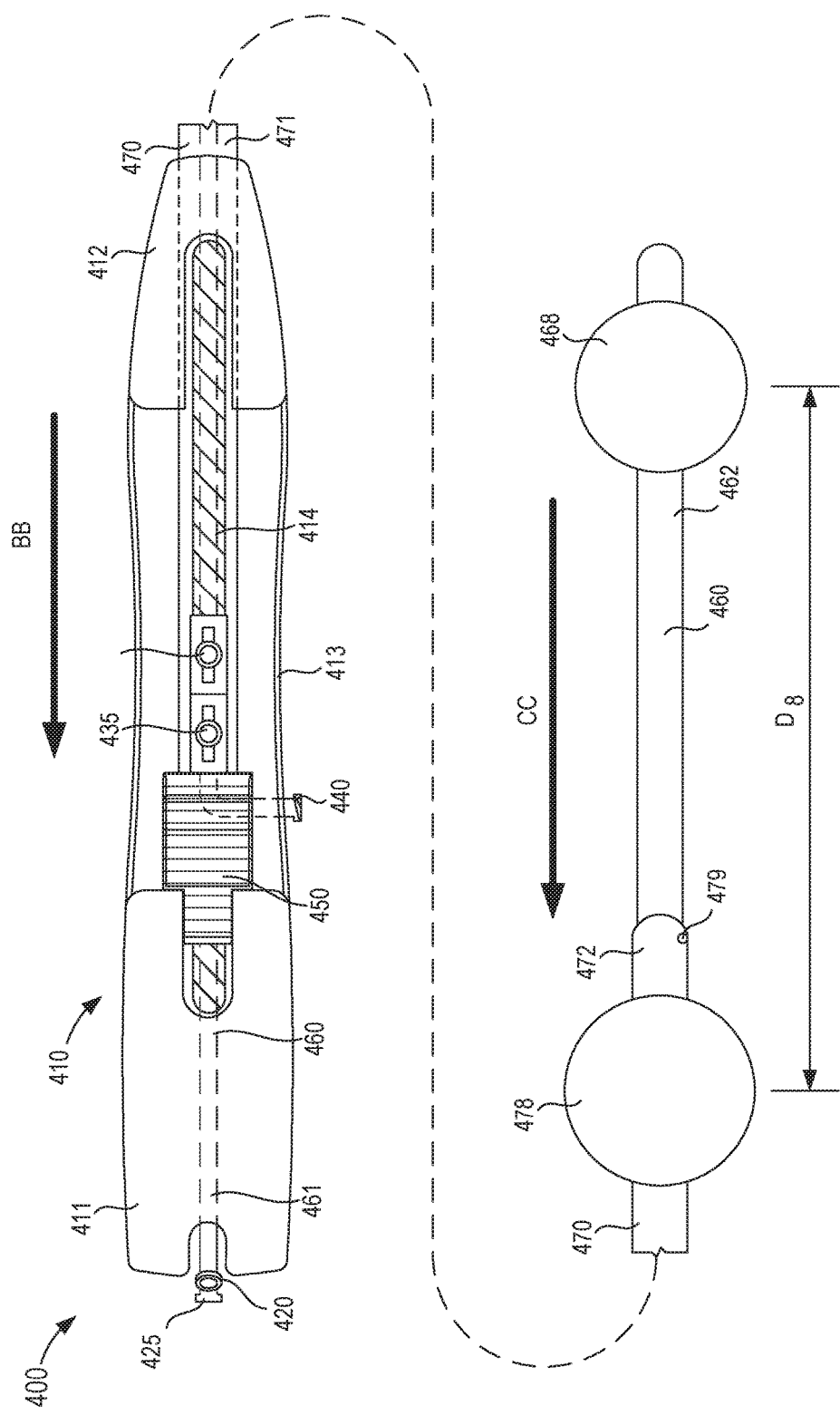
FIG. 29 is a top view of the multi-occlusion catheter insertion device of FIG. 20 in a second configuration.

The actuator 450 of the device 400 is operably coupled to the second set of ports 443. For example, in some embodiments, the actuator 450 is included in and/or coupled to the handle 410 and arranged relative to the second set of ports 443 to be operably coupled thereto. In other embodiments, a handle can be arranged such that at least a portion of an actuator is monolithically formed with at least a portion of a second set of ports. In some embodiments, an actuator is operably coupled to a second set of ports via an intervening structure or the like. For example, in some embodiments, the second set of ports 443 can be coupled to a shuttle or the like, which in turn, is coupled to an actuator. The actuator 450 can be any suitable device, mechanism, assembly, etc. that is movable between the first position relative to the handle 410, associated with the device 400 in the first configuration (FIGS. 20-22), and a second position relative to the handle 410, associated with the device 400 in the second configuration (FIG. 29).

In some embodiments, the actuator 450 can be a mechanism that can be pushed or pulled to slide within the first track 414 defined by the handle 410 between its first position and its second position. In some embodiments, the actuator 450 can be arranged to slide relatively smoothly within the track 414 when moved between its first position and its second position. In other embodiments, the handle 410 and/or the actuator 450 can include a set of ribs, teeth, detents, protrusions, etc. that are sequentially engaged as the actuator 450 is moved between its first position relative to the handle 410 and its second position relative to the handle 410. In this manner, a user can move the actuator 450 a desired distance that can be quantified by the actuator 450 and/or the handle 410 engaging a particular surface (e.g., a particular rib, tooth, detent, protrusion, etc.). In some embodiments, the handle 410 and/or the actuator 450 can be arranged at a predetermined setting that can correspond to a predetermined distance (e.g., 2 cm, 3 cm, etc.) between an end portion of the first catheter 460 and an end portion of the second catheter 470. In some embodiments, the set of ribs, teeth, detents, protrusions, etc. included in the handle 410 and/or the actuator 450 can be associated with pre-defined settings and/or adjustments.

Although not shown in FIGS. 20-29, in some embodiments, a handle 410 can include a visual indicator such as a measuring scale or the like. For example, in some embodiments, the handle 410 can include indicia (e.g., lines, markings, tic marks, etc.) that represents a gradation of a length of travel associated with moving the actuator 450 between its first position relative to the handle 410 and its second position relative to the handle 410. In some embodiments, the markings can represent distances of, for example, a centimeter, half a centimeter, a millimeter, and/or the like. In this manner, a user can view the indicia to determine a desired distance to move that actuator 450 that would otherwise be challenging or indeterminate. In some embodiments, the visual indicator can substantially correspond with the ribs, teeth, detents, protrusions, etc. of the handle 410 and/or actuator 450.

In some embodiments, the actuator 450 can be operably coupled to one or more energy storage device (e.g., a spring or the like) that can facilitate the movement of the actuator 450. For example, the actuator 450 can include a push button that can rearrange or reconfigure at least a portion of the actuator 450 to allow a spring to transition from a compressed configuration towards an uncompressed configuration to move the actuator 450 relative to the handle 410.

With the actuator 450 coupled to or monolithically formed with a portion of the second set of ports 443, the actuator 450 can be operable in moving the second set of ports 443 between a first position relative to the handle 410 (e.g., a distal position) and a second position relative to the handle 410 (e.g., a proximal position). Moreover, with the second catheter 470 physically and fluidically coupled to the second set of ports 443 (as described above), the movement of the actuator 450 and the second set of ports 443 can move the second catheter 470 between a first position relative to the handle 410 and a second position relative to the handle 410, as described in further detail herein.

Figure 23:
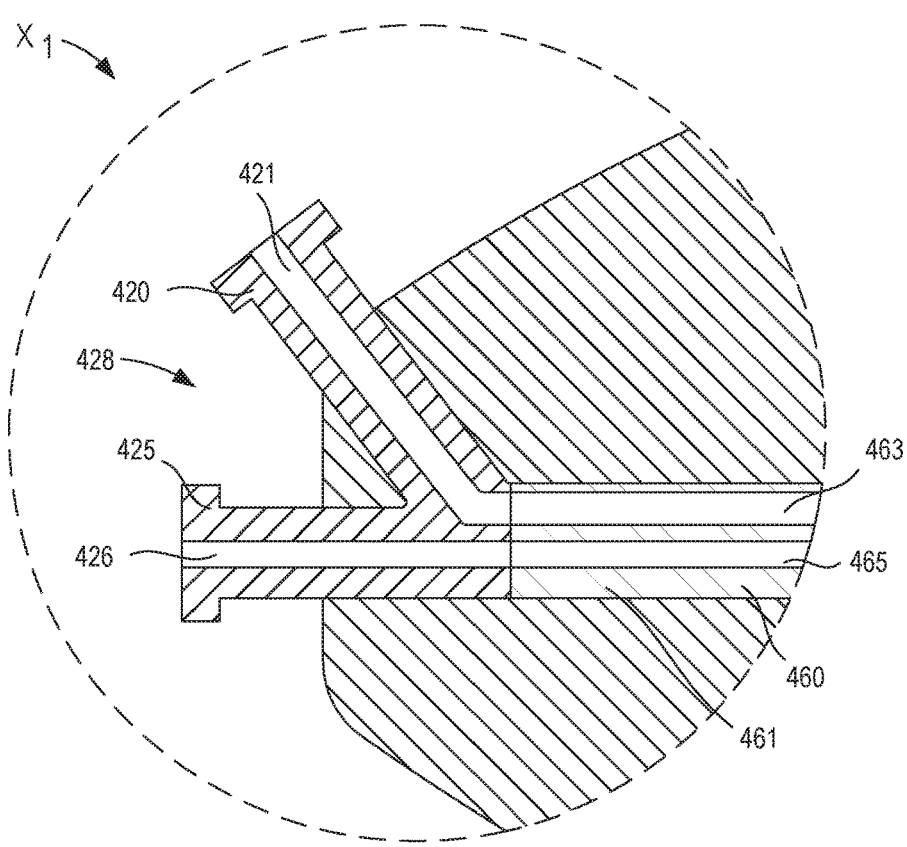
FIG. 23 is an enlarged cross-sectional view of a portion of the handle of FIG. 21, indicated by the region $X_1$ and taken along the line 23-23 in FIG. 22.

The first catheter 460 and the second catheter 470 can be any suitable catheter device. For example, in some embodiments, the first catheter 460 and the second catheter 470 are multi-lumen catheters. The first catheter 460 has a proximal end portion 461 (see, e.g., FIGS. 21, 23 and 29) and a distal end portion 462 (see, e.g., FIGS. 20 and 29), and defines a first lumen 463 and a second lumen 465 (see, e.g., FIGS. 24-28). The proximal end portion 461 of the first catheter 460 is disposed within a portion of the handle 410. More specifically, the proximal end portion 461 of the first catheter 460 can be fixedly disposed within the portion of the handle 410 to place the first catheter 460 in fluid communication with the first set of ports 428. In some embodiments, the first catheter 460 can be physically and fluidically coupled to the first set of ports 428. In other embodiments, a device can include a first catheter that is monolithically formed with a first set of ports. In this manner, the proximal end portion 461 of the first catheter 460 is arranged such that the first lumen 463 of the first catheter 460 is in fluid communication with a lumen 421 defined by the first port 420 and the second lumen 465 of the first catheter 460 is in fluid communication with a lumen 426 of the second port 425, as shown in FIG. 23. Therefore, an external device (e.g., a device that can supply a pressurized fluid, as described above) can be physically and fluidically coupled to the first port 420 to place the external device in fluid communication with the first lumen 463 of the first catheter 460. Similarly, an external device including at least a guidewire (not shown) can be coupled to the second port 425 and can be manipulated to advance the guidewire through the second port 425 and into the second lumen 465, as described in further detail herein.

Referring back to FIG. 20, the distal end portion 462 of the first catheter 460 extends beyond a distal end portion of the handle 410 and includes an occlusion member 468. The occlusion member 468 can be any suitable device or mechanism that is configured to selectively limit, block, obstruct, or otherwise occlude a body lumen (e.g., artery) in which the occlusion member 468 is disposed. For example, in some embodiments, the occlusion member 468 can be an inflatable balloon or the like that can be transitioned between a collapsed (e.g., deflated) configuration and an expanded (e.g., inflated) configuration.

Figure 24:
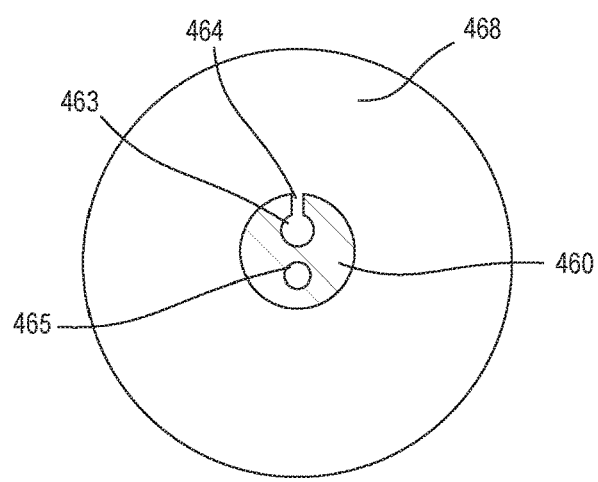
FIG. 24 is a cross-sectional view of a portion of the multi-occlusion catheter insertion device of FIG. 20, taken along the line 24-24.

The arrangement of the first catheter 460 can be such that the first lumen 463 is in fluid communication with the occlusion member 468. For example, as shown in FIG. 24, the distal end portion 462 of the first catheter 460 can define a channel 464 that places the first lumen 463 in fluid communication with the occlusion member 468. Thus, when the first port 420 is fluidically coupled to a device that supplies a pressurized fluid (e.g., air, inert gas, or liquid), the pressurized fluid can be delivered to the occlusion member 468 via the lumen 421 of the first port 420, the first lumen 463 of the first catheter 460, and the channel 464 of the first catheter 460. In this manner, the pressurized fluid can transition the occlusion member 468 between a collapsed configuration (not shown) and an expanded configuration (see e.g., FIG. 20), as described in further detail herein.

The second catheter 470 of the device 400 has a proximal end portion 471 (see, e.g., FIGS. 20-22) and a distal end portion 472 (see, e.g., FIGS. 20 and 29), and defines a first lumen 473, a second lumen 474, a third lumen 476 and an opening 479 (also referred to herein as "infusion aperture") (as shown, for example, in FIGS. 25-28). The second catheter 470 is movably disposed about a portion of the first catheter 460 (see, e.g., FIGS. 21-23). More specifically, the second catheter 470 can be arranged such that the first catheter 460 is movably disposed within the first lumen 473 defined by the second catheter 470, as shown, for example, in FIGS. 26-28.

Figure 25:
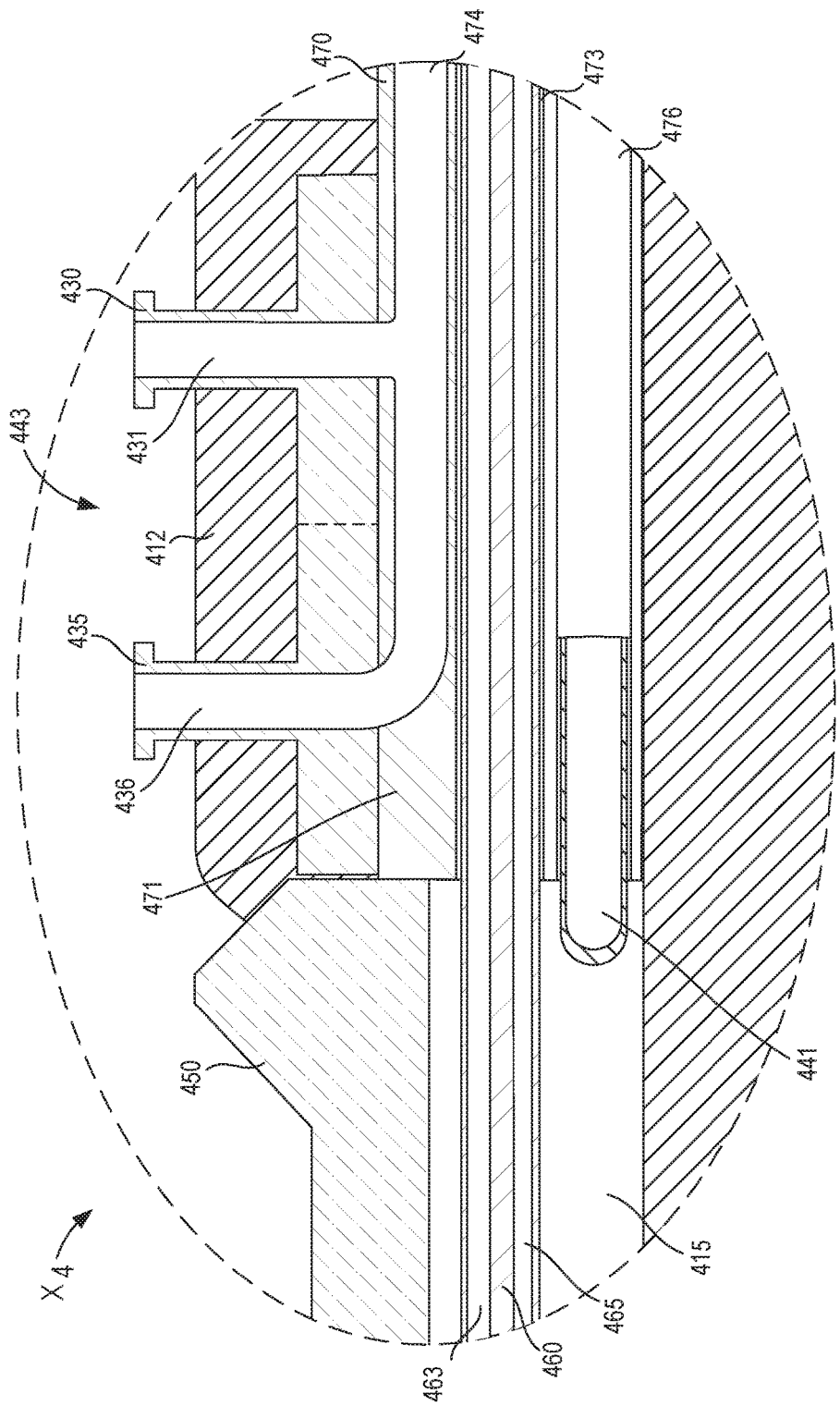
FIG. 25 is an enlarged cross-sectional view of a portion of the handle of FIG. 21, indicated by the region $X_2$ and taken along the line 25-25 in FIG. 22.
Figure 26:
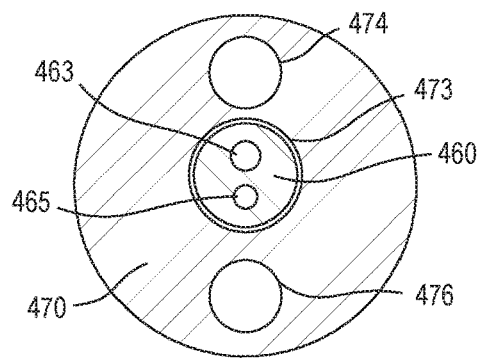
FIG. 26 is a cross-sectional view of a portion of the multi-occlusion catheter insertion device of FIG. 20, taken along the line 26-26.

The proximal end portion 471 of the second catheter 470 is movably disposed within the handle 410 to place the second catheter 470 in fluid communication with the second set of ports 443. In some embodiments, the second catheter 470 can be physically and fluidically coupled to the third port 430 and the fourth port 435, and/or the fifth port 440. In other embodiments, a catheter insertion device can include a second catheter that can be movably disposed within a handle and can be operably coupled to one or more ports via an intervening structure such as, for example, flexible tubing or the like. In yet other embodiments, a catheter insertion device can include a second catheter that is monolithically formed with a third port, a fourth port, and/or a fifth port. In this manner, the second catheter 470 is arranged such that the first lumen 473 of the second catheter 470 movably receives the first catheter 460, the second lumen 474 of the second catheter 470 is in fluid communication with a lumen 431 defined by the third port 430 and a lumen 436 defined by the fourth port 435, and the third lumen 476 of the second catheter 470 is in fluid communication with a lumen 441 defined by the fifth port 440, as shown in FIG. 25.

Referring back to FIG. 20, the distal end portion 472 of the first catheter 470 extends beyond a distal end portion of the handle 410 such that an occlusion member 478 of the second catheter 470 is disposed in a proximal position relative to the occlusion member 468 of the first catheter 478. Expanding further, the first catheter 460 extends within the proximal end portion 471 and the distal end portion 472 when disposed in the first lumen 473. Thus, the occlusion member 468 of the first catheter 460 can be disposed in a distal position relative to the occlusion member 478 of the second catheter 470. The occlusion member 478 can be any suitable device or mechanism that is configured to selectively limit, block, obstruct, or otherwise occlude a body lumen (e.g., artery) in which the occlusion member 478 is disposed. For example, in some embodiments, the occlusion member 478 can be substantially similar to the occlusion member 468 of the first catheter 468.

Figure 27:
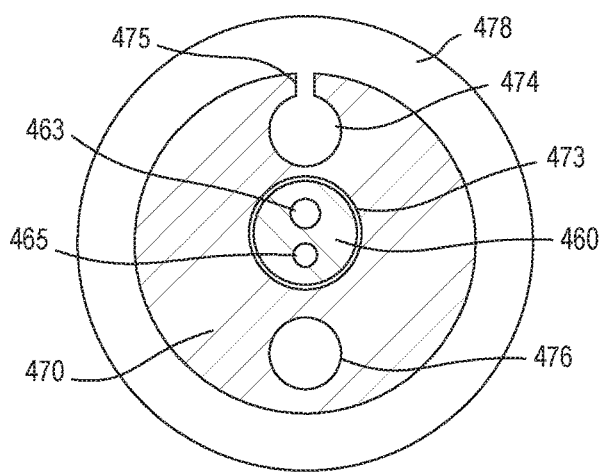
FIG. 27 is a cross-sectional view of a portion of the multi-occlusion catheter insertion device of FIG. 20, taken along the line 27-27.
Figure 28:
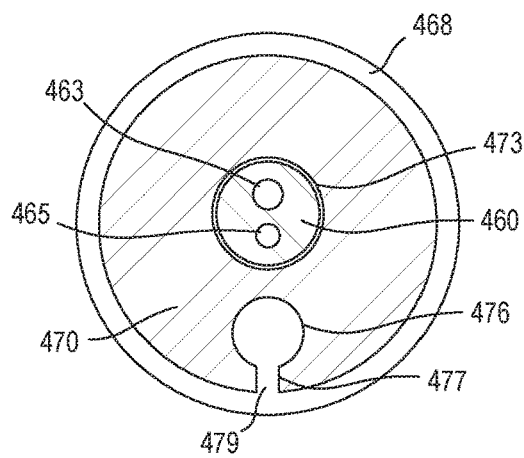
FIG. 28 is a cross-sectional view of a portion of the multi-occlusion catheter insertion device of FIG. 20, taken along the line 28-28.

The arrangement of the second catheter 470 can be such that the second lumen 474 is in fluid communication with the occlusion member 468. For example, as shown in FIG. 27, the distal end portion 472 of the second catheter 470 defines a channel 475 that places the second lumen 474 in fluid communication with the occlusion member 478. Thus, when the third port 430 (and/or the fourth port 435) is fluidically coupled to a device that supplies a pressurized fluid, the pressurized fluid can be delivered to the occlusion member 478 via the lumen 431 of the third port 430 (and/or the lumen 436 of the fourth port 435), the second lumen 474 of the second catheter 470, and the channel 475 of the second catheter 470. In this manner, the pressurized fluid can transition the occlusion member 478 between a collapsed configuration (not shown) and an expanded configuration (as shown in FIGS. 20 and 29). In a similar manner, the arrangement of the second catheter 470 can be such that the third lumen 476 is in fluid communication with the opening 479 (see, e.g., FIG. 28). For example, the distal end portion 472 of the second catheter 470 defines a channel 477 that places the third lumen 476 in fluid communication with the opening 479, as shown in FIG. 28. Thus, when the fifth port 440 is fluidically coupled to an external device that supplies irrigation or to a device that supplies a therapeutic agent, the irrigation fluid or therapeutic agent can be delivered to an isolated segment of a bodily lumen via the lumen 441 defined by the fifth port 440 and the third lumen 476, the channel 477, and the opening 479 defined by the second catheter 470.

The device 400 can be moved from the first configuration to the second configuration by moving the actuator 450 from its first position (e.g., a distal position) relative to the handle 410 to its second position (e.g., a proximal position) relative to the handle 410, as indicated by the arrow BB in FIG. 29. Expanding further, with the second catheter 470 movably disposed about the first catheter 460 and with the proximal end portion 471 of the second catheter 470 operably coupled to the actuator 450, the movement of the actuator 450 from its first position to its second position moves the second catheter 470 relative to the first catheter 460, as indicated by the arrow CC in FIG. 29. For example, when the device 400 is in the first configuration, a first distance $D_7$ (FIG. 20) can be defined between the occlusion member 468 of the first catheter 460 and the occlusion member 478 of the second catheter 470. With the first catheter 460 fixedly disposed within the handle 410, the movement of the second catheter 470 in the CC direction (e.g., the proximal direction) increases the distance between the occlusion member 468 of the first catheter 460 and the occlusion member 478 of the second catheter 470 to a second distance $D_8$, as shown in FIG. 29. Thus, a segment or volume having a desired length can be defined between the occlusion member 468 of the first catheter 460 and the occlusion member 478 of the second catheter 470.

Figure 30:
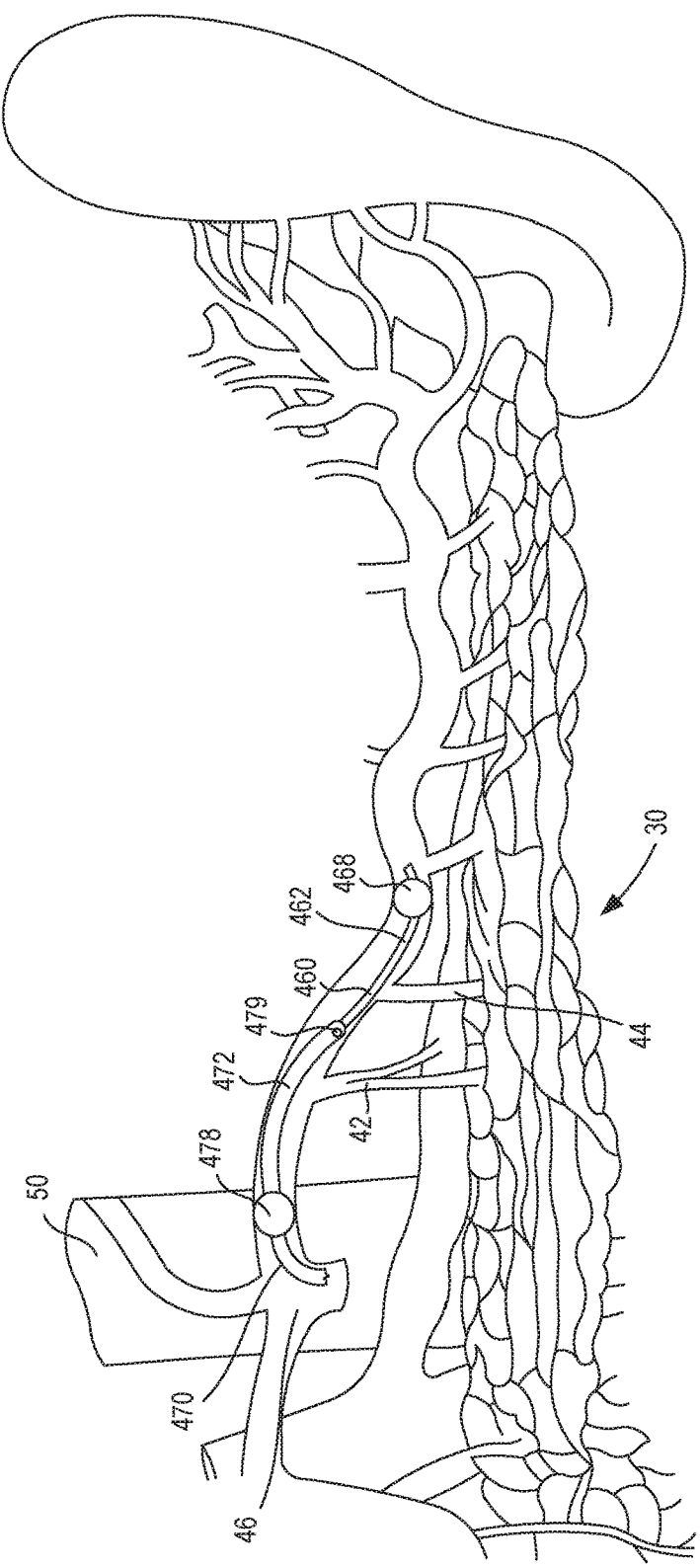
FIG. 30 is an illustration of a portion of the multi-occlusion catheter insertion device of FIG. 20 in use within a portion of a body.

In use, a guidewire can be inserted into the lumen 426 of the second port 425 and through the second lumen 465 defined by the first catheter 460. In this manner, the guidewire can be advanced through a bodily lumen and the device 400 can be manipulated to advance the first catheter 460 and the second catheter 470 along the guidewire. Thus, the distal end portion 462 of the first catheter 460 and the distal end portion 472 of the second catheter 470 can be placed at a target location within the bodily lumen such as, for example, the haptic or splenic artery of the pancreas, as shown in FIG. 30. At the target location, the actuator 450 can be moved between its first position and its second position relative to the handle 410 (e.g., the BB direction in FIG. 29) to define a desired distance (e.g., the distance $D_8$ in FIG. 29) between the occlusion member 468 of the first catheter 460 and the occlusion member 478 of the second catheter 470. With the desired distance defined between the occlusion members 468 and 478, and with an inflation source coupled to the first port 420 and the same or a different inflation source coupled to the third port 430 (and/or the fourth port 435), the occlusion member 468 of the first catheter 460 and the occlusion member 478 of the second catheter 470, respectively, can be transitioned from a collapsed or deflated configuration to an expanded or inflated configuration to substantially isolate a segment of the bodily lumen disposed therebetween (e.g., the pancreatic segment or portion of the splenic artery 40 associated with, for example, the dorsal pancreatic artery 42 and/or the pancreatic magnum artery 44), as shown in FIG. 30. FIG. 30 is an illustration of the catheter device 400 disposed in situ within the splenic branch of the celiac artery. As shown in FIG. 30, the occlusion elements 468 and 478 define or isolate an area of interest in between the occlusion elements 468 and 478. Specifically, in this example, the region or area of interest with blood supply to the pancreas is isolated via the occlusion elements 468 and 478, spaced according to the location of the dorsal pancreatic artery 42 and the pancreatic magnum artery 44.

With the occlusion members 468 and 478 substantially occluding the body lumen, a biological/therapeutic agent can be delivered to the substantially isolated segment via the fifth port 440, the third lumen 476, and the opening 479 (i.e., the infusion aperture), into the area substantially isolated between the occlusion elements 468 and 478. In some instances, the substantially isolated segment can be irrigated by coupling an irrigation source to the fifth port 440. Thus, the irrigation can be delivered to the substantially isolated segment via the lumen 441 of the fifth port 440 and the third lumen 476, the channel 477, and the opening 479 of the second catheter 470. In some instances, such irrigation can be delivered prior to the delivery of the biological/therapeutic agent, after the delivery of the biological/therapeutic agent, or substantially concurrently with the biological/therapeutic agent.

Figure 31:
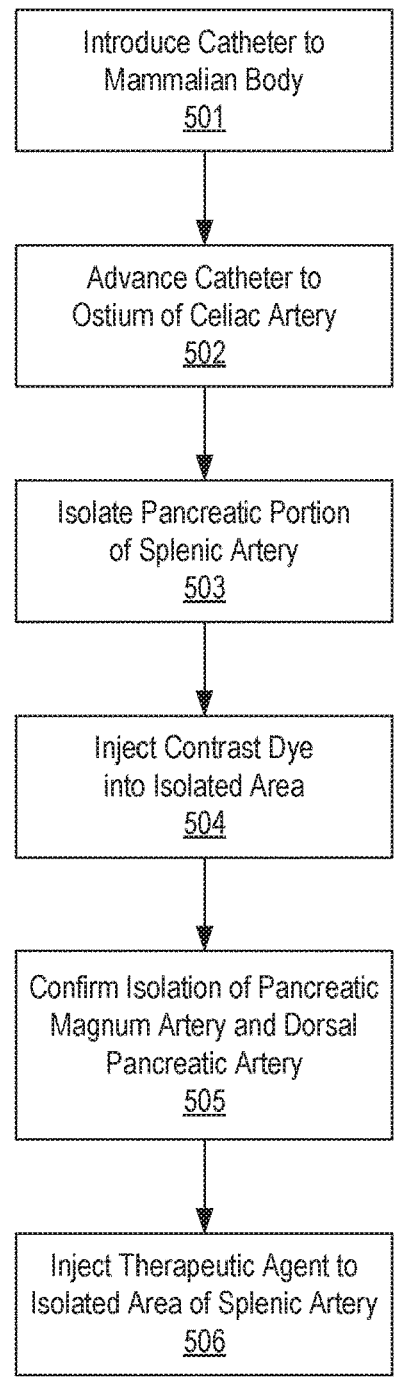
FIG. 31 is a flowchart illustrating a method for treating the pancreas, according to an embodiment.

FIG. 31 is a flowchart illustrating a method of accessing and treating a pancreas. The method can be used, for example, to occlude a portion of the splenic branch of the celiac artery supplying the pancreatic tail. The method includes introducing a catheter (e.g., the catheter device 100, 200, 300, and/or 400) into a mammalian body over a guidewire (211, 311) into a celiac artery, at 501. The catheter device can include an inner catheter (e.g., the first catheter 160, 260, 360, and/or 460) slidably coupled to an outer catheter (e.g., the second catheter 170, 270, 370, and/or 470). In some embodiments, a guide catheter can be exchanged over the guidewire into the celiac artery for support and introduction of the catheter device. After the guidewire is in place, the catheter device can be positioned over the guidewire, at 502, and positioned to allow placement of a distal occlusion element (e.g., the distal occlusion element 168, 268, 368, and/or 468) of the inner catheter at a distal edge of the pancreatic portion of the splenic artery (see, e.g., FIG. 30). The distal occlusion element and a proximal occlusion element (e.g., the proximal occlusion element 178, 278, 378, and/or 478) of the outer catheter are positioned to isolate a target portion of the pancreatic artery and moved to an expanded configuration, at 503. After the occlusion elements are deployed, contrast dye is injected through an injection port of the outer catheter and the isolated area of the splenic artery is visualized to identify the pancreatic branches, at 504. Visualization enables the clinician to confirm isolation of the pancreatic magnum artery and dorsal pancreatic artery or any other large artery supplying the pancreatic body or tail in the area, at 505. If desired, the catheter device can be moved back and the procedure repeated until the clinician can confirm that the catheter is correctly positioned. Some example isolation regions include: (a) the pancreatic magnum artery 44 (and its branches), (b) the dorsal pancreatic artery 42 if the origin is within the splenic artery 40, and (c) both pancreatic magnum artery 44 and dorsal pancreatic artery 42 arteries are isolated in one contiguous area (if other extra-pancreatic arteries do not arise between the origin of the two within the splenic artery 40).

After the first takeoff of the pancreatic magnum artery 44 is identified (or the dorsal pancreatic artery), the placement of the outer catheter of the catheter device can allow the edge of the distal occlusion element to be placed beyond this artery. At this point, the inner catheter can be secured in place, and the outer catheter can be moved relative to the inner catheter to allow the maximum perfusion area to the body and tail of the pancreas. Frequent injection of contrast through the infusion port can be made to ensure no extra-pancreatic vessels are included in the isolated area.

After the desired area is isolated and the occlusion elements are positioned at a desired location, the therapeutic cells/biologics/agent is introduced to the isolated area of the splenic artery through the infusion port of the outer catheter, at 506. The infusion port design can allow rapid and atraumatic infusion of cells/biologics/agent into the isolated area. This allows the clinician to adjust rate of infusion of therapeutic cells/biologics/agents into the isolated area based on specific pharmacodynamics and or engraftment efficiency requirements. The infusion of the therapeutic material can be followed by heparinized blood to exclude any residual cells left behind in the dead space of the catheter device. During isolation of the artery described above, perfusion to the end organ to the artery spleen can be disrupted, but the redundancy in the arterial perfusion system to the spleen, and limited time during which the arterial supply is interrupted, should prevent any long-term sequela, or abnormal condition of the splenic cells. If needed and/or desired, the guidewire port can be used to perform perfusion of the splenic artery beyond the isolated area. For example, the guidewire can be removed from its port after the catheter device is in place, and the guidewire port can be connected to a source of arterial blood with suitable pressure (i.e. the side port of an arterial sheath or guide sheath). At the end of the infusion, both occlusion elements are moved to a collapsed configuration and the catheter device is removed from the body over the guidewire as one unit, followed by the guidewire and the guide catheter.

In a variation of the method described above using balloons as the occlusion elements, the same catheter can be used to isolate arterial branches supplying the head of the pancreas via the hepatic artery or superior mesenteric artery. One such clinical possibility is treatment of pancreatic cancer with the tumor located in the head of the pancreas. After placement of the catheter device in the respective artery, the infusion of contrast through the infusion port can identify the branches most proximate to the tumor, and then after occluding the distal and proximal portion of the artery around the branch(es), the chemotherapeutic agent can be delivered selectively to the area of interest in the pancreas.

In some embodiments, a method can include introducing a catheter device into a splenic artery. The catheter device can include an inner catheter, a first expandable occlusion element coupled to the inner catheter, an outer catheter defining a first lumen configured to introduce a therapeutic biologic/agent to one or more target pancreatic vessels, a second lumen configured to slidably receive at least a portion of the inner catheter, and a second expandable occlusion element coupled to the outer catheter and disposed proximally to the first occlusion element. The catheter is advanced to a target pancreatic portion of the splenic artery. A region of the target pancreatic portion of the splenic artery is selectively isolated and the therapeutic biologic/agent is injected into the isolated region. In some embodiments, the therapeutic biologic/agent includes stem cells. In some embodiments, the method further includes advancing at least a portion of the catheter device to an ostium of a celiac artery, its hepatic branch, or if necessary, the superior mesenteric artery (based on individual anatomy). In some embodiments, a contrast dye is injected into the isolated region and isolation of a pancreatic magnum artery and/or a dorsal pancreatic artery can be confirmed. In some embodiments, a guidewire can be disposed through the infusion lumen to focally perforate the vascular lumen in the isolated area to increase exogenous cell penetration into the pancreatic tissue. In some embodiments, the therapeutic biologic can be introduced into the isolated segment or region to enhance cellular transmigration across the endothelial cells prior to introduction of the therapeutic biologic.

Figure 32:
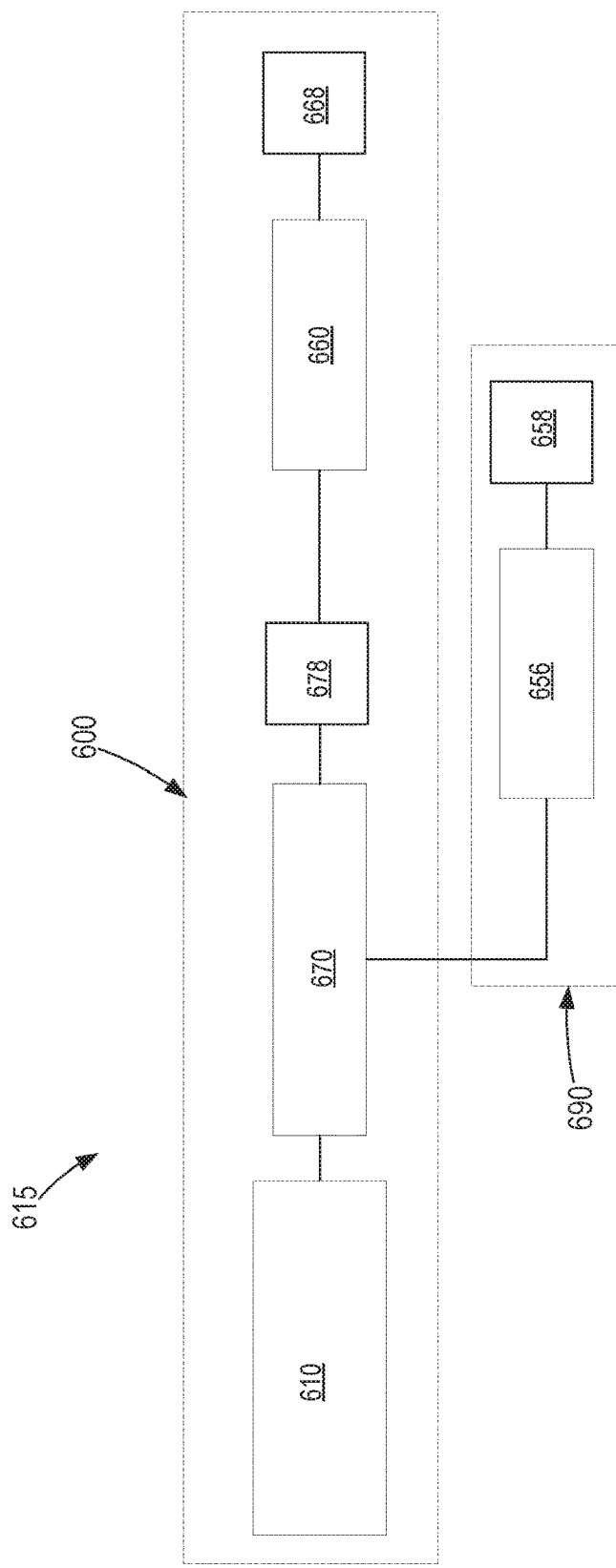
FIG. 32 is a schematic illustration of a catheter system, according to an embodiment.
Figure 34A:
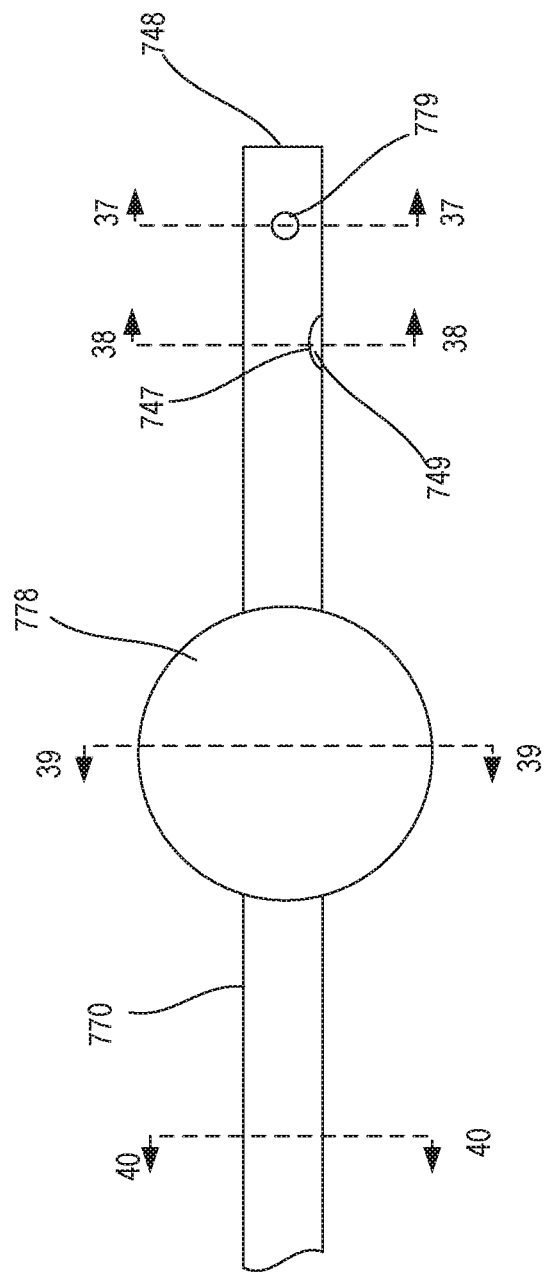
FIG. 34A is a side view of the second catheter of the catheter system of FIG. 33.
Figure 34B:
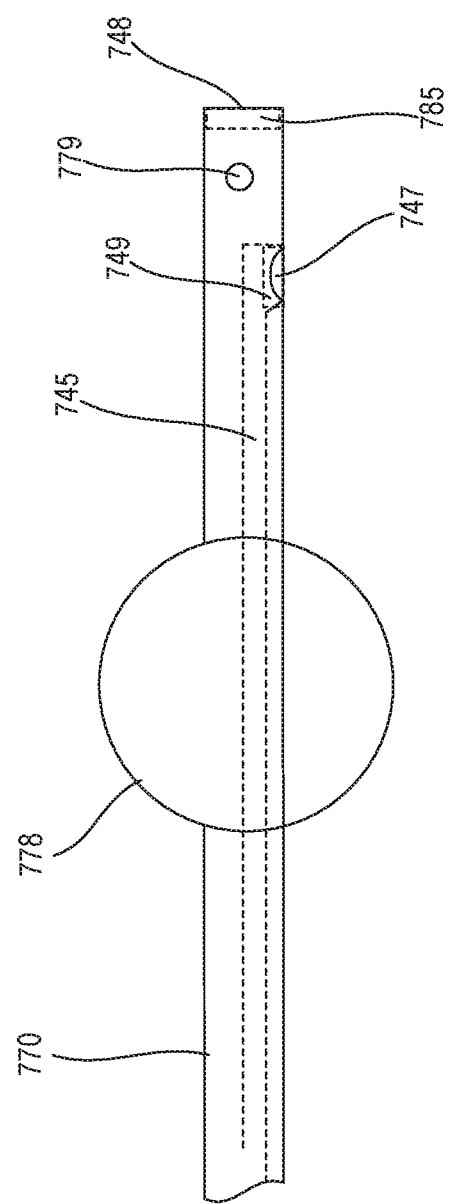
FIG. 34B is a side view of a portion of the outer catheter of the catheter system of FIG. 33 showing in phantom a lumen for the third catheter and a seal coupled to the second catheter.

FIG. 32 is a schematic illustration of a catheter system 615, according to an embodiment. The catheter system 615 includes a catheter assembly 600 and a secondary catheter 690. The catheter system 615 includes multiple occlusion members or elements that can be used to occlude one or more portions of a body lumen such as for example, an artery or vessel within a patient. The catheter assembly 600 (also referred to herein as "catheter device") can include the same or similar features and function the same as or similar to the catheter devices described above (e.g., 100, 200, 300, 400). The catheter assembly 600 includes a first catheter 660 (also referred to herein as "inner catheter") and a second catheter 670 (also referred to herein as "outer catheter").

A first occlusion member 668 is disposed at a distal end portion of the first catheter 660 and a second occlusion member 678 is disposed at a distal end portion of the second catheter 670. The occlusion members 668 and 678 can be any suitable device or mechanism that is configured to selectively limit, block, obstruct, or otherwise occlude a lumen (e.g., artery, vessel, vasculature) in which the occlusion member(s) 668 and 678 are disposed. The first occlusion member 668 and the second occlusion member 678 can each be, for example, inflatable or expandable occlusion members such as the balloon occlusion elements described above for dilation catheter 200. In some embodiments, the occlusion member 678 can be substantially similar to the occlusion member 668 of the first catheter and in other embodiments, the first occlusion member 668 can have a different configuration or structure than the second occlusion member 678. The first occlusion member 668 and the second occlusion member 678 can each be moved between a collapsed configuration (also referred to as "retracted configuration") for insertion of the catheter device 600 into a body of a patient (e.g., into an artery, vessel or other body lumen) and an expanded configuration (also referred to as "dilated configuration" or "inflated configuration") for occluding a portion of a body lumen (e.g., artery, vessel). The first and second occlusion members 668 and 678 when in the collapsed configuration have a smaller outer perimeter (or diameter) than when in the expanded configuration.

The catheter device 600 can include some or all of the various features and functions described above for other embodiments of a dilation catheter (e.g. catheter devices 100, 200, 300, 400), and therefore, some features and functions are not described in detail with respect to catheter device 600. For example, the catheter device 600 can include a handle 610 with controls and actuators as described for previous embodiments. The handle 610 can be any suitable shape, size, or configuration. For example, in some embodiments, the handle 610 can have a shape and size that are configured to enhance the ergonomics of the device 600. As described above, the handle 610 can be grasped by a user (e.g., a doctor, physician, surgeon, technician, etc.) to insert a portion of the first catheter 660 and a portion of the second catheter 670 into a body lumen of a patient and can be used to move, inflate, deflate, adjust, and/or otherwise reconfigure the portion of the first catheter 660 and the portion of the second catheter 670 within the bodily lumen. For example, the second catheter 670 can be moved relative to the first catheter 660, or vice-versa, to adjust a distance between the first occlusion member 668 and the second occlusion member 678. The catheter device 600 can be used to isolate a segment of a bodily lumen within the space defined between the first occlusion member 668 and the second occlusion member 678. Thus, a procedure can then be performed within the isolated segment such as for example, delivering a therapeutic material/agent to the isolated segment.

More specifically, as with the previously described embodiments of a catheter device, the second catheter 670 defines a first lumen configured to movably receive the first catheter 660 such that the first catheter 660 and the second catheter 670 can be moved relative to each other and a distance between the first occlusion member 668 and the second occlusion member 678 can be adjusted. The catheter device 600 can also include a seal element (not shown in FIG. 32) (also referred to as a "seal", "sealing element", "selective sealing element", or "filter-ring") disposed at or near a distal end of the second catheter 670. For example, the seal element can be disposed within the first lumen near a distal opening in fluid communication with the first lumen and disposed in sealing engagement with an outer surface of the first catheter 660. The seal element can prevent the entry of cells and or biologics that have been injected into a body lumen (e.g., from an infusion port described below) from flowing back into the first lumen of the second catheter 670. By doing so, a maximum number of cells can be delivered to the treatment area, and improve engraftment efficiency. The seal element can be for example, a ring, a membrane, a one-way valve, a self-sealing member, a one-way valve, or other known sealing elements used in medical devices. The second catheter 670 can also define an inflation lumen (not shown in FIG. 6) that can be used to communicate an inflation medium to and from the second occlusion member 678.

The first catheter 660 can define a guidewire lumen (not shown in FIG. 32) and an inflation lumen (not shown in FIG. 32). The guidewire lumen can be used to insert and receive a guidewire therethrough, as described above for previous embodiments. The inflation lumen can be used to communicate an inflation medium to and from the first occlusion member 668. The second catheter 670 and/or the first catheter 660 can also define an infusion lumen in communication with an infusion port (each not shown in FIG. 32) that can be used to communicate a therapeutic material to a selected target region within the patient. The infusion port(s) can be defined, for example, on a side wall of the first catheter 660 and/or a side wall of the second catheter 670. The infusion port(s) can also be disposed between the first occlusion member 668 and the second occlusion member 678. Thus, when the occlusion members 668 and 678 are deployed within a body lumen of a patient to isolate a target region within a body lumen, the infusion port can be used to communicate a therapeutic material to the isolated region.

The secondary catheter 690 (also referred to herein as "treatment catheter") can include a third catheter 656 and a third occlusion member 658 disposed at a distal end portion of the third catheter 656. The third occlusion member 658 can be any suitable device or mechanism that is configured to selectively limit, block, obstruct, or otherwise occlude a lumen (e.g., artery, vessel, vasculature) in which the occlusion member 658 is disposed. For example, the third occlusion member 658 can be inflatable or expandable. The third catheter 656 can define a guidewire lumen (not shown in FIG. 32) that can be used to communicate an inflation medium to and from the third occlusion member 658. The secondary catheter assembly 690 can be movably disposed within a second lumen defined by the second catheter 670 and be moved outside a side port defined by the second catheter 670 that is in fluid communication with the second lumen. The second catheter 670 can also include a second seal (not shown in FIG. 32) that can be disposed within the second lumen near the side port and disposed about an outer surface of the third catheter 656. As with the seal element described above disposed within the first lumen of the second catheter 670, the second seal disposed in the second lumen can prevent the entry of cells and or biologics that have been injected into a body lumen from flowing back into the second lumen of the second catheter 670. The second seal within the second lumen of the second catheter 670 can be for example, a ring, a membrane, a one-way valve, or other known sealing elements used in medical devices.

In use, as described for previous embodiments, the catheter device 600 can be inserted into a body lumen (e.g., an artery, vessel, portion of a vasculature) with the first and second occlusion members 668 and 678 both in a collapsed configuration. The first and second occlusion members 668 and 678 can be positioned within a desired target location within the body lumen and then moved to their expanded configuration (e.g., inflated) to occlude the body lumen and isolate a portion of the body lumen. As described above, the infusion port is disposed between the first occlusion member 668 and the second occlusion member and can be used to introduce a therapeutic material to the isolated portion of the body lumen as described above for previous embodiments.

If the body lumen (e.g., vessel, artery) is main vessel with a side branch vessel in fluid communication therewith, or the body lumen is part of a bifurcated vessel having a first body lumen and a second body lumen, and the target region to be treated includes a portion of the main vessel, or first body lumen and a portion of the branch vessel, or second body lumen, the secondary catheter 690 can optionally be used. In such a case, the first occlusion member 668, the second occlusion member 678 and the third occlusion member 658 can collectively define a target region to be treated that includes a portion of the first body lumen (e.g., main vessel or first portion of bifurcated vessel) and a portion of a second body lumen (e.g., branch of main vessel or second portion of bifurcated vessel). For example, with the third occlusion member 658 in a collapsed configuration, the secondary catheter 690 can be moved distally within the second lumen of the second catheter 670 and moved outside of the side port and into the second body lumen within the patient. When the third occlusion member 658 is disposed at a desired target location within the second body lumen, the third occlusion member 658 can be moved to its expanded configuration (e.g., inflated) such that the third occlusion member 658 occludes a portion of the second body lumen. With the third occlusion member 658 expanded, an isolated region will be defined by the first occlusion member 668, the second occlusion member 678 and the third occlusion member 658 that spans between the portion of the first body lumen (e.g., main vessel or first portion of bifurcated vessel) and the portion of the second body lumen (e.g., branch of main vessel or second portion of bifurcated vessel). A therapeutic material can then be injected through the infusion lumen and out of the infusion port into the isolated region. In some cases, occlusion of the branch vessel may be desirable, for example, to achieve a static flow in the main vessel to then inject a therapeutic material therein. For example, in some such cases, coils are typically used to occlude the branch vessel.

The secondary catheter 690 can exit the side port at any suitable angle to reach a target side branch or other body lumen. For example, in some embodiments, the secondary catheter 690 can exit the side port of the second catheter 670, for example, at an angle of substantially 90 degrees (see, for example, FIGS. 33 and 42). In other cases, it may be desirable for the secondary catheter 690 to exit the side port of the second catheter 670 at less than 90 degrees, for example, when using the catheter system within a bifurcated vessel (see, for example, FIGS. 41 and 44). In other cases, it may be desirable for the secondary catheter 690 to exit the side port of the second catheter 670 at greater than 90 degrees.

In some embodiments, the third catheter 656 can also define an infusion port (not shown in FIG. 32) that can be used to communicate a therapeutic material to a target region within a patient as described in more detail below with reference to FIGS. 41-43. In some embodiments, rather than the secondary catheter 690 being inserted through a second lumen and side port of the second catheter 670, the secondary catheter 690 can be movably disposed within the infusion lumen and exit the infusion port of the second catheter 670. In such an embodiment, the secondary catheter 690 can be used in the same or similar manner as described above to occlude and isolate a portion of a second body lumen (e.g., a branch or a portion of a bifurcated body lumen). Further details of such a catheter system are described below with reference to specific embodiments.

In some embodiments, the catheter device 600 can be used with a different type of device than the secondary catheter 690. For example, in some embodiments, a treatment device that does not include an occlusion member (e.g., 658) can alternatively be inserted through the second lumen of the second catheter 670 and into a side branch, a portion of a bifurcated vessel or other body lumen. For example, it may be desirable to use the second lumen and side port of the second (outer) catheter 670 to introduce a device, such as, an infusion catheter device for injecting a therapeutic material into the side branch or portion of the bifurcated vessel. In another example, a device can be inserted through the second catheter and out the side port that is configured to introduce or deposit a coil or plug into a side branch of a main vessel to, for example, permanently occlude the side branch. In other cases, devices such as, an imaging device, a guide wire, or any other suitable medical device can be inserted through the second catheter and side port and into a side branch or portion of a bifurcated vessel as described herein. In other words, the catheter assembly 600 can be used to introduce various other devices through the catheter device 600 and into a side branch or other body lumen using the side port as described herein.

FIGS. 33-40 illustrate a catheter system 715, according to an embodiment. The catheter system 715 includes a catheter assembly 700 and a secondary catheter 790. The catheter system 715 includes multiple occlusion members or elements that can be used to occlude one or more portions of a body lumen such as for example, an artery or vessel within a patient. The catheter assembly 700 (also referred to herein as "catheter device") can include the same or similar features and function the same or similar to the catheter devices described above (e.g., 100, 200, 300, 400, 600). The catheter assembly 700 includes a first catheter 760 (also referred to herein as "inner catheter") and a second catheter 770 (also referred to herein as "outer catheter").

A first occlusion member 768 is disposed at a distal end portion of the first catheter 760 and a second occlusion member 778 is disposed at a distal end portion of the second catheter 770. The occlusion members 768 and 778 can be any suitable device or mechanism that is configured to selectively limit, block, obstruct, or otherwise occlude a lumen (e.g., artery, vessel, vasculature) in which the occlusion member(s) 768 and 778 are disposed. The first occlusion member 768 and the second occlusion member can each be, for example, inflatable or expandable occlusion members such as the balloon occlusion elements described above for dilation catheter 200. In some embodiments, the occlusion member 778 can be substantially similar to the occlusion member 768 of the first catheter 760 and in other embodiments, the first occlusion member 768 can have a different configuration or structure than the second occlusion member 778. The first occlusion member 768 and the second occlusion member 778 can each be moved between a collapsed configuration (also referred to as "retracted configuration") for insertion of the catheter device 700 into a body of a patient (e.g., into an artery, vessel or other body lumen) and an expanded configuration (also referred to as "dilated configuration" or "inflated configuration") for occluding a portion of a body lumen (e.g., artery, vessel). The first and second occlusion members 768 and 778 when in the collapsed configuration have a smaller outer perimeter (or diameter) than when in the expanded configuration.

The catheter device 700 can include some or all of the various other features and functions described above for other embodiments of a catheter device (e.g. catheter devices 100, 200, 300, 400) and therefore some features and functions are not described in detail with respect to catheter device 700. For example, the catheter device 700 can include a handle (not shown) with controls and actuators that can be used to operate the catheter device 700 as described for previous embodiments.

As described above for previous embodiments, the second catheter 770 can be moved relative to the first catheter 760, or vice-versa, to adjust a distance between the first occlusion member 768 and the second occlusion member 778. The catheter device 700 can be used to isolate a segment of a bodily lumen within the space defined between the first occlusion member 768 and the second occlusion member 778. Thus, a procedure can then be performed within the isolated segment such as for example, delivering a therapeutic material/agent to the isolated segment. For example, as shown in FIG. 33, the catheter device 700 can be positioned within a first target vessel TV1 with the first occlusion member 768 disposed at a distance from the second occlusion member 778.

More specifically, as with the previously described embodiments of a catheter device, the second catheter 770 defines a first lumen 773 (see FIGS. 37-40) configured to movably receive the first catheter 760 such that the first catheter 760 and the second catheter 770 can be moved relative to each other and a distance between the first occlusion member 768 and the second occlusion member 778 can be adjusted. The catheter device 700 can also include a seal element 785 (see FIG. 34B) (also referred to as a "seal", "sealing element", "selective sealing element", or "filter-ring") disposed at or near a distal end of the second catheter 770. For example, the seal element 785 can be disposed within the first lumen 773 near a distal opening (see FIGS. 34A and 34B) that is in fluid communication with the first lumen 773 and disposed in sealing engagement with an outer surface of the first catheter 760. The seal element 785 can prevent the entry of cells and or biologics that have been injected into a body lumen (e.g., from an infusion port described below) from flowing back into the first lumen 773 of the second catheter 770. By doing so, a maximum number of cells can be delivered to the treatment area, and improve engraftment efficiency. The seal element 785 can be for example, a ring, a membrane, a one-way valve, or other known sealing elements used in medical devices. The second catheter 770 can also define an inflation lumen 774 (see FIGS. 39 and 40) in fluid communication with an inflation port 775 that can be used to communicate an inflation medium to and from the second occlusion member 778.

Figure 35:
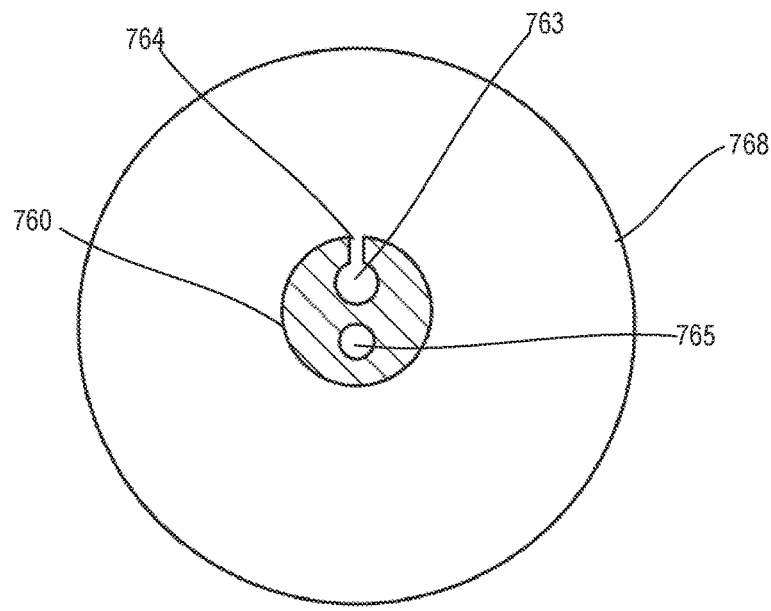
FIG. 35 is a cross-sectional view taken along line 35-35 in FIG. 33.
Figure 36:
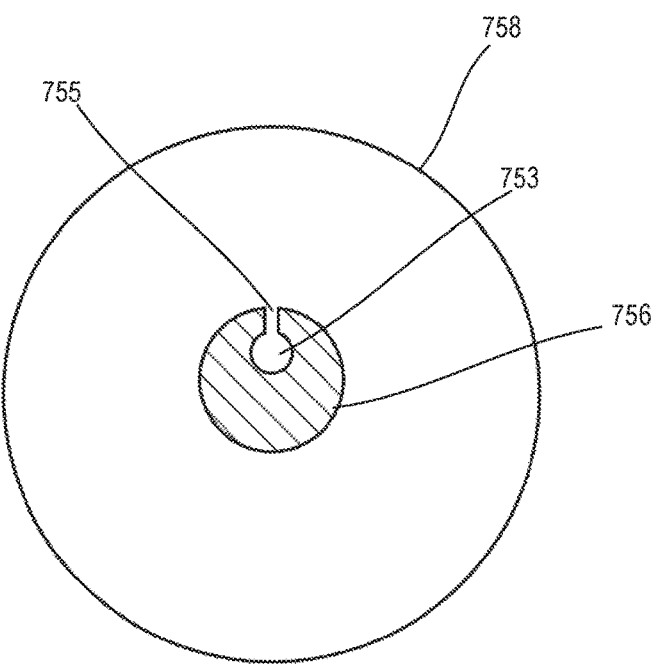
FIG. 36 is a cross-sectional view taken along line 36-36 in FIG. 33.
Figure 37:
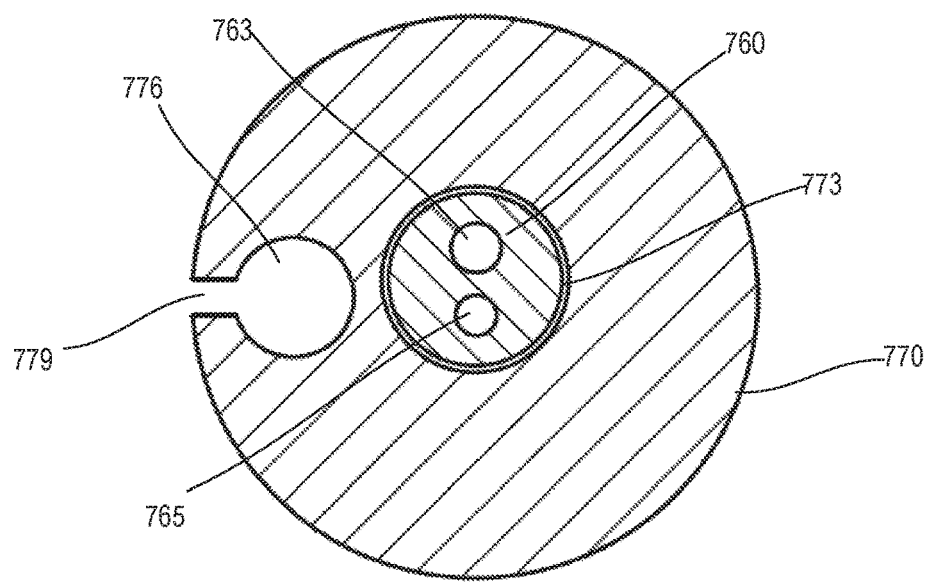
FIG. 37 is a cross-sectional view taken along line 37-37 in FIG. 34A.
Figure 38:
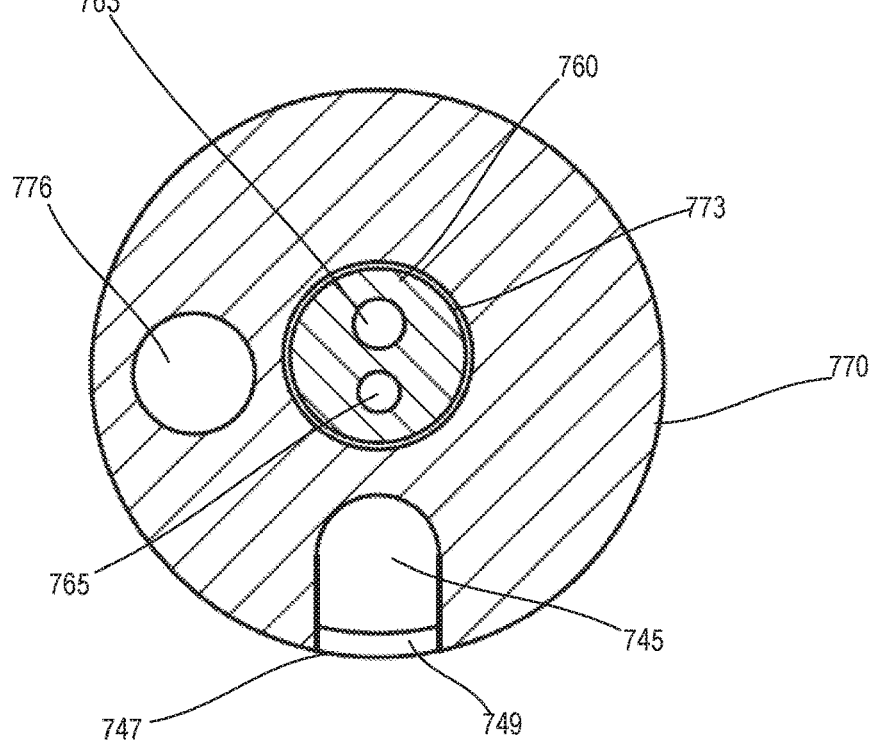
FIG. 38 is a cross-sectional view taken along line 38-38 in FIG. 34A.
Figure 39:
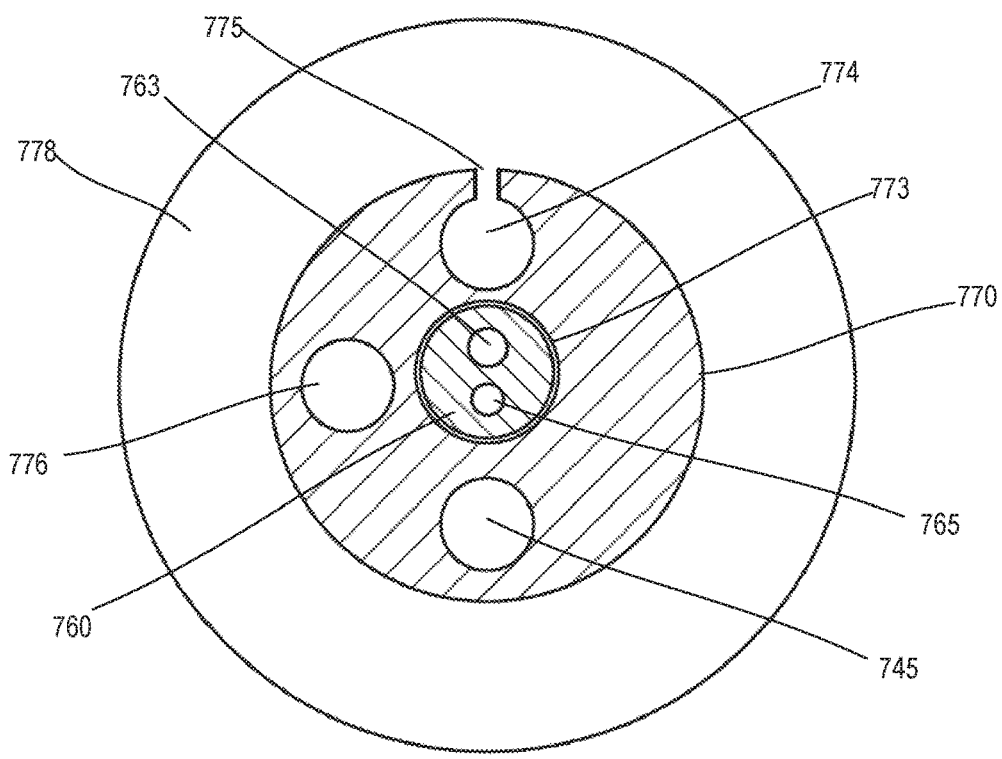
FIG. 39 is a cross-sectional view taken along line 39-39 in FIG. 34A.
Figure 40:
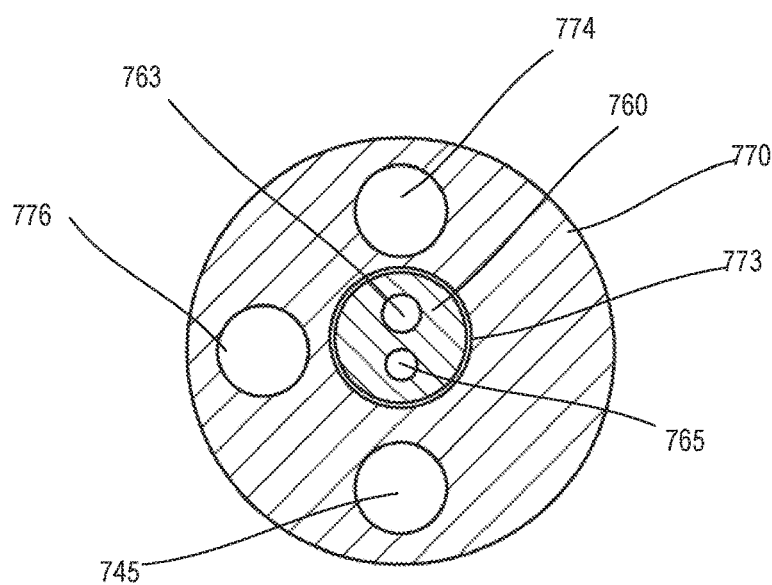
FIG. 40 is a cross-sectional view taken along line 49-40 in FIG. 34A.

The first catheter 760 can define a guidewire lumen 765 (see FIGS. 35 and 37-40) and an inflation lumen 763 (see FIGS. 35 and 37-40) in fluid communication with an inflation port 764 (see FIG. 35). The guidewire lumen 765 can be used to insert and receive a guidewire (not shown) therethrough, as described above for previous embodiments. The inflation lumen 763 can be used to communicate an inflation medium to and from the first occlusion member 768.

In this embodiment, the second catheter 770 also defines an infusion lumen 776 in fluid communication with an infusion port 779 (see FIG. 37) that can be used to communicate a therapeutic material to a selected target region within the patient. The infusion port 779 is defined on a side wall of the second catheter 770. As shown in FIG. 33, the infusion port 779 is disposed between the first occlusion member 768 and the second occlusion member 778. Thus, when the occlusion members 768 and 778 are deployed within a body lumen (e.g., TV1) of a patient to isolate a target region within the body lumen, the infusion port 779 can be used to communicate a therapeutic material to the isolated region. The second catheter 770 also defines a second lumen 745 (see FIGS. 34B and 38-40) and a side port 747 that is in fluid communication with the second lumen 745 (see FIGS. 34B and 38). The second lumen 745 can receive the secondary catheter assembly 790 therein as described in more detail below.

The secondary catheter 790 includes a third catheter 756 and a third occlusion member 758 disposed at a distal end portion of the third catheter 756. The third occlusion member 758 can be any suitable device or mechanism that is configured to selectively limit, block, obstruct, or otherwise occlude a lumen (e.g., artery, vessel, vasculature) in which the occlusion member 758 is disposed. For example, the third occlusion member 758 can be inflatable or expandable. The third catheter 756 defines an inflation lumen 753 in fluid communication with an inflation port 755 (see FIG. 36) that can be used to communicate an inflation medium to and from the third occlusion member 758. As described above, the secondary catheter 790 can be movably disposed within the second lumen 745 of the second catheter 770 and out the side port 747 defined by the second catheter 770 as shown in FIG. 33.

The second catheter 770 can also include a second seal 749 (see FIGS. 33, 34B and 38) that can be disposed within the second lumen 745 near the side port 747 and be configure to be disposed about an outer surface of the third catheter 756 when inserted therethrough. As with the seal element 785 described above disposed within the first lumen 773 of the second catheter 770, the second seal 749 disposed in the second lumen 745 can prevent the entry of cells and or biologics that have been injected into a body lumen from flowing back into the second lumen. The second seal 749 within the second lumen 745 of the second catheter 770 can be for example, a ring, a membrane or other known sealing elements used in medical devices.

In use, as described for previous embodiments, the catheter device 700 can be inserted into a body lumen (e.g., an artery, vessel, portion of a vasculature) such as the first target vessel TV1 shown in FIG. 33, with the first and second occlusion members 768 and 778 both in a collapsed configuration (not shown). The first and second occlusion members 768 and 778 can be positioned within the first target vessel TV1 at a desired location and then moved to their expanded configuration (e.g., inflated) to occlude the first target vessel TV1 to define an isolated target region between the first occlusion member 768 and the second occlusion member 778. As described above, and as shown in FIG. 33, the infusion port 779 is disposed between the first occlusion member 768 and the second occlusion member 778 and can be used to introduce a therapeutic material to the isolated portion of the body lumen as described above for previous embodiments.

In this example embodiment, the target vessel TV1 is a main vessel and a branch target vessel TV2 (e.g., second body lumen) is in fluid communication with the main vessel TV1 as shown in FIG. 33. After the catheter device 700 has been deployed in the main or first target vessel TV1, the secondary catheter 790, with the third occlusion member 758 in a collapsed configuration, can be inserted through the second lumen 745 of the second catheter 770, out the side port 747 and positioned within the branch target vessel TV2. For example, as shown in FIG. 33, in this example, the secondary catheter 790 exits the side port 747 at an angle of substantially 90 degrees, however, it should be understood that the secondary catheter 790 can exit the side port 747 at other angles as needed. When the third occlusion member 758 is disposed at a desired target location within the second target vessel TV2, the third occlusion member 758 can be deployed (e.g., expanded, inflated) to occlude a portion of the second target vessel TV2 (i.e., branch vessel). Thus, in such a case, with the third occlusion member 758 expanded, the first occlusion member 768, the second occlusion member 778 and the third occlusion member 758 collectively define an isolated target region TR to be treated that includes a portion of the first target vessel TV (e.g., main vessel) and a portion of the second target vessel TV2 (e.g., branch vessel). In other words, the occluded target region TR spans between the first target vessel TV1 (e.g., main vessel) and the second target vessel TV2 (e.g., branch vessel). A therapeutic material can then be injected through the infusion lumen 776 and out of the infusion port 779 into the isolated target region TR.

Figure 41:
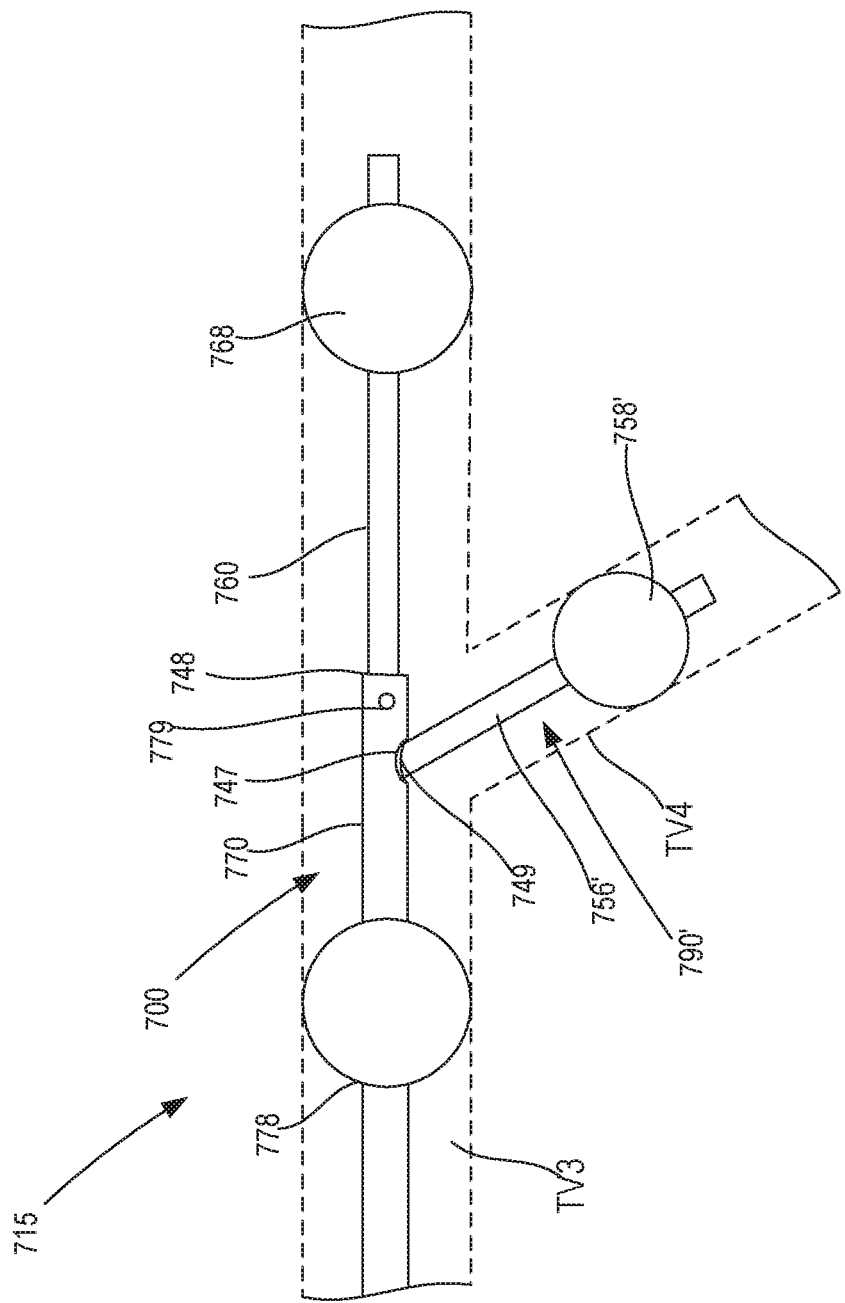
FIG. 41 is a side view of a catheter system according to an embodiment, shown deployed within a bifurcated vessel.

FIG. 41 illustrates a catheter system 715' that includes the catheter device 700 and a secondary catheter 790'. In this embodiment, the secondary catheter 790' includes a third catheter 756' and a third occlusion member 758'. In this example, the third occlusion member 758' is larger in an expanded configuration than the occlusion member 758 shown in FIG. 33 for use, for example, in a larger vessel. In this example, the catheter system 715' is being used within a bifurcated vessel that includes a first body lumen portion (e.g. target vessel or artery) TV3 and a second body lumen portion (e.g., target vessel or artery) TV4. As shown in FIG. 41, in this example use, the secondary catheter 790' exits the second lumen 745 of the second catheter 770 at an angle less than 90 degrees, however, it should be understood that the secondary catheter 790' can exit the side port 747 at other angles as needed.

As described above, in some embodiments, the catheter (e.g., 756, 756') of a secondary catheter device (e.g., 790, 790') can define an infusion port in addition to or alternatively to the infusion port (e.g., 779) on the second catheter (e.g., 770). FIG. 42 illustrates such an embodiment disposed within a bifurcated vessel. A catheter system 815 includes a catheter assembly or device 800 and a secondary catheter 890. The catheter device 800 can be constructed the same as or similar to and function the same as or similar to the catheter device 790 described above, and therefore, some details are not described with respect to this embodiment. The catheter device 800 includes a first catheter 860 (also referred to as "inner catheter") with a first occlusion member 868 disposed on a distal end portion, and a second catheter 870 (also referred to herein as "outer catheter") having a second occlusion member 878 disposed on a distal end portion. The occlusion members 868 and 878 can be any suitable device or mechanism that is configured to selectively limit, block, obstruct, or otherwise occlude a lumen (e.g., artery, vessel, vasculature) in which the occlusion member(s) 868 and 878 are disposed. The first occlusion member 868 and the second occlusion member 878 can each be, for example, inflatable or expandable occlusion members such as the balloon occlusion elements described above for dilation catheter 200. The first occlusion member 868 and the second occlusion member 878 can each be moved between a collapsed configuration (also referred to as "retracted configuration") for insertion of the catheter device 800 into a body of a patient (e.g., into an artery, vessel or other body lumen) and an expanded configuration (also referred to as "dilated configuration" or "inflated configuration") for occluding a portion of a body lumen (e.g., artery, vessel).

The first catheter 860 is movably disposed within a first lumen (not shown) of the second catheter 870 in the same manner as described above for catheter device 700. More specifically, as with the previously described embodiments of a catheter device, the first catheter 860 and the second catheter 870 can be moved relative to each other and a distance between the first occlusion member 868 and the second occlusion member 878 can be adjusted. The catheter device 800 can also include a seal element (not shown) disposed at or near a distal end of the second catheter 870. The seal element can prevent the entry of cells and or biologics that have been injected into a body lumen (e.g., from an infusion port described below) from flowing back into the first lumen of the second catheter 870. The second catheter 870 also defines an inflation lumen (not shown) in fluid communication with an inflation port (not shown) that can be used to communicate an inflation medium to and from the second occlusion member 878.

The second catheter 870 also defines an infusion lumen (not shown) in fluid communication with an infusion port 879 that can be used to communicate a therapeutic material to a selected target region within the patient as described above for previous embodiments. The infusion port 879 is defined on a side wall of the second catheter 870. The second catheter 870 also defines a second lumen (not shown) and a side port 847 that is in fluid communication with the second lumen. The second lumen can receive the secondary catheter assembly 890 therein as described above for previous embodiments. A second seal 849 can be disposed within the second lumen near the side port 847. The second seal 849 can be, for example, a one-way valve and can prevent the entry of cells and or biologics that have been injected into a body lumen from flowing back into the second lumen of the second catheter 870.

The first catheter 860 can define a guidewire lumen (not shown) and an inflation lumen (not shown) in fluid communication with an inflation port (not shown). The guidewire lumen can be used to insert and receive a guidewire (not shown) therethrough, as described above for previous embodiments. The inflation lumen can be used to communicate an inflation medium to and from the first occlusion member 868.

The secondary catheter 890 includes a third catheter 856 and a third occlusion member 858 disposed at a distal end portion of the third catheter 856. The third occlusion member 858 can be any suitable device or mechanism configured to selectively limit, block, obstruct, or otherwise occlude a lumen (e.g., artery, vessel, vasculature) in which the occlusion member 858 is disposed. In this embodiment, the third occlusion member 858 is inflatable and can be moved between a collapsed configuration for delivery into a body lumen and an expanded configuration to occlude a body lumen.

As shown in FIG. 43, the third catheter 856 defines an inflation lumen 853 in fluid communication with an inflation port (not shown) that can be used to communicate an inflation medium to and from the third occlusion member 858. In this embodiment, the third catheter 856 also defines an infusion lumen 838 in fluid communication with an infusion port 839. As with the infusion lumen 776 and infusion port 779 described above for catheter device 700, the infusion lumen 838 and infusion port 839 can be used to inject a therapeutic material into an isolated region of a body lumen as described in more detail below. As described above, the secondary catheter assembly 890 can be movably disposed within the second lumen of the second catheter 870 and out the side port 847 defined by the second catheter 870 as shown in FIG. 42.

In use, as described for previous embodiments, the catheter device 800 can be inserted into a body lumen (e.g., an artery, vessel, portion of a vasculature) such as a first target vessel TV3 shown in FIG. 42, with the first and second occlusion members 868 and 878 both in a collapsed configuration (not shown). In this example, the first target vessel TV3 is a first portion of a bifurcated vessel. The first and second occlusion members 868 and 878 can be positioned within the first target vessel TV3 at a desired location and then moved to their expanded configuration (e.g., inflated) to occlude the first target vessel TV3 to define an isolated target region as shown in FIG. 42. As described above, and as shown in FIG. 42, the infusion port 879 is disposed between the first occlusion member 868 and the second occlusion member 878 and can be used to introduce a therapeutic material to the isolated portion of the body lumen TV3 as described above for previous embodiments.

As described above, the first target vessel TV3 is part of a bifurcated vessel which includes a second target vessel TV4 (i.e., second body lumen). After the catheter device 800 has been deployed in the first target vessel TV3, the secondary catheter 890, with the third occlusion member 858 in a collapsed configuration, can be inserted through the second lumen of the second catheter 870, out the side port 847 and positioned within the second target vessel TV4. As shown in FIG. 42, in this example, the secondary catheter 890 exits the side port 847 at an angle less than 90 degrees, however, it should be understood that the secondary catheter 890 can exit the side port 847 at other angles as needed. When the third occlusion member 858 is disposed at a desired target location within the second target vessel TV4, the third occlusion member 858 can be deployed (e.g., expanded, inflated) to occlude a portion of the second target vessel TV4. Thus, with the third occlusion member 858 expanded, the first occlusion member 868, the second occlusion member 878 and the third occlusion member 858 collectively define an isolated target region TR to be treated that includes a portion of the first target vessel TV3 (i.e., first body lumen) and a portion of the second target vessel TV4 (i.e., second body lumen). In other words, the occluded target region TR spans between the first target vessel TV3 and the second target vessel TV4.

In this embodiment, a therapeutic material can be injected through the infusion lumen and out of the infusion port 879 of the second catheter 870 and into the target region TR. A therapeutic material can also be injected through the infusion lumen 838 and infusion port 839 of the third catheter 856 and into the second target vessel TV4. In some cases, the same therapeutic material can be injected through both infusion ports, 879, 839. In some cases, it may be desirable to inject a first therapeutic material through the infusion port 879 and a second different therapeutic material through the infusion port 839.

Figure 44:
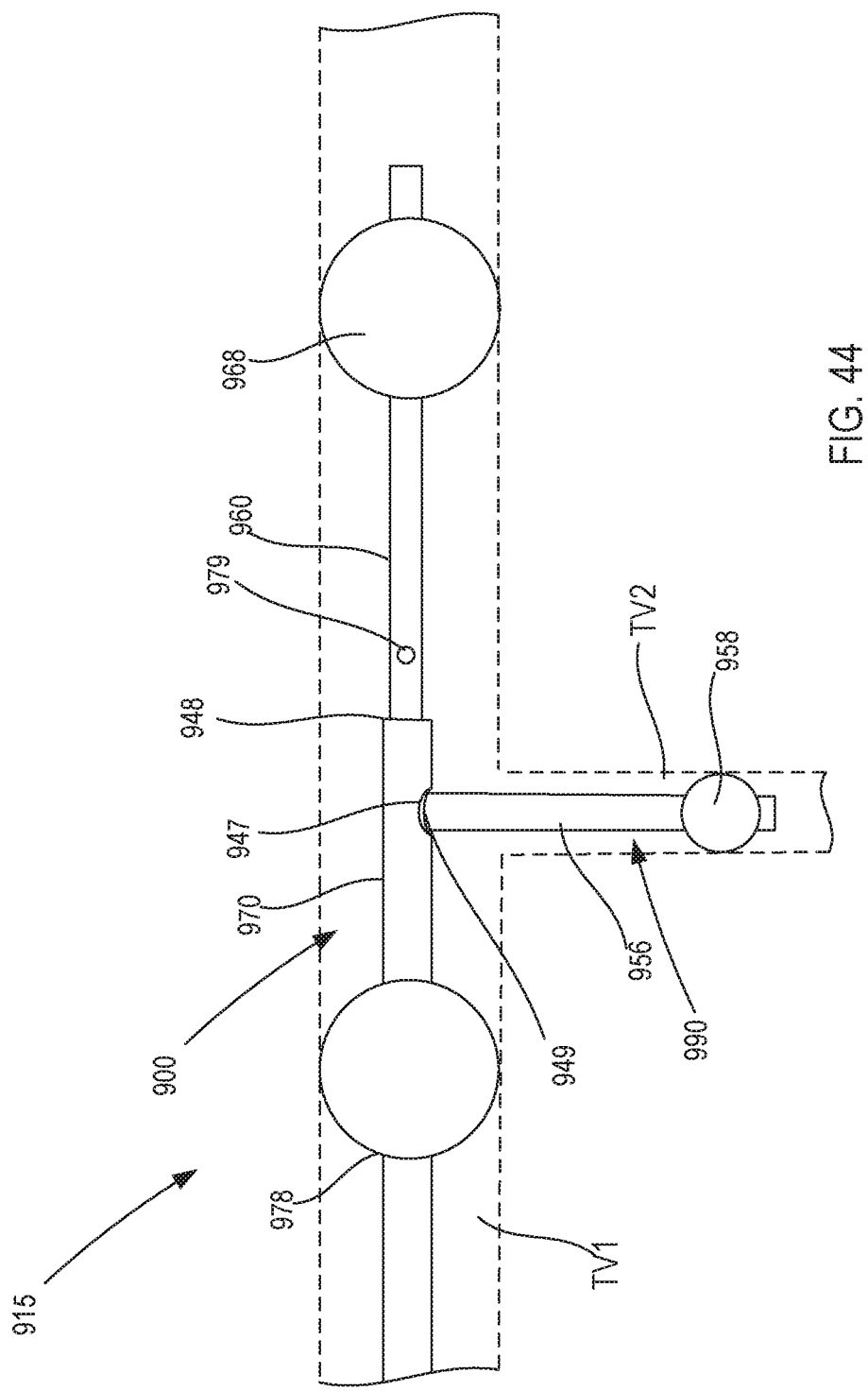
FIG. 44 is a side view of a portion of a catheter system, according to another embodiment, shown deployed within a main vessel and a side branch of the main vessel.

FIG. 44 illustrates another embodiment of a catheter system that can be used to occlude a body lumen. A catheter system 915 includes a catheter assembly 900 and a secondary catheter assembly 990. The catheter device 900 can be constructed the same as or similar to and function the same as or similar to the catheter devices (e.g., 790, 890) described above and therefore, some details are not described with respect to this embodiment. The catheter device 900 includes a first catheter 960 (also referred to as "inner catheter") with a first occlusion member 968 disposed on a distal end portion, and a second catheter 970 (also referred to herein as "outer catheter") having a second occlusion member 978 disposed on a distal end portion. The occlusion members 968 and 978 can be any suitable device or mechanism that is configured to selectively limit, block, obstruct, or otherwise occlude a lumen (e.g., artery, vessel, vasculature) in which the occlusion member(s) 968 and 978 are disposed. The first occlusion member 968 and the second occlusion member 978 can each be, for example, inflatable or expandable and can each be moved between a collapsed configuration (also referred to as "retracted configuration") for insertion of the catheter device 900 into a body of a patient (e.g., into an artery, vessel or other body lumen) and an expanded configuration (also referred to as "dilated configuration" or "inflated configuration") for occluding a portion of a body lumen (e.g., artery, vessel).

The first catheter 960 is movably disposed within a first lumen (not shown) of the second catheter 970 in the same manner as described above for catheter device 700. More specifically, as with the previously described embodiments of a catheter device, the first catheter 960 and the second catheter 970 can be moved relative to each other and a distance between the first occlusion member 968 and the second occlusion member 978 can be adjusted. The catheter device 900 can also include a seal element (not shown) disposed at or near a distal end of the second catheter 970. The seal element can prevent the entry of cells, biologics or other therapeutic materials, etc. that have been injected into a body lumen (e.g., from an infusion port described below) from flowing back into the first lumen of the second catheter 970. The second catheter 970 also defines an inflation lumen (not shown) in fluid communication with an inflation port (not shown) that can be used to communicate an inflation medium to and from the second occlusion member 978.

The second catheter 970 also defines a second lumen (not shown) and a side port 947 that is in fluid communication with the second lumen. The second lumen can receive the secondary catheter assembly 990 therein as described above for previous embodiments. A second seal 949 can be disposed within the second lumen near the side port 947. The second seal 949 can prevent the entry of cells, biologics or other therapeutic materials that have been injected into a body lumen from flowing back into the second lumen of the second catheter 970.

As shown in FIG. 44, the first catheter 960 defines a guidewire lumen (not shown) and an inflation lumen (not shown) in fluid communication with an inflation port (not shown). The guidewire lumen can be used to insert and receive a guidewire (not shown) therethrough, as described above for previous embodiments. The inflation lumen can be used to communicate an inflation medium to and from the first occlusion member 968. In this embodiment, the first catheter 960 also defines an infusion lumen (not shown) in fluid communication with an infusion port 979. As with the infusion lumen 776 and infusion port 779 described above for catheter device 700, the infusion lumen of the first catheter 960 and infusion port 979 can be used to inject a therapeutic material into an isolated region of a body lumen as described in more detail below.

The secondary catheter assembly 990 can be configured the same as, and function the same as, the secondary catheter assembly 790 described above. The secondary catheter assembly 990 includes a third catheter 956 and a third occlusion member 958 disposed at a distal end portion of the third catheter 956. The third occlusion member 958 can be any suitable device or mechanism configured to selectively limit, block, obstruct, or otherwise occlude a lumen (e.g., artery, vessel, vasculature) in which the occlusion member 958 is disposed. In this embodiment, the third occlusion member 958 is inflatable and can be moved between a collapsed configuration for delivery into a body lumen and an expanded configuration to occlude a body lumen. As described above for previous embodiments, the secondary catheter assembly 990 can be movably disposed within the second lumen of the second catheter 970 and out the side port 947 defined by the second catheter 970 as shown in FIG. 44.

In use, as described for previous embodiments, the catheter device 900 can be inserted into a first body lumen (e.g., an artery, vessel, portion of a vasculature) such as a first target vessel TV1 shown in FIG. 44, with the first and second occlusion members 968 and 978 both in a collapsed configuration (not shown). In this example, the first target vessel TV1 (i.e., first body lumen) is a main vessel, and a second target vessel TV2 (i.e., second body lumen) is a branch of the main vessel. The first and second occlusion members 968 and 978 can be positioned within the first target vessel TV1 at a desired location and then moved to their expanded configuration (e.g., inflated) to occlude the first target vessel TV1 and define an isolated target region within the first target vessel TV1. As shown in FIG. 44, the infusion port 979 is disposed between the first occlusion member 968 and the second occlusion member 978 and can be used to introduce a therapeutic material to the isolated portion of the first target vessel TV1 as described above for previous embodiments.

After the catheter device 900 has been deployed in the first target vessel TV1, the secondary catheter 990, with the third occlusion member 958 in a collapsed configuration, can be inserted through the second lumen of the second catheter 970, out the side port 947 and positioned within the second target vessel TV2 (e.g., branch vessel). As shown in FIG. 44, in this example, the secondary catheter 990 exits the side port 947 at an angle substantially equal to 90 degrees, however, it should be understood that the secondary catheter 990 can exit the side port 947 at other angles as needed. When the third occlusion member 958 is disposed at a desired target location within the second target vessel TV2, the third occlusion member 958 can be deployed (e.g., expanded, inflated) to occlude a portion of the second target vessel TV2. Thus, with the third occlusion member 958 expanded, the first occlusion member 968, the second occlusion member 978 and the third occlusion member 958 collectively define an isolated target region TR to be treated that includes a portion of the first target vessel TV1 (i.e., first body lumen) and a portion of the second target vessel TV2 (i.e., second body lumen). In other words, the occluded target region TR spans between the first target vessel TV1 and the second target vessel TV2. A therapeutic material can then be injected through the infusion lumen and out of the infusion port 979 of the first catheter 960 and into the target region TR.

Figure 45:
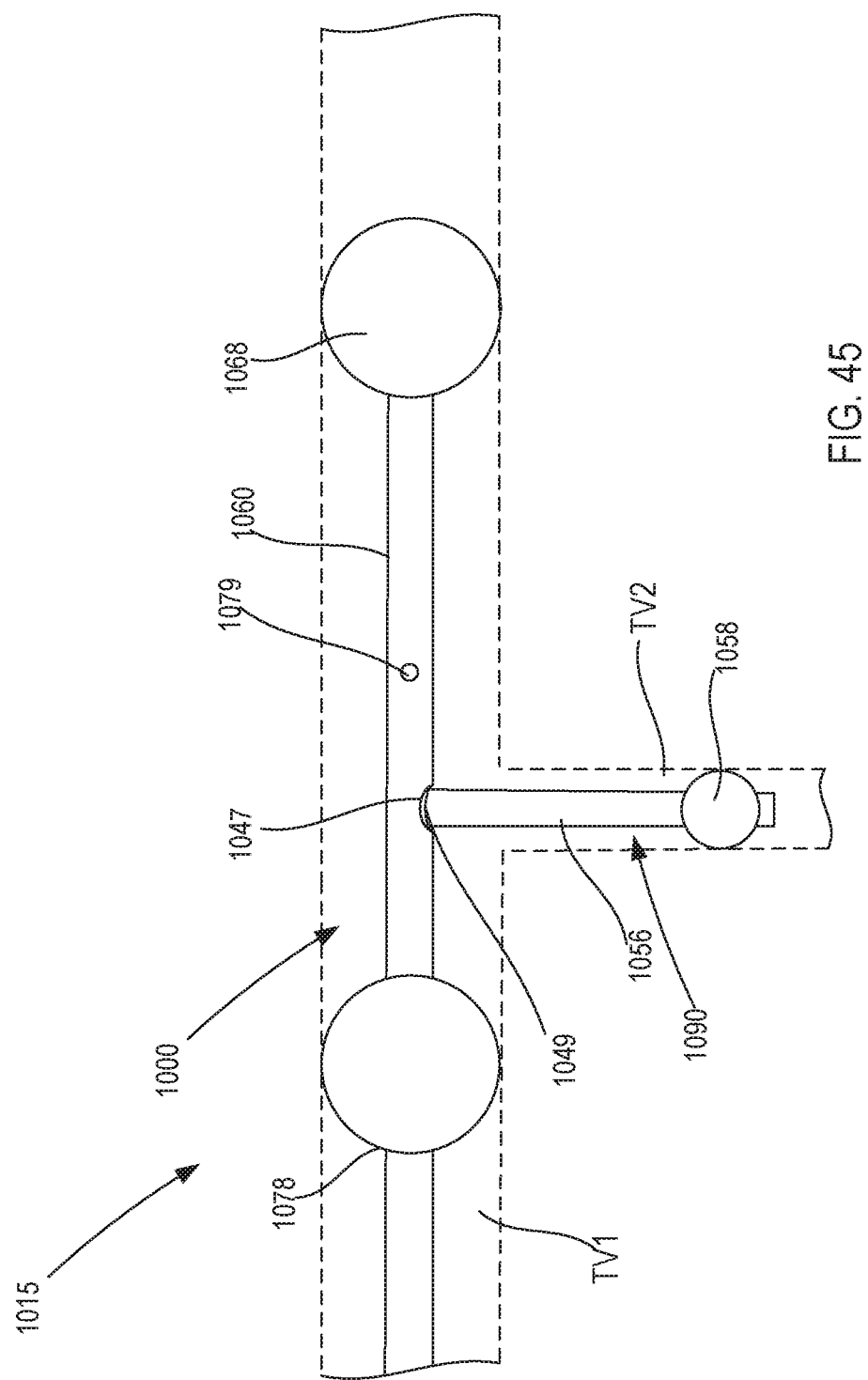
FIG. 45 is a side view of a portion of a catheter system, according to another embodiment, shown deployed within a main vessel and a side branch of the main vessel.

FIG. 45 illustrates another embodiment of a catheter system that can be used to occlude a body lumen to define an isolated region to introduce a treatment agent or material therein. A catheter system 1015 includes a catheter assembly 1000 that includes a catheter 1060 that has a first occlusion member 1068 disposed on a distal end portion, and a second occlusion member 1078 disposed proximal to the first occlusion member 1068 at a spaced distance from the first occlusion member 1068. The occlusion members 1068 and 1078 can be any suitable device or mechanism that is configured to selectively limit, block, obstruct, or otherwise occlude a lumen (e.g., artery, vessel, vasculature) in which the occlusion member(s) 1068 and 1078 are disposed. The first occlusion member 1068 and the second occlusion member 1078 can each be, for example, inflatable or expandable and can each be moved between a collapsed configuration (also referred to as "retracted configuration") for insertion of the catheter device 1000 into a body of a patient (e.g., into an artery, vessel or other body lumen) and an expanded configuration (also referred to as "dilated configuration" or "inflated configuration") for occluding a portion of a body lumen (e.g., artery, vessel).

In this embodiment, the first occlusion member 1068 and the second occlusion member 1078 are disposed in a fixed position on the catheter 1060. In other words, the first occlusion member 1068 and the second occlusion member 1078 are not movable relative to each other and are not adjustable. In this embodiment, the catheter 1060 can define an inflation lumen (not shown) in fluid communication with an inflation port (not shown) that can be used to communicate an inflation medium to and from the first occlusion member 1068, and an inflation lumen (not shown) in fluid communication with an inflation port (not shown) that can be used to communicate an inflation medium to and from the second occlusion member 1078. The catheter 1060 also defines a guidewire lumen (not shown) that can be used to insert and receive a guidewire (not shown) therethrough, as described above for previous embodiments.

The catheter 1060 also defines an infusion lumen (not shown) in fluid communication with an infusion port 1079 and a secondary device lumen (not shown) and a side port 1047 that is in fluid communication with the secondary device lumen. As with the infusion lumen 776 and infusion port 779 described above for catheter device 700, the infusion lumen of the catheter 1060 and infusion port 1079 can be used to inject a therapeutic material into an isolated region of a body lumen as described in more detail below. The secondary device lumen and the side port 1047 can receive a secondary catheter assembly 1090 therethrough as described above for previous embodiments. A seal 1049 can be disposed within the secondary device lumen near the side port 1047. The seal 1049 can prevent the entry of cells, biologics, therapeutic materials, etc. that have been injected into a body lumen from flowing back into the secondary device lumen of the catheter 1060.

The secondary catheter assembly 1090 can be configured the same as, and function the same as, the secondary catheter assembly 790 described above. The secondary catheter assembly 1090 includes a catheter 1056 and a third occlusion member 1058 disposed at a distal end portion of the catheter 1056. The third occlusion member 1058 can be any suitable device or mechanism configured to selectively limit, block, obstruct, or otherwise occlude a lumen (e.g., artery, vessel, vasculature) in which the occlusion member 1058 is disposed. In this embodiment, the third occlusion member 1058 is inflatable and can be moved between a collapsed configuration for delivery into a body lumen and an expanded configuration to occlude a body lumen. As described above for previous embodiments, the secondary catheter assembly 1090 can be movably disposed through the secondary device lumen of the catheter 1060 and out the side port 1047 defined by the catheter 1060 as shown in FIG. 45.

In use, as described for previous embodiments, the catheter device 1000 can be inserted into a first body lumen (e.g., an artery, vessel, portion of a vasculature) such as a first target vessel TV1 shown in FIG. 45, with the first and second occlusion members 1068 and 1078 both in a collapsed configuration (not shown). In this example, the first target vessel TV1 (i.e., first body lumen) is a main vessel, and a second target vessel TV2 (i.e., second body lumen) is a side branch of the main vessel. The first and second occlusion members 1068 and 1078 can be positioned within the first target vessel TV1 at a desired location to define an isolated target region within the first target vessel TV1. As shown in FIG. 45, the infusion port 1079 is disposed between the first occlusion member 1068 and the second occlusion member 1078 and can be used to introduce a therapeutic material/agent to the isolated portion of the first target vessel TV1 as described above for previous embodiments.

After the catheter device 1000 has been deployed in the first target vessel TV1, the secondary catheter 1090, with the third occlusion member 1058 in a collapsed configuration, can be inserted through the secondary lumen of the catheter 1060, out the side port 1047 and positioned within the second target vessel TV2 (e.g., branch vessel). As shown in FIG. 45, in this example, the secondary catheter 1090 exits the side port 1047 at an angle substantially equal to 90 degrees, however, it should be understood that the secondary catheter 1090 can exit the side port 1047 at other angles as needed. When the third occlusion member 1058 is disposed at a desired target location within the second target vessel TV2, the third occlusion member 1058 can be deployed (e.g., expanded, inflated) to occlude a portion of the second target vessel TV2. Thus, with the third occlusion member 1058 expanded, the first occlusion member 1068, the second occlusion member 1078 and the third occlusion member 1058 collectively define an isolated target region TR to be treated that includes a portion of the first target vessel TV1 (i.e., first body lumen) and a portion of the second target vessel TV2 (i.e., second body lumen). In other words, the occluded target region TR spans between the first target vessel TV1 and the second target vessel TV2. A therapeutic material can then be injected through the infusion lumen and out of the infusion port 1079 of the catheter 1060 and into the target region TR.

Figure 46:
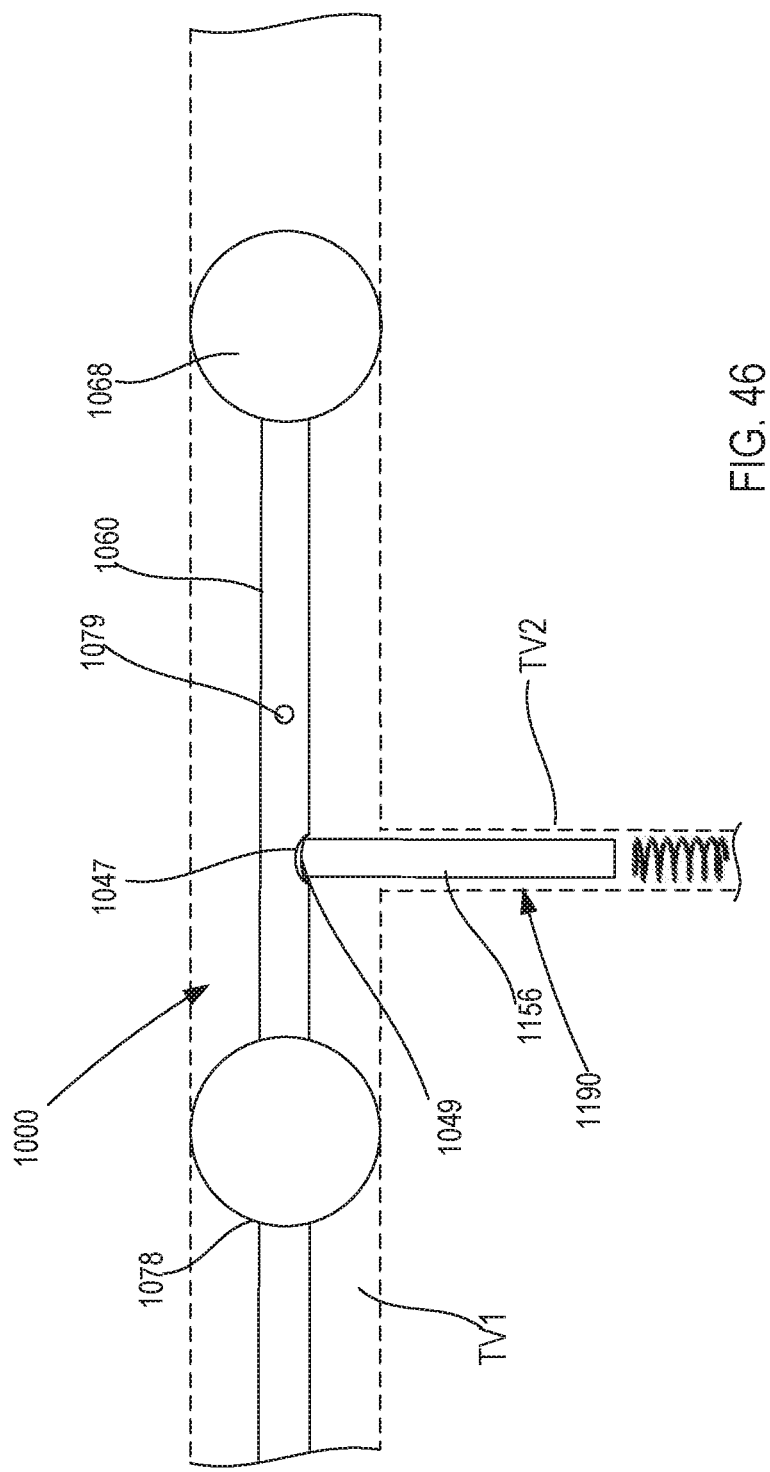
Figure 47:
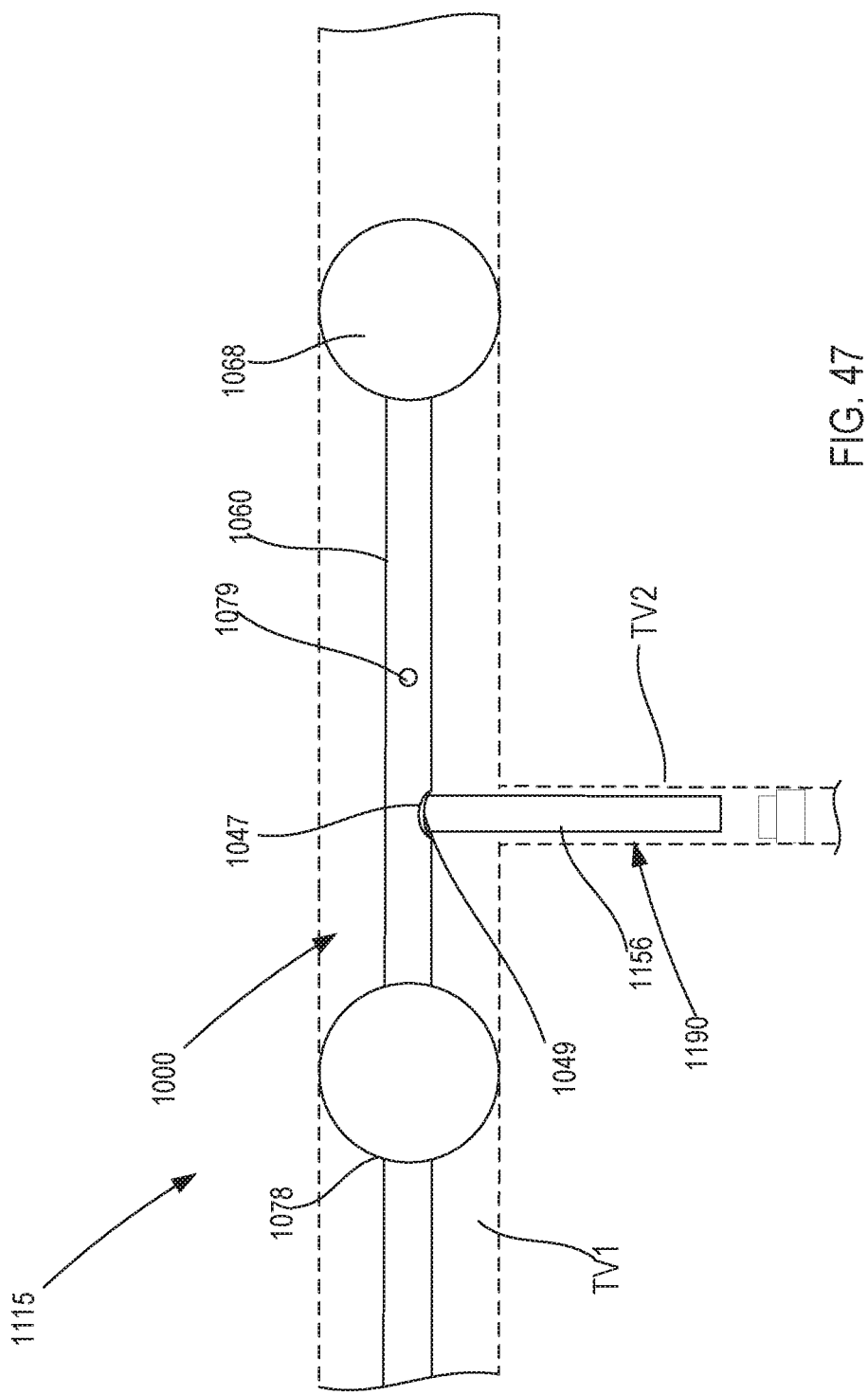

FIGS. 46 and 47 each illustrate the catheter assembly 1000 described above, and a secondary treatment catheter 1190 that does not include an occlusion member. In this embodiment, the secondary catheter assembly 1190 can include a catheter 1156 that can be, for example, a micro catheter, that can be used to deliver a permanent occlusion member such as a coil or plug. As shown in FIG. 46, the catheter assembly 1000 is used to occlude and isolate a region of a first target vessel TV1. The side port 1047 is positioned near a side branch vessel TV2 and the secondary treatment catheter 1190 is shown disposed outside the side port 1047 and within the side branch vessel TV2. In FIG. 46, the secondary treatment catheter 1190 has been used to deliver a coil 1191 to the side branch vessel TV2. The coil 1191 can be any known medical coil configured to be used to occlude a body lumen. In FIG. 47, the secondary treatment catheter 1190 has been used to deliver a medical plug 1192 to the side branch vessel TV2. The plug 1192 can be any known medical plug configured for use in occluding a body lumen.

In use, as described for previous embodiments, the catheter device 1000 can be inserted into a first body lumen (e.g., an artery, vessel, portion of a vasculature) such as a first target vessel TV1 shown in FIGS. 46 and 47, with the first and second occlusion members 1068 and 1078 both in a collapsed configuration (not shown). The first and second occlusion members 1068 and 1078 can be positioned within the first target vessel TV1 at a desired location to define an isolated target region within the first target vessel TV1. As shown in FIGS. 46 and 47, the infusion port 1079 is disposed between the first occlusion member 1068 and the second occlusion member 1078 and can be used to introduce a therapeutic material/agent to the isolated portion of the first target vessel TV1 as described above for previous embodiments.

After the catheter device 1000 has been deployed in the first target vessel TV1, the secondary catheter 1190 can be inserted through the secondary lumen of the catheter 1060, out the side port 1047 and positioned within the second target vessel TV2 (e.g., side branch vessel). The secondary catheter 1190 can insert or deploy the coil 1191 (FIG. 46) or plug 1192 (FIG. 47) into the side branch vessel TV2 and the coil 1191 or plug 1192 can be used to occlude the side branch vessel TV2. Thus, with the coil 1191 or plug 1192 disposed within and occluding the side branch vessel TV2, an isolated region can be defined between the first occlusion member 1068, the second occlusion member 1078 and the coil 1191 or plug 1192. A therapeutic agent/material can then be injected through the infusion lumen and out of the infusion port 1079 of the catheter 1060 and into the target region TR. In some embodiments, a secondary catheter can be used as an infusion device to inject a therapeutic material into the side branch vessel TV2 as shown in FIG. 48.

FIG. 48 illustrates a secondary catheter assembly 1290 that includes a catheter 1256 that defines an infusion lumen in fluid communication with a distal opening 1257 that can be used to inject or introduce a therapeutic agent/material into the side branch vessel TV2. In alternative embodiments, the catheter 1256 can define an infusion port on a side wall of the catheter 1256 similar to infusion port 849 illustrated in FIG. 42.

In use, as described for previous embodiments, the catheter device 1000 can be inserted into a first body lumen (e.g., an artery, vessel, portion of a vasculature) such as a first target vessel TV1 shown in FIG. 48, with the first and second occlusion members 1068 and 1078 both in a collapsed configuration (not shown). The first and second occlusion members 1068 and 1078 can be positioned within the first target vessel TV1 at a desired location to define an isolated target region within the first target vessel TV1. As shown in FIG. 48, the infusion port 1079 is disposed between the first occlusion member 1068 and the second occlusion member 1078 and can be used to introduce a therapeutic material/agent to the isolated portion of the first target vessel TV1 as described above for previous embodiments.

After the catheter device 1000 has been deployed in the first target vessel TV1, the secondary catheter 1290 can be inserted through the secondary lumen of the catheter 1060, out the side port 1047 and positioned within the second target vessel TV2 (e.g., side branch vessel). The secondary catheter 1290 can inject/introduce a therapeutic agent/material into the side branch vessel TV2.

The devices described herein can also be provided in a kit. In some embodiments, a kit for use in the delivery of a biological agent to an area proximal to the pancreas can include, for example, one or more catheter devices or systems as described herein and one or more biologic/therapeutic agents for delivery to the pancreas. The catheter devices can include, for example, a proximal end portion, a distal end portion and one or more expandable devices, such as a balloon or a filter, associated therewith. In some embodiments, the catheter device can include a first catheter configured to be slidably received within a lumen of a second catheter, a first occlusion element coupled to the first catheter and a second occlusion element coupled to the second catheter. In such an embodiment, a distance between the first and second occlusion elements can be varied or adjusted. The occlusion elements can be expandable to engage a wall of a blood vessel thereby substantially isolating an interior region of the vessel between the first and second occlusion elements. Moreover, the first and second catheters can be configured such that at least one of the first and second catheters has a lumen configured to deliver a biological/therapeutic agent to the isolated interior region via an infusion port. The infusion port can allow for rapid and atraumatic delivery of cells/biologics into the isolated area. In some embodiments, a pressure regulator can be provided that is configured to regulate the fluid pressure of the agent or the materials used to dilate the occlusion element(s) (e.g., in a balloon embodiment).

In some embodiments, a kit can further include one or more biologic/therapeutic agents for delivery to the pancreas, a stylet(s); one or more catheters adapted and configured for accessing the pancreatic vessels; a dilator; a guidewire; a guide catheter; capsules for direct connection of biological materials/cells to the infusion port of the delivery catheter; a manometer to monitor the pressure in the isolated area; and/or a pump to regulate the infusion rate of cells/biologics.

In some embodiments, any of the components of a kit can be packaged together and collectively sold as a catheter device or can be packaged independently or in subgroups and sold together or separately. For example, in some embodiments, the handle 410 can be packaged independently from the first catheter 460 and the second catheter 470. Moreover, the first catheter 460 and the second catheter 470 can be packaged independent from one another or packaged together. As such, the handle 410 can be sold independent of the first catheter 460 and the second catheter 470. The first catheter 460 and the second catheter 470 can be sold independent of one another or together. Thus, in some embodiments, the handle 410 can be packaged independent of the first catheter 460 and the second catheter 470 and, prior to use, can be coupled to the first catheter 460 and the second catheter 470 such that the first set of ports 428 are in fluid communication with the corresponding lumen of the first catheter 460 and the second set of ports 443 are in fluid communication with the corresponding lumen of the second catheter 470. In some embodiments, the handle 410 can be, for example, reusable, while the first catheter 460 and the second catheter 470 are disposable. In other embodiments, the handle 410 can be coupled to the first catheter 460 and the second catheter 470 during, for example, a manufacturing process and packaged together to be sold as a complete catheter device.

In some embodiments, placement of the occlusion elements (e.g., the distal or first occlusion elements of members, the proximal or second occlusion elements or members and the lengths of each region therebetween can be varied based on the needs of the individual application. The occlusion catheter devices and systems described herein can retain sufficient trackability to allow advancement into the target region of the patient. In some embodiments, the catheter material can be flexible enough to traverse local anatomy yet have enough tensile strength to be able to be placed in position in place over a guidewire (e.g., the guidewire 280 and/or 380). Furthermore, for the first or inner catheters and the second or outer catheters to be slidable relative to each other in situ, various radial and tensile strengths can be incorporated in each.

Any of the catheters described herein can be fabricated of any material suitable for catheters, such as linear low density or high density polyethylene, nylon, polyurethane, polypropylene, silicone rubber, or other non-thrombogenic materials. In some embodiments, an outer catheter can be formed from a linear low-density polyethylene, while an inner catheter can be formed from a nylon. In some embodiments, the outer catheters described herein can be fabricated to include a structure for reinforcement (not shown), such as a metal braid or the like located between an inner and outer layer. The reinforcement structure can extend along any desired length of such outer catheters. In some embodiments, a reinforcement structure can extend along the entire length of an outer catheter.

In some embodiments, regions of a first catheter (i.e., an inner catheter) and/or the third catheters such as those described herein can also be fabricated in any manner that allows the relative stiffness of each region to vary. In some embodiments, an outer layer in each region of an outer catheter and/or an inner catheter can include a material with a different durometer measurement of hardness. For example, the material used in an intermediate region can be relatively harder than that used in a distal region, and the material used in a proximal region can be relatively harder than that used in the intermediate region. Other manners of varying the stiffness of an inner catheter and/or an outer catheter (i.e., a first catheter and a second catheter, respectively, such as those described herein) or a secondary or third catheter as described herein can include varying the length of a reinforcement structure, varying the degree of reinforcement provided by the reinforcement structure along the length of the inner catheter and/or the outer catheter, changing a cross-sectional size and/or shape of the inner catheter and/or the outer catheter, introducing and/or forming one or more discontinuities along a length of the inner catheter and/or the outer catheter (e.g., one or more ribs, notches, grooves, protrusions, etc.), and/or any other suitable means for varying stiffness.

In some embodiments, the catheter devices described herein can include one or more sensors that can provide relative information such as, for example, position of the occlusion members, movement of the actuator, flow rate of the biological agent, and/or any other suitable information. For example, in some embodiments, a sensor can be operably coupled to the actuator 450 of the device 400 and can be configured to provide information associated with a distance that the actuator 450 has been moved. In such embodiments, a user and/or an electronic device can determine a distance between the occlusion member 468 of the first catheter 460 and the occlusion member 478 of the second catheter 470 based on the information from the sensor. In some embodiments, a sensor can be disposed within the third lumen 476 of the second catheter 470 that can be configured to determine a flow rate of irrigation and/or a biological/therapeutic agent therethrough.

In some embodiments, radiopaque markers of gold or tantalum, for example, can also be provided on or in an inner catheter positioned, within or on an occlusion element(s) or member(s), and/or on one or more of the catheters of a catheter system to aid in visualization and to assist in monitoring the position of at least a portion of a catheter device or system on an imaging device (e.g., a fluoroscope, an X-Ray, a Magnetic Resonance Imaging (MRI) scan, a computerized tomography (CT) scan, and/or the like) during a procedure. In some embodiments, an inner catheter (i.e., first catheter) or a secondary catheter (i.e., third catheter) can optionally be coated with a lubricous material, such as silicone, acrylamide, or a hydrophilic polyurethane coating, to ease retraction. Similarly, the outer or second catheter and the occlusion elements can be coated with the lubricous material to ease advancement through a guiding catheter and/or a tortuous vessel.

In some embodiments, an outer diameter of the catheter(s) of a catheter system described herein and non-deployed occlusion elements collectively can be, for example, between about 6 French and about 8 French and thus, can be used with, for example, a 7-9 French guiding catheter (if need be).

In some embodiments, after a guidewire (e.g., the guidewire 280 and/or 380) is removed, a corresponding lumen can be used to establish arterial blood flow distal to the occlusion end (e.g., the distal end portion) of a catheter device or infusion of other therapeutic agents if desired.

In some embodiments, any suitable configuration of the catheter devices can be used to achieve the objectives described herein including, for example, employing one or more catheter devices, employing a contiguous inflation/occluding section having differing stiffness along its length to achieve the two occluding elements, and/or the like.

In some embodiments, to allow endovascular isolation of the pancreatic portion of the splenic artery 40 (see e.g., FIG. 1) as a mechanism to achieve substantially exclusive delivery of a therapeutic agent/cells to the pancreatic parenchyma, a catheter device such as those described herein can include anatomical and mechanical features such as, for example, isolation of the two ends of the pancreatic portion of the artery using two occlusion elements; adjustment of the diameter of the occlusion elements to meet the specific anatomical needs; adjustment of the distance between the two occlusion elements (based on individual variation to selectively isolate for instance the portion of the splenic artery 40 to the pancreas 30 on one hand and maximize the perfusion area on the other hand); an infusion port where injection of contrast can be used to visualize the area of the artery isolated; an infusion port, shaft, and/or aperture design to allow atraumatic and rapid delivery of cells/therapeutic agents; and/or recovery of the occlusion element along with the catheter at the end of the procedure, prior to which flushes through the infusion port can assure clearance of the cells from the isolated space.

In some instances, any portion of the catheter devices can be rotated to allow for a more targeted delivery of the biological/therapeutic agent to a selected tissue. For example, while the infusion apertures are shown as being disposed at a specific position relative to a targeted artery or vessel, in some instances, the catheter device can be rotated to move the infusion aperture to a desired orientation with an artery or vessel. As such, the infusion aperture can be positioned adjacent to a target tissue for a more accurate delivery of the biological agent than would otherwise be possible. In some embodiments, any portion of the catheter devices can include indicia and/or markings that can be associated with the relative position of the infusion aperture. In this manner, a user can visualize the radial position of, for example, an actuator (e.g., the actuator 450) to determine the radial position of the infusion aperture.

Any catheter device described herein and/or any combination of the catheter devices described herein can allow the above goals to be achieved. For example, a catheter device can include two catheters slidably coupled where an inner catheter defines a guidewire housing port and a distal occlusion element, and an outer catheter forms an infusion port and a proximal occlusion element, along with an inner lumen allowing the insertion of the inner catheter. The two catheters can be assembled outside the body with a distance between the two occlusion elements set to a desired length. For example, in some embodiments, the minimum distance between the two occlusion elements can be 3 cm, and the length can be adjusted up to a distance between the two occlusion elements of 25 cm as needed. In some embodiments, the minimum distance between the occlusion elements can be, for example, 0.5 cm.

In some embodiments, a catheter device such as those described herein, which is suitable for accessing, for example, the pancreas 30 (see e.g., FIG. 1), can include features and/or functions, such as, for example, selective isolation of the targeted portion of the pancreatic portion of the splenic artery 40 for targeted delivery of the therapeutic agent to the pancreas 30; an adjustable distance between the two ends of the perfusion/infusion area (e.g., an isolated region) to accommodate individual anatomy to allow isolation of the largest portion of the splenic artery 40 with branches only supplying the pancreatic tail 32 and body 34 (see e.g., FIG. 1) and if clinically indicated, the same catheter can be used to isolate portions of the hepatic artery 54 and/or superior mesenteric artery 52 supplying the head of the pancreas 38; an infusion port allowing first, injection of contrast into the isolated segment to allow direct visualization of the origin of the branches of the splenic artery 40 supplying the pancreatic tissue, and second, introduction of therapeutic drugs/cells, the dimensions and design of the infusion port and catheter shaft allowing rapid and atraumatic delivery of cells; adjustable diameter of the proximal and/or distal occluders to allow both intravariable and intervariable sizes of the splenic artery 40; and/or a self-contained assembly unit with easy retrieval after completion of the procedure.

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. Although various embodiments have been described as having particular features and/or combinations of components, other embodiments are possible having a combination of any features and/or components from any of embodiments as discussed above. For example, the size and specific shape of the various components can be different from the embodiments shown, while still providing the functions as described herein. Furthermore, each feature disclosed herein may be replaced by alternative features serving the same, equivalent or similar purpose, unless expressly stated otherwise. Thus, unless expressly stated otherwise, each feature disclosed is one example only of a generic series of equivalent or similar features.

For example, any of the catheters described herein can be configured to include an infusion lumen and infusion port/aperture to deliver a cell/biologic/therapeutic material to a desired blood vessel. Similarly, any of the catheters described herein can be configured with a guidewire lumen. Thus, any of the lumens of the catheter devices can be defined by any of the catheters of a catheter device or system.

Although the catheter devices have been shown and described as having either two balloon occlusion elements or two filter elements, in alternative embodiments, a catheter device can include a combination of occlusion elements. For example, a catheter device such as those described herein can include one or more balloon occlusion elements and one or more filter element occlusion elements. Further, in some embodiments the catheter devices can include more than one occlusion member.

Although some embodiments of a secondary treatment catheter (690, 790, 890, 990) are described herein with respect to an adjustable catheter device (e.g., 600, 700, 800, 900) and some secondary treatment catheters (1090, 1190) are described with respect to a non-adjustable catheter device (e.g., 1000) it should be understood that any of the embodiments of a secondary treatment catheter device described herein can be used with any embodiment of a catheter device that includes a side port as described herein. Further, although some embodiments are shown and described as being used within a main vessel and a side branch of the main branch, or within a bifurcated vessel, it should be understood that any embodiments of a catheter system using a secondary treatment catheter described herein can be used in either a main vessel and side branch of the main branch, or within a bifurcated vessel or other body lumens within a patient.

Where methods and/or events described above indicate certain events and/or procedures occurring in certain order, the ordering of certain events and/or procedures may be modified. Additionally, certain events and/or procedures may be performed concurrently in a parallel process when possible, as well as performed sequentially as described above.

What is claimed is:

1. An apparatus, comprising:
 a first catheter having a first occlusion member disposed at a distal end portion thereof;
 a second catheter having a second occlusion member disposed at a distal end portion thereof, the second catheter defining a first lumen, a second lumen, and a side port in fluid communication with the second lumen, the first catheter being movably disposed within the first lumen of the second catheter, the first occlusion member and the second occlusion member collectively configured to define a first portion of an isolated target region in a first body lumen; and
 a third catheter having a third occlusion member disposed at a distal end portion thereof, the third catheter being movable through the second lumen of the second catheter and configured to be disposed through the side port into a second body lumen outside of the second lumen,
 the first occlusion member, the second occlusion member, and the third occlusion member collectively configured to define the isolated target region including the first portion of the isolated target region and a second portion of the isolated target region in the second body lumen, the isolated target region being fluidically isolated from other portions of the first body lumen and the second body lumen, one of the first catheter or the second catheter defining an infusion lumen in communication with a side infusion port, the infusion lumen and the side infusion port configured to communicate an active therapeutic material into the isolated target region, the side port having an outer diameter greater than an outer diameter of the side infusion port such that the third catheter can be disposed through the side port.

2. The apparatus of claim 1, wherein the first catheter and the second catheter are movably disposed relative to each other such that a distance between the first occlusion member and the second occlusion can be adjusted.

3. The apparatus of claim 1, wherein the one of the first catheter or the second catheter defining the infusion lumen in communication with the side infusion port is the second catheter.

4. The apparatus of claim 1, further comprising:
a sealing element coupled to the second catheter and covering at least in part the side port, the sealing element configured to permit the third catheter to exit the side port, the sealing element configured to prevent material from entering the side port from outside of the second catheter when the third catheter is not disposed in the side port.

5. The apparatus of claim 4, wherein the sealing element includes a one-way valve.

6. The apparatus of claim 1, further comprising:
a sealing element coupled to a distal end of the second catheter covering at least a portion of a distal opening of the second catheter, the sealing element configured to prevent material from entering the first lumen of the second catheter from outside the second catheter.

7. The apparatus of claim 6, wherein the sealing element includes a one-way valve.

8. The apparatus of claim 1, wherein each of the first occlusion member, the second occlusion member and the third occlusion member are inflatable.

9. The apparatus of claim 1, wherein the infusion lumen is configured to receive a guidewire that can be inserted through the infusion lumen into the isolated target region and used to perforate a portion of a vascular lumen disposed in the isolated target region.

10. The apparatus of claim 4, wherein the second catheter further defines the side infusion port, the side infusion port disposed on the second catheter longitudinally spaced from the side port.

11. The apparatus of claim 1, wherein at least one of the first body lumen or the second body lumen is a splenic artery, a pancreatic magnum artery, or a dorsal pancreatic artery, such that the isolated target region collectively defined by the first occlusion member, the second occlusion member, and the third occlusion member includes a portion of the splenic artery, the pancreatic magnum artery, or the dorsal pancreatic artery and a portion of an artery arising from the splenic artery, the pancreatic magnum artery, or the dorsal pancreatic artery.

12. An apparatus, comprising:
a first catheter including a first occlusion member disposed at a distal end portion thereof;
a second catheter including a second occlusion member disposed proximally of the first occlusion member at a distal end portion of the second catheter and at a spaced distance from the first occlusion member;
a third catheter including a third occlusion member,
at least one of the first catheter or the second catheter defining a first lumen in fluid communication with a first side port and a second lumen in fluid communication with a second side port, the first catheter and the second catheter configured to be inserted into an artery with the first occlusion member and the second occlusion member each in a collapsed configuration, the first occlusion member and the second occlusion member each being movable to an expanded configuration within the artery to define a isolated segment of the artery, the second catheter defining a third lumen, the first catheter being movably disposed within the third lumen of the second catheter such that the first catheter and the second catheter are coaxial and a distance between the first occlusion member and the second occlusion member can be adjusted, the first lumen and the first side port configured to communicate an active treatment material to the isolated segment of the artery, the second lumen and the second side port configured to receive the third catheter such that the third occlusion member can be disposed through the second side port and into a side branch (1) in fluid communication with the artery and (2) located between the first occlusion member and the second occlusion member, the third occlusion member configured to occlude the side branch such that the first occlusion member, the second occlusion member, and the third occlusion member collectively define a fluidically isolated segment including the isolated segment of the artery and a portion of the side branch proximal to the third occlusion member; and a sealing element covering the second side port, the sealing element configured to permit the third catheter to exit the second side port, the sealing element configured to prevent material from entering the second side port from outside of the second lumen when the third catheter is not disposed in the second side port.

13. The apparatus of claim 12, wherein the second catheter defines the first lumen, the first side port, the second lumen, and the second side port.

14. The apparatus of claim 12, wherein the sealing element includes a one-way valve.

15. The apparatus of claim 12, wherein
the third catheter defines a port configured to communicate a treatment agent to the side branch.

16. The apparatus of claim 12, wherein
the third catheter is configured to deliver a coil member to the side branch to permanently occlude the side branch.

17. The apparatus of claim 12, wherein the first lumen is configured to receive a guidewire that can be inserted through the first lumen into the fluidically isolated segment and used to perforate a portion of a vascular lumen disposed in the fluidically isolated segment.

18. A method, comprising
inserting into an artery a first catheter having a first occlusion member disposed at a distal end portion thereof and a second catheter having a second occlusion member disposed proximally of the first occlusion member and at a spaced distance from the first occlusion member, the second catheter defining (i) a first side port and a first lumen in fluid communication with the first side port and (ii) a second side port and a second lumen in fluid communication with the second side port, the first side port disposed distal to and radially offset from the second side port, the first occlusion member and the second occlusion member each being in a collapsed configuration when the first catheter and the second catheter are inserted into the artery, the second catheter defining a third lumen, the first catheter being movably disposed within the third lumen of the second catheter such that the first catheter and the second catheter are coaxial and a distance between the first occlusion member and the second occlusion member can be adjusted;

moving each of the first occlusion member and the second occlusion member to an expanded configuration within the artery to define an isolated segment of the artery;

inserting through the second lumen and the second side port a treatment device having a third occlusion member that can be disposed through the second side port and into a side branch in fluid communication with the artery;

occluding the side branch with the third occlusion member such that the first occlusion member, the second occlusion member, and the third occlusion member collectively define a fluidically isolated treatment region including the isolated segment of the artery and a portion of the side branch between the artery and the third occlusion member; and introducing through the first lumen and the first side port an active treatment material to the fluidically isolated treatment region.

19. The method of claim 18, further comprising:

introducing a coil device into the side branch using the treatment device to permanently occlude the side branch.

20. The method of claim 18, further comprising:

inserting through the first lumen a guidewire to the fluidically isolated treatment region; and perforating a portion of a vascular lumen disposed in the fluidically isolated treatment region.

* * * * *